(12) United States Patent
Hepler et al.

(10) Patent No.: US 12,112,833 B2
(45) Date of Patent: Oct. 8, 2024

(54) SYSTEMS AND METHODS FOR INDEX HOPPING FILTERING

(71) Applicant: 10X Genomics, Inc., Pleasanton, CA (US)

(72) Inventors: Nicolaus Lance Hepler, Oakland, CA (US); Chaitanya Aluru, Princeton, NJ (US); Patrick J. Marks, San Francisco, CA (US); Niranjan Srinivas, Dublin, CA (US); Nigel Delaney, San Francisco, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 447 days.

(21) Appl. No.: 17/168,050

(22) Filed: Feb. 4, 2021

(65) Prior Publication Data

US 2021/0241853 A1 Aug. 5, 2021

Related U.S. Application Data

(60) Provisional application No. 63/022,988, filed on May 11, 2020, provisional application No. 62/969,897, filed on Feb. 4, 2020.

(51) Int. Cl.
*G16B 30/00* (2019.01)
*G06F 16/22* (2019.01)
*G06F 16/23* (2019.01)

(52) U.S. Cl.
CPC ......... *G16B 30/00* (2019.02); *G06F 16/2255* (2019.01); *G06F 16/2365* (2019.01)

(58) Field of Classification Search
None
See application file for complete search history.

(56) References Cited

U.S. PATENT DOCUMENTS 4,683,195 A 5/1987 Mullis et al.
4,683,202 A 5/1987 Mullis et al.
(Continued)

FOREIGN PATENT DOCUMENTS

EP 1336662 A2 8/2003
WO WO 2000/063437 A2 10/2000
(Continued)

OTHER PUBLICATIONS

Qiaoling Li et al. "Reliable multiplex sequencing with rare index mis-assignment on DNB-based NGS platform" BMC Genomics (2019) 20:215 (Year: 2019).*
(Continued)

*Primary Examiner* — Olivia M. Wise
*Assistant Examiner* — Mary C Leverett

(57) ABSTRACT

Methods for index hopping sequence read filtering are provided. Each read in a plurality of reads from a multiplexed reaction comprises an insert portion, and first (molecular identifier) and second (sample index) non-insert portions. For each of a plurality of hashes, a hash data structure is formed with a representation of each read. Each representation comprises a hash of the first non-insert portion of the corresponding read. Read pairs are identified in the hash data structures. Each pair includes a first and second read sharing a common hash value but differing index values. An entry is added into a heterogeneous data structure, for each such pair, that includes the first and second non-insert portions of the first and second reads of the pair. Reads with first non-insert portion values appearing more than a threshold number of times in the heterogeneous data structure are removed from the plurality of reads.

27 Claims, 25 Drawing Sheets

Specification includes a Sequence Listing.

(56) References Cited

U.S. PATENT DOCUMENTS

| | | | |
|---|---|---|---|
| 4,800,159 | A | 1/1989 | Mullis et al. |
| 4,965,188 | A | 10/1990 | Mullis et al. |
| 5,472,881 | A | 12/1995 | Beebe et al. |
| 5,512,462 | A | 4/1996 | Cheng et al. |
| 5,599,675 | A | 2/1997 | Brenner |
| 5,610,287 | A | 3/1997 | Nikiforov et al. |
| 5,807,522 | A | 9/1998 | Shalon et al. |
| 5,837,860 | A | 11/1998 | Anderson et al. |
| 5,919,626 | A | 7/1999 | Shi et al. |
| 6,172,218 | B1 | 1/2001 | Brenner |
| 6,210,891 | B1 | 4/2001 | Nyren et al. |
| 6,258,568 | B1 | 7/2001 | Nyren |
| 6,265,552 | B1 | 7/2001 | Schatz |
| 6,266,459 | B1 | 7/2001 | Walt et al. |
| 6,274,320 | B1 | 8/2001 | Rothberg et al. |
| 6,306,597 | B1 | 10/2001 | Macevicz |
| 6,355,431 | B1 | 3/2002 | Chee et al. |
| 6,391,937 | B1 | 5/2002 | Beuhler et al. |
| 6,737,236 | B1 | 5/2004 | Pieken et al. |
| 6,770,441 | B2 | 8/2004 | Dickinson et al. |
| 6,859,570 | B2 | 2/2005 | Walt et al. |
| 6,867,028 | B2 | 3/2005 | Janulaitis et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,259,258 | B2 | 8/2007 | Kozlov et al. |
| 7,375,234 | B2 | 5/2008 | Sharpless et al. |
| 7,427,678 | B2 | 9/2008 | Pieken et al. |
| 7,709,198 | B2 | 5/2010 | Luo et al. |
| 8,460,865 | B2 | 6/2013 | Chee et al. |
| 8,604,182 | B2 | 12/2013 | Luo et al. |
| 8,951,726 | B2 | 2/2015 | Luo et al. |
| 9,012,390 | B2 | 4/2015 | Holtze et al. |
| 9,512,422 | B2 | 12/2016 | Barnard et al. |
| 9,694,361 | B2 | 7/2017 | Bharadwaj et al. |
| 9,727,810 | B2 | 8/2017 | Fodor et al. |
| 9,783,841 | B2 | 10/2017 | Nolan et al. |
| 9,889,422 | B2 | 2/2018 | Smith et al. |
| 10,002,316 | B2 | 6/2018 | Fodor et al. |
| 10,041,949 | B2 | 8/2018 | Bendall et al. |
| 10,053,723 | B2 | 8/2018 | Hindson et al. |
| 10,059,990 | B2 | 8/2018 | Boyden et al. |
| 10,071,377 | B2 | 9/2018 | Bharadwaj et al. |
| 10,137,449 | B2 | 11/2018 | Bharadwaj et al. |
| 10,138,509 | B2 | 11/2018 | Church et al. |
| 10,150,117 | B2 | 12/2018 | Bharadwaj et al. |
| 10,150,964 | B2 | 12/2018 | Hindson et al. |
| 10,179,932 | B2 | 1/2019 | Church et al. |
| 10,221,442 | B2 | 3/2019 | Hindson et al. |
| 10,343,166 | B2 | 7/2019 | Bharadwaj et al. |
| 10,347,365 | B2 | 7/2019 | Wong et al. |
| 10,400,235 | B2 | 9/2019 | Belhocine et al. |
| 10,428,326 | B2 | 10/2019 | Belhocine et al. |
| 10,550,429 | B2 | 2/2020 | Harada et al. |
| 10,610,865 | B2 | 4/2020 | Bharadwaj et al. |
| 10,815,525 | B2 | 10/2020 | Lucero et al. |
| 11,041,202 | B2 | 6/2021 | Robins et al. |
| 2005/0100900 | A1 | 5/2005 | Kawashima et al. |
| 2006/0188901 | A1 | 8/2006 | Barnes et al. |
| 2006/0240439 | A1 | 10/2006 | Smith et al. |
| 2006/0281109 | A1 | 12/2006 | Ost et al. |
| 2007/0166705 | A1 | 7/2007 | Milton et al. |
| 2008/0280773 | A1 | 11/2008 | Fedurco et al. |
| 2009/0026082 | A1 | 1/2009 | Rothberg |
| 2009/0127589 | A1 | 5/2009 | Rothberg et al. |
| 2010/0055733 | A1 | 3/2010 | Lutolf et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0172105 | A1 | 7/2011 | Gage |
| 2012/0270305 | A1 | 10/2012 | Williamson et al. |
| 2013/0079232 | A1 | 3/2013 | Kain et al. |
| 2013/0260372 | A1 | 10/2013 | Buermann et al. |
| 2014/0079923 | A1 | 3/2014 | George et al. |
| 2014/0155295 | A1 | 6/2014 | Hindson et al. |
| 2014/0378345 | A1 | 12/2014 | Hindson et al. |
| 2015/0376609 | A1 | 12/2015 | Hindson et al. |
| 2015/0376700 | A1 | 12/2015 | Schnall-Levin et al. |
| 2017/0016053 | A1 | 1/2017 | Beechem et al. |
| 2017/0253918 | A1 | 9/2017 | Kohman et al. |
| 2018/0052081 | A1 | 2/2018 | Kohman et al. |
| 2018/0105808 | A1 | 4/2018 | Mikkelsen et al. |
| 2018/0156784 | A1 | 6/2018 | Usmani et al. |
| 2018/0245142 | A1 | 8/2018 | So et al. |
| 2018/0312873 | A1 | 11/2018 | Zheng |
| 2019/0032121 | A1 | 1/2019 | Daugharthy et al. |
| 2019/0177800 | A1 | 6/2019 | Boutet et al. |
| 2019/0323088 | A1 | 10/2019 | Boutet et al. |
| 2019/0367969 | A1 | 12/2019 | Bell et al. |
| 2020/0392479 | A1 | 12/2020 | Blainey |
| 2021/0174898 | A1 | 6/2021 | Bell |
| 2021/0241853 | A1 | 8/2021 | Hepler et al. |
| 2022/0220470 | A1 | 7/2022 | Pan |

FOREIGN PATENT DOCUMENTS

| | | |
|---|---|---|
| WO | WO 2005/065814 A1 | 7/2005 |
| WO | WO 2006/064199 A1 | 6/2006 |
| WO | WO 2007/010251 A2 | 1/2007 |
| WO | WO 2009099602 A1 | 8/2009 |
| WO | WO 2011/094669 A1 | 8/2011 |
| WO | WO 2011/127099 A1 | 10/2011 |
| WO | WO 2012/140224 A1 | 10/2012 |
| WO | WO 2014/060483 A1 | 4/2014 |
| WO | WO 2014/163886 A1 | 10/2014 |
| WO | WO 2014/189957 | 11/2014 |
| WO | WO 2014/189957 A2 | 11/2014 |
| WO | WO 2014/210225 A1 | 12/2014 |
| WO | WO 2014/210233 A1 | 12/2014 |
| WO | WO 2014/210353 | 12/2014 |
| WO | WO 2014/210353 A2 | 12/2014 |
| WO | WO 2015/161173 A1 | 10/2015 |
| WO | WO 2015/200871 | 12/2015 |
| WO | WO 2015/200871 A1 | 12/2015 |
| WO | WO 2016/007839 | 1/2016 |
| WO | WO 2016/057552 | 4/2016 |
| WO | WO 2016/162309 | 10/2016 |
| WO | WO 2016/166128 | 10/2016 |
| WO | WO 2017/027367 | 2/2017 |
| WO | WO 2017/027368 | 2/2017 |
| WO | WO 2017/144338 | 8/2017 |
| WO | WO 2017/147483 | 8/2017 |
| WO | WO 2017/222453 | 12/2017 |
| WO | WO 2018/022809 | 2/2018 |
| WO | WO 2018/045181 | 3/2018 |
| WO | WO 2018/045186 | 3/2018 |
| WO | WO 2018/057999 | 3/2018 |
| WO | WO 2018/075693 | 4/2018 |
| WO | WO 2018/091676 | 5/2018 |
| WO | WO 2018/119447 | 6/2018 |
| WO | WO 2018/119447 A2 | 6/2018 |
| WO | WO 20188/107054 | 6/2018 |
| WO | WO 2018/136856 | 7/2018 |
| WO | WO 2018/218226 | 11/2018 |
| WO | WO 2018/218226 A1 | 11/2018 |
| WO | WO 2019/068880 | 4/2019 |
| WO | WO 2019/075091 | 4/2019 |
| WO | WO 2019/157529 | 8/2019 |
| WO | WO 2019/157529 A1 | 8/2019 |
| WO | WO 2020092646 A1 | 5/2020 |
| WO | WO 2021242793 A2 | 12/2021 |

OTHER PUBLICATIONS

Rick Farouni et al. "Statistical modeling, estimation, and remediation of sample index hopping in multiplexed droplet-based single-cell RNA-seq data" bioRxiv preprint doi: https://doi.org/10.1101/617225 (Year: 2019).*

Anton J M Larsson et al. "Computational correction of index switching in multiplexed sequencing libraries" Nature Methods vol. 14 No. 5 May 2018 (Year: 2018).*

(56) References Cited

OTHER PUBLICATIONS

Jonathan A. Griffiths et al. "Detection and removal of barcode swapping in single-cell RNA-seq data" Nature Communications, (2018) 9:2667 DOI: 10.1038/s41467-018-05083-x (Year: 2018).*
Thermofisher Scientific invitrogen, technical note "How to prevent index hopping" 2019 (Year: 2019).*
Liu D. 2019. Algorithms for efficiently collapsing reads with Unique Molecular Identifiers. PeerJ 7:e8275 http://doi.org/10.7717/peerj. 8275 (Year: 2019).*
Marlon Stoeckius et al. "Cell Hashing with barcoded antibodies enables multiplexing and doublet detection for single cell genomics" Genome Biology (2018) 19:224 (Year: 2018).*
Ramani, V., Deng, X., Qiu, R., Gunderson, K. L., Steemers, F. J., Disteche, C. M., . . . & Shendure, J. (2017). Massively multiplex single-cell Hi-C. Nature methods, 14(3), 263-266. (Year: 2017).*
Smith, A. N. S., Simmons, A. J., Chen, B., Jones, A. L., Solano, M. A. R., Vega, P. N., . . . & Lau, K. S. (2019). Dual indexed design of in-Drop single-cell RNA-seq libraries improves sequencing quality and throughput. bioRxiv, 835488. (Year: 2019).*
MacConaill, L. E., Burns, R. T., Nag, A., Coleman, H. A., Slevin, M. K., Giorda, K., . . . & Thorner, A. R. (2018). Unique, dual-indexed sequencing adapters with UMIs effectively eliminate index cross-talk and significantly improve sensitivity of massively parallel sequencing. BMC genomics, 19, 1-10. (Year: 2018).*
Costello, M., Fleharty, M., Abreu, J. et al. Characterization and remediation of sample index swaps by non-redundant dual indexing on massively parallel sequencing platforms. BMC Genomics 19, 332 (2018). https://doi.org/10.1186/s12864-018-4703-0 (Year: 2018).*
Ning, Z.; Cox, A. J.; Mullikin, J. C. SSAHA: A Fast Search Method for Large DNA Databases. Genome Research, 2001, 11, 1725-1729.*
Farouni and Najafabadi, 2019, "Statistical modeling, estimation, and remediation of sample index hopping in multiplexed droplet-based single-cell RNA-seq data," bioRxiv preprint posted online Apr. 24, 2019; doi: 10.1101/617225.
Griffiths et al., 2018, "Detection and removal of barcode swapping in single-cell RNA-seq data," Nature Communications.
U.S. Appl. No. 17/239,555, filed Apr. 24, 2021.
U.S. Appl. No. 17/367,127, filed Jul. 2, 2021.
U.S. Appl. No. 17/464,561, filed Sep. 1, 2021.
U.S. Appl. No. 63/011,779, entitled "Systems and Methods for Visualizing Adaptive Immune Cell Clonotyping Data," filed Apr. 17, 2020.
U.S. Appl. No. 63/011,783, entitled "Systems and Methods for Identifying Adaptive Immune Cell Clonotypes," filed Apr. 17, 2020.
U.S. Appl. No. 63/073,830, entitled "Systems and Methods for Identifying Cells That are Antigen-Specific for an Immunogenic Feature," filed Sep. 2, 2020.
U.S. Appl. No. 62/017,589, entitled "Processes and Systems for Nucleic Acid Sequence Assembly" filed Jun. 26, 2014.
U.S. Appl. No. 62/969,897 entitled "Systems and Methods for Index Hopping Filtering," filed Feb. 4, 2020.
U.S. Appl. No. 63/022,988 entitled "Systems and Methods for Index Hopping Filtering," filed May 11, 2020.
U.S. Appl. No. 62/041,825, entitled "Pipeline for Spatial Analysis of Analytes," filed Jun. 20, 2020.
U.S. Appl. No. 63/041,823, entitled "Systems and Methods for Identifying Morphological Patterns in Tissue Samples," filed Jun. 20, 2020;.
U.S. Appl. No. 62/047,678 entitled "Biomarkers for Distinguishing Between Aggressive Prostate Cancer and Non-Aggressive Prostate Cancer," filed Jul. 2, 2020.
U.S. Appl. No. 62/839,346 entitled "Spatial Transcriptomics of Biological Analytes in Tissue Samples," filed Apr. 26, 2019.
U.S. Appl. No. 62/886,233, entitled "Systems and Methods for Using the Spatial Distribution of Haplotypes to Determine a Biological Condition" filed Aug. 13, 2019.
U.S. Appl. No. 62/929,686 entitled "Capturing Targeted Genetic Targets Using a Hybridization/Capture Approach", filed.
U.S. Appl. No. 62/938,336, entitled "Pipeline for Spatial Analysis of Analytes," and filed on Nov. 21, 2019.
U.S. Appl. No. 62/970,066, entitled "Capturing Targeted Genetic Targets Using a Hybridization/Capture Approach", filed Feb. 4, 2020.
U.S. Appl. No. 62/979,889, entitled "Capturing Targeted Genetic Targets Using a Hybridization/Capture Approach", filed Feb. 21, 2020.
U.S. Appl. No. 17/078,288, entitled "Capturing Targeted Genetic Targets Using a Hybridization/Capture Approach" filed Oct. 23, 2020.
10X Genomics, "What is a template switch oligo (TSO)?," https://kb.10xgenomics.com/hc/en-US/articles/360001493051-What-is-a-template-switch-oligo-TSO-.
10X Genomics, "What is the difference between Single Cell 3' and 5' Gene Expression libraries?" available on the Internet at kb.10xgenomics.com/hc/en-us/articles/360000939852-What-is-the-difference-between-Single-Cell-3-and-5-Gene-Expression-libraries-.
10X Genomics, Enclone, Internet at Github at 10XGenomics/enclone, last accessed Aug. 31, 2020.
10X Genomics, A "MegaCell Demonstration" by (10X Genomics Datasets, 2017, on the Internet at 10xgenomics.com/solutions/single-cell/).
10X Genomics, 2020, "Technical Note—Interpreting Intronic and Antisense Reads in Single Cell Gene Expression Data", Document No. CG000376, Rev A.
10X Genomics, 2019, "Chromium Next GEM Single Cell 3' Reagent Kits v3.1 User Guide", Document No. CG000204, Rev D.
10X Genomics, 2017, "Chromium Single Cell 3' Reagent Kits v2 User Guide," Document No. CG00052 Rev B.
10X Genomics, 2020, "Chromium Single Cell V(D)J Reagents Kits User Guide," Document No. CG000086, Rev M.
10X Genomics, 2021, "Targeted Gene Expression—Single Cell User Guide", Document No. CG000293, Rev E.
Bailey et al., 2018, "Comprehensive Characterization of Cancer Driver Genes and Mutations," Cell 173(2), pp. 371-385.
Behan et al., 2019, Prioritization of cancer therapeutic targets using CRISPR-Cas9 screens, Nature 568, pp. 511-516.
Blasi et al. 2016, "Label-free cell cycle analysis for high-throughput imaging flow cytometry," Nat. Commun. 7:10256 doi: 10.1038/ncomms10256.
Blondel et al., Jul. 25, 2008, "Fast unfolding of communities in large networks," arXiv:0803.0476v2.
Bourcy et al., 2014, "A Quantitative Comparison of Single-Cell Whole Genome Amplification Methods," Plos One 9(8), e105585.
Caicedo et al., 2017, "Data-analysis strategies for image-based cell profiling," Nature Methods 14(9), pp. 849-863.
Chen et al., 2010, "Clustering-based identification of clonally-related immunoglobulin gene sequence sets," Immunome Res. 6 Suppl 1:S4.
Chen et al., Science 348(6233):aaa6090, 2015.
Compeau et al., 2017, "Why are de Bruijn graphs useful for genome assembly?" Nat Biotechnol. 29(11): 987-991: doi:10.1038/nbt. 2023.
Costello et al., 2018, "Characterization and remediation of sample index swaps by non-redundant dual indexing on massively parallel sequencing platforms," BMC Genomics.
Cunningham, 2007, "Dimension Reduction," University College Dublin, Technical Report UCD-CSI-2007-7.
Cunningham et al., Ensembl 2019, PubMed PMID: 30407521, doi:10.1093/nar/gky1113.
Dave Tang's Blog, "10x single cell BAM files", https://davetang.org/muse/2018/06/06/10x-single-cell-bam-files/.
Denisenko et al., 2019, "Systematic assessment of tissue dissociation and storage biases in single-cell and single-nucleus RNA-seq workflows," bioRxiv preprint doi: https://doi.org/10.1101/832444.
De Vos, 2010, "High content image cytometry in the context of subnuclear organization," Cytometry Part A 77A, pp. 64-75.
Diggins, K.E., P. Brent Ferrell Jr, and Jonathan M. Irish. "Methods for discovery and characterization of cell subsets in high dimensional mass cytometry data." Methods 82 (2015): 55-63.

(56) References Cited

OTHER PUBLICATIONS

Fang et al., 2003, "Fluoride-Cleavable Biotinylation Phosphoramidite for 5'-end-Labelling and Affinity Purification of Synthetic Oligonucleotides," Nucleic Acids Res. 31(2), pp. 708-715.
Fang et al., 2019, "A genetics-led approach defines the drug target landscape of 30 immune-related traits," Nature Genetics 51(7); pp. 1082-1091.
Farouni et al., 2019, "Statistical modeling, estimation, and remediation of sample index hopping in multiplexed droplet-based single-cell RNA-seq data," bioRxiv preprint posted online Apr. 24, 2019; doi: 10.1101/617225.
Fodor, 2002, "A survey of dimension reduction techniques," Center for Applied Scientific Computing, Lawrence Livermore National, Technical Report UCRL-ID-148494.
Ganusov et al., 2007, "Do most lymphocytes in humans really reside in the gut?," Trends Immunol, 208(12), pp. 514-518.
Gao et al., BMC Biol. 15:50, 2017.
Giansanti, 2020, "Fast analysis of scATAC-seq data using a pre-defined set of genomic regions," F1000Research 9, 199.
Gnirke et al., 2009, "Solution Hybrid Selection with Ultra-long Oligonucleotides for Massively Parallel Targeted Sequencing," Nature Biotechnology. Feb. 27(2): 182-189, doi:10.1038/nbt.1523.
Griffiths et al., 2018, "Detection and removal of barcode swapping in single-cell RNA-seq data," Nature Communications 9, Article No. 2667.
Gupta et al., Nature Biotechnol. 36:1197-1202, 2018.
Hershberg et al., 2015, "The analysis of clonal expansion in normal and autoimmune B cell repertoires," Philos Trans R Soc Lond B Biol Sci. 370(1676).
Hoadley et al., 2018, Cell-of-Origin Patterns Dominate the Molecular Classification of 10,000 Tumors from 33 Types of Cancer, Cell 173(2), pp. 291-304.
Hong, 2018, "QSurface: fast identification of surface expression markers in cancer," BMC Syst Biol. 12(Suppl 2):17, doi:10.1186/s12918-018-0541-6.
Illumina, "Effects of index misassignment on multiplexing and downstream analysis," on the Internet at illumina.com, 2017.
Illumina, "An introduction to Next-Generation Sequencing Technology" illumina.com/content/dam/illumina-marketing/documents/products/illumina_sequencing_introduction.pdf, last accessed Feb. 1, 2020.
Kandoth et al., 2013, "Mutational landscape and significance across 12 major cancer types," Nature 502(7471), p. 333-339.
Kurtz et al., 2004, "Versatile and open software for comparing large genomes," Genome Biol doi: 10.1186/gb-2004-5-2-r12.
Kuznetsova et al., 2017, "Generation of populations of antigen-specific cytotoxic T cells using DSs transfected with DNA construct encoding HER2/neu tumor antigen epitopes," BMI Immunology 18:31.
Larsson, A.J.M. et al., "Computational correction of index switching in multiplexed sequencing libraries" Nature Methods vol. 14No. May 2018.
Lee et al., "Fluorescent in situ Sequencing (FISSEQ) of RNA for Gene Expression Profiling in Intact Cells and Tissues", Nat. Protoc. 10(3):442-458, 2015.
Lee et al., 2019, "Multi-ATOM: Ultrahigh-throughput single-cell quantitative phase imaging with subcellular resolution," Journal of Biophotonics doi.org/10.1002/jbio.201800479.
Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi: 10.1182/blood-2003-11-3857.
Li, Q., "Reliable multiplex sequencing with rare index misassignment on DNB-based NGS platform" BMC Genomics (2019) 20:215.
Liu, P., et al. "Recent advances in computer-assisted algorithms for cell subtype identification of cytometry data." Frontiers in cell and developmental biology 8 (2020): 234.
MacConaill, L.E. et al., (2018). "Unique, dual-indexed sequencing adapters with UMIs effectively eliminate index cross-talk and significantly improve sensitivity of massively parallel sequencing." BMC genomics, 19, 1-10.
Malkov and Yashunin, 2016, "Efficient and robust approximate nearest neighbor search using Hierarchical Navigable Small World graphs," arXiv: 1603.09320 at arxiv.org/abs/1603.09320.
Marks et al., 2020, "How repertoire data is changing antibody science," The Journal of Biological Chemistry 295, 9823-9837.
Matsuda et al., 1998, "The complete nucleotide sequence of the human immunoglobulin heavy chain variable region locus," The Journal of Experimental Medicine. 188 (11): 2151-62, doi:10.1084/jem.188.11.2151.
Miles et al., 2011, "Bias in the αβ T-cell repertoire: implications for disease pathogenesis and vaccination," Immunol Cell Biol. 89, pp. 375-387.
Mostovoy et al., 2016, "A hybrid approach for de novo human genome sequence assembly and phasing," Nat. Methods 13, 587-590.
Narasimhan et al., 2016, "Health and population effects of rare gene knockouts in adult humans with related parents," Science 352, pp. 474-477 (2016).
Navin et al., 2011, "Tumour evolution inferred by single-cell sequencing," Nature 472, pp. 90-94.
Ning, Z., et al., "A Fast Search Method for Large DNA Databases. Genome Research," 2001, 11, 1725-1729.
Padmaja, et al. (Aug. 18, 2016). 2016 IEEE 6th International Conference on Advanced Computing (IACC). pp. 31-34. doi: 10.1109/IACC.2016.16, ISBN 978-1-4673-8286-1.
Peng et al., 2015, "Reducing amplification artifacts in high multiplex amplicon sequencing by using molecular barcodes," BMC Genomics. 16(1):589, doi:10.1186/s12864-015-1806-8.
Petegrosso, R. et al. "Machine learning and statistical methods for clustering single-cell RNA-sequencing data." Briefings in bioinformatics 21.4 (2020): 1209-1223.
Quadratic-Time, https://inst.eecs.berkeley.edu/~cs10/labs/cur/programming/algorithms/timing/quadratic-time.html?topic=berkeley_bjc%2Fareas%2Falgorithm-complexity.topic&course=berkeley_bjc.html&noassignment.
Ramani, V., et al. (2017). Massively multiplex single-cell Hi-C. Nature methods, 14(3), 263-266.
Rodriques et al., Science 363(6434):1463-1467, 2019.
Rosati, 2017, "Overview of methodologies for T-cell receptor repertoire analysis," BMC Biotechnology 17:61.
Sanchez-Vega et al., 2018, "Oncogenic Signaling Pathways in the Cancer Genome Atlas," Cell 173(2), pp. 321-337.
Sinha et al., 2017, "Index switching causes 'spreading-of-signal' among multiplexed samples in Illumina HISEQ 4000 DNA sequencing," bioRxiv.
Smith, A.N.S. et al., (2019). Dual indexed design of in-Drop single-cell RNA-seq libraries improves sequencing quality and throughput. bioRxiv, 835488.
Snyder et al., 2012, "Clonal Evolution of Preleukemic Hematopoietic Stem Cells Precedes Human Acute Myeloid Leukemia," Science Translational Medicine 4, 149ra118.
Spitzer et al., 2016, "Mass Cytometry: Single Cells, Many Features," Cell 165(4), pp. 780-791.
Stassen et al., "PARC: ultrafast and accurate clustering of phenotypic data of millions of single cells," BioRxiv preprint doi.org/10.1101/765628.
Stoeckius, M. et al. "Cell Hashing with barcoded antibodies enables multiplexing and doublet detection for single cell genomics" Genome Biology (2018) 19:224 (Year: 2018).
Tandonnet et al., 2017, "Traditional versus 3' RNA-seq in a non-model species," Genom Data. 11:9-16, doi:10.1016/j.gdata.2016.11.002.
Tario et al., 2015, "Dextramer Reagents are Effective Tools for Quantifying CMV Antigen-Specific T Cells from Peripheral Blood Samples," Cytometry Part B (Clinical Cytometry) 888:6-20.
Thermofisher Scientific Invitrogen, technical note "How to prevent index hopping" 2019.
Thorsson et al., 2018, "The Immune Landscape of Cancer," Immunity 48(4), pp. 812-830.

(56) References Cited

OTHER PUBLICATIONS

Traag et al., 2019, "From Louvain to Leiden: guaranteeing well-connected communities," Scientific Reports 9: 5233 at doi.org/10.1038/s41598-019-41695-z.
Trejo et al., PLoS One 14(2):e0212031, 2019.
Turner et al., 2006, Structural determinants of T cell receptor bias in immunity, Nat Rev Immunol 6, pp. 883-894.
Unix & Linux Stack Exchange, "Sorting Lexicographically by 'all fields'", https://unix.stackexchange.com/questions/307293/sorting-lexicographically-by-all-fields.
Vigneron, 2015, "Human Tumor Antigens and Cancer Immunotherapy," BioMed Research International 2015, Article ID 948501.
Voet et al., 2013, "Single-cell paired-end genome sequencing reveals structural variation per cell cycle," Nucleic Acids Res 41: 6119-6138.
Wentian et al., 2014, "Diminishing return for increased Mappability with longer sequencing reads: implications of the k-mer distributions in the human genome," BMC Bioinformatics 15(2).
Wolfgang et al., 2007, "Graphs in molecular biology," BMC Bioinformatics. 8(Suppl 6): S8: doi:10.1186/1471-2105-8-S6-S8.
Wu et al., 2015, "Maturation and Diversity of the VRC01-Antibody Lineage over 15 Years of Chronic HIV-1 Infection," Cell 161(3), pp. 470-485.
Xu et al., 2015, "A Comprehensive Survey of Clustering Algorithms," Ann. Data. Sci. 2(2) 165-193.
Yaari et al., 2015, "Practical guidelines for B cell repertoire sequencing analysis," Genome Medicine 7:121.
Yassai et al., 2009, "A clonotype nomenclature for T cell receptors," Immunogenetics 61, pp. 493-502.
Zahorian et al., 2011, "Nonlinear Dimensionality Reduction Methods for Use with Automatic Speech Recognition," Speech Technologies. doi:10.5772/16863. ISBN 978-953-307-996-7.
Zheng et al., 2016 "Haplotyping germline and cancer genomes with high-throughput linked-read sequencing," Nat. Biotechnol. 34, pp. 303-311.
Zheng et al., 2017, "Massively parallel digital transcriptional profiling of single cells," Nat. Commun. 8, 14049 doi: 10.1038/ncomms14049.
Zong et al., 2012, "Genome-wide detection of single nucleotide and copy-number variations of a single human cell," Science 338, pp. 1622-1626.
Ray et al., Comprehensive identification of mRNA isoforms reveals the diversity of neural cell-surface molecules with roles in retinal u development and disease, Nat Commun. Jul. 3, 2020;11 (1):3328. doi: 10.1038/s41467-020-17009-7.
Yap et al., Polarizing the Neuron through Sustained Co-expression of Alternatively Spliced Isoforms, Cell Rep. May 10, 2016; 15(6): 1316-28. doi: 10.1016/j.celrep.2016.04.012. Epub Apr. 28, 2016.

\* cited by examiner

| Hash data structure repository | 142 |
|---|---|
| Hash data structure 1 | 148-1 |
|   Sequence read 128-1 representation 1-1 | 150-1-1 |
|     First non-insert portion 132-1 hash value 1-1 | 152-1-1 |
|     Second non-insert portion (sample index) 138-1 | 138-1 |
|     Optional file identifier 139-1 | 139-1 |
|   Sequence read 128-2 representation 1-2 | 150-1-2 |
|     First non-insert portion 132-1 hash value 1-2 | 152-1-2 |
|     Second non-insert portion (sample index) 138-2 | 138-2 |
|     Optional file identifier 139-2 | 139-2 |
|   ⋮ | |
|   Sequence read 128-K representation 1-K | 150-1-K |
|     First non-insert portion 132-1 hash value 1-K | 152-1-K |
|     Second non-insert portion (sample index) 138-K | 138-K |
|     Optional file identifier 139-K | 139-K |
| Hash data structure 2 | 148-2 |
|   Sequence read 128-2 representation 2-1 | 150-2-1 |
|     First non-insert portion 132-2 hash value 2-1 | 152-2-1 |
|     Second non-insert portion (sample index) 138-2 | 138-2 |
|     Optional file identifier 139-2 | 139-2 |
|   Sequence read 128-2 representation 1-2 | 150-2-2 |
|     First non-insert portion 132-1 hash value 1-2 | 152-2-2 |
|     Second non-insert portion (sample index) 138-2 | 138-2 |
|     Optional file identifier 139-2 | 139-2 |
|   ⋮ | |
|   Sequence read 128-K representation 2-K | 150-2-K |
|     First non-insert portion 132-1 hash value 2-K | 152-3-K |
|     Second non-insert portion (sample index) 138-K | 138-K |
|     Optional file identifier 139-K | 139-K |
|   ⋮ | |
| Hash data structure Q | 148-Q |

Figure 1B

For each respective hash 140 in a plurality of hashes, form a corresponding hash data structure 148. The corresponding hash data structure includes a representation 150 of each respective sequence read 128, in the plurality of sequence reads, and comprises a hash value 152, of length L nucleotide positions, where L is less than N, formed by hashing at least the corresponding first non-insert portion 132 of the respective sequence read 128 in accordance with the respective hash 140, thereby forming a plurality of hash data structures 148. — 228

N is between 10 and 100, and M is between 5 and 20. — 230

L is between 4 and 99. — 232

N is between 36 and 40, and M is 8. — 234

L is between 4 and 99. — 236

The hash value 152 formed by hashing at least the corresponding first non-insert portion 132 of the respective sequence read 128 in accordance with the respective hash 140 comprises forming the hash value 152 from a predetermined subset of nucleotide positions in the corresponding first non-insert portion 132. The predetermined subset of nucleotide positions is defined by the respective hash 140 and is unique to the respective hash 140. — 238

Each respective hash 140 in the plurality of hashes defines a different predetermined subset of nucleotide positions in the first non-insert portion 132. — 240

The plurality of hashes consists of between three and one hundred hashes. — 242

Figure 2C

| Flowcell | Lena Id | Reads Per Cell | Dual Index Filtered Loss | Filtered Loss | % All Reads Removed by DI Also Removed by IHF | % Cell Barcode Reads Removed by DI Also Removed by IHF | % Non-Cell Barcode Reads Removed by DI Also Removed by IHF |
|---|---|---|---|---|---|---|---|
| HG7LTDRXX | 148230 | 117,799 | 1.92% | 2.58% | 84.39% | 1.56% | 97.27% |
| HG7LTDRXX | 148231 | 141,405 | 2.32% | 3.51% | 75.81% | 2.73% | 95.09% |
| HG7LTDRXX | 148232 | 125,174 | 2.19% | 3.14% | 84.00% | 1.58% | 97.01% |
| HG7LTDRXX | 148233 | 151,874 | 2.19% | 2.99% | 76.39% | 1.81% | 94.77% |
| HG7LTDRXX | 148234 | 109,364 | 2.23% | 3.03% | 80.38% | 1.97% | 96.34% |
| HG7LTDRXX | 148235 | 153,789 | 2.25% | 3.42% | 74.55% | 2.30% | 95.40% |

Dual-indexed libraries pooled on a separate lane.

| Flowcell | Lena Id | Reads Per Cell | Dual Index Loss | Filtered Loss | % All Reads Removed by DI Also Removed by IHF | % Cell Barcode Reads Removed by DI Also Removed by IHF | % Non-Cell Barcode Reads Removed by DI Also Removed by IHF |
|---|---|---|---|---|---|---|---|
| HGFGTDRXX | 148265 | 126,490 | 11.93% | 18.67% | 95.82% | 47.81% | 98.64% |
| HGFGTDRXX | 148266 | 157,054 | 10.04% | 18.33% | 93.33% | 22.61% | 98.27% |
| HGFGTDRXX | 148267 | 131,360 | 10.47% | 17.95% | 94.71% | 29.43% | 98.53% |
| HGFGTDRXX | 148268 | 146,506 | 10.77% | 18.32% | 92.91% | 23.73% | 98.23% |
| HGFGTDRXX | 148269 | 112,772 | 8.72% | 16.82% | 93.29% | 21.15% | 98.43% |
| HGFGTDRXX | 148270 | 158,763 | 8.80% | 18.69% | 93.53% | 22.15% | 98.29% |

Same samples, single- and dual-indexed pooled together.

Figure 11

CSV Config Example:

| R1 | R2 | SampleId |
|---|---|---|
| test1_S2_L001_R1_001.fastq.gz | test1_S2_L001_R2_001.fastq.gz | 2 |
| test2_S6_L001_R1_001.fastq.gz | test2_S6_L001_R2_001.fastq.gz | 6 |

Figure 14A

```
/mnt/hashhopper/ihf/csi1028-sketch/1.0 >= cat outs/filtered_reads.csv
"Sample ID","Starting Number of Reads","Number of Reads Removed"
1,250025963,14076740
2,225861154,7932283
3,268814987,11344775
4,263931220,10943788
```

Figure 14B

```
package: hashhopper
version: 0.1.0
Dec 17 10:27:32.398 INFO logging to `output/_log`
Dec 17 10:27:32.398 INFO inferring inputs from directory `/mnt/home/lance.hepler/sw/index_hopping_filter/test`
Dec 17 10:27:32.401 INFO auto-detected R1 length: 28
Dec 17 10:27:32.767 INFO clean fastq.gz files located at `output/outs/fastq_path`
Dec 17 10:27:32.829 INFO writing summary to `output/outs/web_summary.html`
Dec 17 10:27:32.905 INFO success!
~/sw/index_hopping_filter (master) >— tree output/
output/
├── _log
└── outs
    ├── fastq_path
    │   ├── test1_S2_L001_R1_001.fastq.gz
    │   ├── test1_S2_L001_R2_001.fastq.gz
    │   ├── test2_S6_L001_R1_001.fastq.gz
    │   └── test2_S6_L001_R2_001.fastq.gz
    ├── filtered_reads.csv
    ├── input.csv
    └── web_summary.html 2 directories, 8 files
```

Figure 15

Reads Filtered by Sample

| Sample ID | Starting Number of Reads | Number of Reads Removed |
|---|---|---|
| 2 | 10 | 4 (40.0%) |
| 6 | 11 | 3 (27.3%) |

Run Details

| | |
|---|---|
| Input path | /mnt/home/abigail.gallegos/repos/10xdev/index_hopping_filter/test/test.csv |
| HashHopper version | 0.1.0 |

Figure 16

SYSTEMS AND METHODS FOR INDEX HOPPING FILTERING

CROSS REFERENCE TO RELATED APPLICATIONS

This application claims priority to U.S. Provisional Patent Application No. 63/022,988 entitled "SYSTEMS AND METHODS FOR INDEX HOPPING FILTERING," filed May 11, 2020, which is hereby incorporated by reference. This application also claims priority to U.S. Provisional Patent Application No. 62/969,897 entitled "SYSTEMS AND METHODS FOR INDEX HOPPING FILTERING," filed Feb. 4, 2020, which is hereby incorporated by reference.

SEQUENCE LISTING

The instant application contains a Sequence Listing which has been submitted electronically in ASCII format and is hereby incorporated by reference in its entirety. Said ASCII copy, created on May 11, 2020, is named 104371-5035-PR01_ST25 and is 2 kilobytes in size.

TECHNICAL FIELD

This specification describes technologies relating to filtering out erroneous (index hopping) sequence reads in multiplexed sequencing reaction datasets.

BACKGROUND

Sample index hopping can confound the analysis of multiplexed sequencing data due to the resulting erroneous assignment of some, or even all, of the sequencing reads generated by a cDNA fragment in a given sample to other samples. In those target samples, the data cross-contamination artifact takes the form of phantom molecules, molecules that exist only in the data by virtue of read misassignment. See Farouni and Najafabadi, 2019, "Statistical modeling, estimation, and remediation of sample index hopping in multiplexed droplet-based single-cell RNA-seq data," bioRxiv preprint posted online Apr. 24, 2019; doi: 10.1101/617225, which is hereby incorporated by reference.

Ever since the emergence of next-generation sequencing technologies, the speed and throughput by which whole-genome DNA and RNA sequencing can be performed has been steadily increasing. For example, currently, a total of 2.5 billion single reads can be generated on each of the four lanes that comprise a single S4 flow cell on a NovaSeq 6000 system (Illumina, San Diego, California), compared to 350 million reads on each of eight lanes of a HiSeq 4000 (Illumina). However, given that, for most sequencing studies, the number of reads required to achieve an adequate transcriptome coverage tends to be in the tens of millions, it then becomes necessary to resort to sample multiplex sequencing strategies to fully utilize the massive capacity and cost efficiency that the patterned flow cell of many modern sequencers have. The process of sample multiplexing involves adding a sample barcode index to each cDNA fragment during library preparation (to one end in single-indexing or to both ends in dual-indexing). Then, cDNA fragments from multiple samples are subsequently pooled together in the same lane to be cluster-amplified and sequenced. Finally, the generated sequenced reads are demultiplexed into their respective source samples using the sample barcode indices. In one example of multiplexing technology, up to 384 samples are multiplexed using a 96-plex on each of the four lanes of a NovaSeq S4 flow cell.

Unfortunately, sample multiplexing can cause an appreciable percentage of the demultiplexed sequenced reads to be misassigned to an incorrect sample barcode. Although sample read misassignments can arise due to several factors, one specific mechanism, termed sample index hopping, is a significant cause of read misassignments in patterned flow cells. While not intending to limited by any particular theory, index hopping is believed to result from the presence of free-floating indexing primers that attach to the pooled cDNA fragments just before the exclusion amplification step that generates clusters on the flow cell (See, 2017, Illumina, 2017, "Effects of index misassignment on multiplexing and downstream analysis," on the Internet at illumina.com). Several studies have shown that the existence of substantial number of reads assigned to incorrect samples in an experiment can potentially lead to signal artifacts and spurious results. For a review of such studies, see Farouni and Najafabadi, 2019, "Statistical modeling, estimation, and remediation of sample index hopping in multiplexed droplet-based single-cell RNA-seq data," bioRxiv preprint posted online Apr. 24, 2019; doi: 10.1101/617225, which is hereby incorporated by reference.

Given the large amount of public data that have been and are being generated using multiplexed sequencing, index hopping is a cause of concern and needs to be addressed. For example, Sinha et al., 2017, "Index switching causes 'spreading-of-signal' among multiplexed samples in Illumina HISEQ 4000 DNA sequencing," bioRxiv, reported that 5-10% of sequencing reads were incorrectly assigned a sample index in a multiplexed pool of plate-based scRNA-seq samples. Costello et al., 2018, "Characterization and remediation of sample index swaps by non-redundant dual indexing on massively parallel sequencing platforms," BMC Genomics used a non-redundant dual indexing adapters developed in-house and performed an exhaustive study across multiple libraries (whole genomes, exome, and stranded RNA) and sequencer models (HiSeq 4000, NovaSeq 6000 and HiSeqX) to determine the rate of index hopping. They observed a rate of 0.2% to 6% in all sequencing runs. In 10× (Pleasanton, California) libraries, this index hopping manifest as cells belonging to another sample appearing in another in which they do not belong, or cells expressing genes in a manner they did not originally exhibit, or mis-assembly of V(D)J clonotypes from an immune profiling experiment.

Given that index hopping likely occurs in all sequencing platforms that use patterned flow cells, one can resort to a number of experimental strategies to mitigate sample index hopping from affecting the integrity of experimental data. For example, only one sample per lane can be used, that is multiplexing can be avoided altogether. By avoiding multiplexing altogether and running one sample per lane, one can confine the sample indices in a given lane to be for one given sample only thus minimizing the risk of index hopping from occurring in the first place. However, sample read misassignments can still occur due to other causes. Moreover, avoiding multiplexing altogether increases the costs of running experiments on most sequencing platforms. As a result, avoiding multiplexing altogether is not a satisfactory solution to the problem of index hopping in many instances.

Another approach to addressing the index hopping problem is to use a unique-at-both-ends dual indexing library. By utilizing two unique barcodes for each sample, sample misassignment would occur only when both sample indices hop. Given the low probability that such an event would occur, index hopping can be reduced and computationally mitigated by discarding reads with unexpected combinations. However, the use of use a unique-at-both-ends dual indexing library has drawbacks. For instance, their use in plate-based single cell experiments where many samples (e.g. cells) need to be multiplexed together is problematic since dual indexing restricts the number of possible samples that can multiplexed together (See, Griffiths et al., 2018, "Detection and removal of barcode swapping in single-cell RNA-seq data," Nature Communications). Moreover, unique-at-both-ends dual-indexing is incompatible with single index droplet-based protocols such as the widely used 10× Genomics single cell protocol.

Given the limitations of existing experimental strategies to eliminate index hopping, the urgency to develop computational strategies instead has intensified since the phenomenon was first discovered. See Farouni and Najafabadi, 2019, "Statistical modeling, estimation, and remediation of sample index hopping in multiplexed droplet-based single-cell RNA-seq data," bioRxiv preprint posted online Apr. 24, 2019; doi: 10.1101/617225. Some existing solutions to this problem rely on exact matching, which are not satisfactory for many purposes because they do not feasibly permit consideration of sequencing errors, which can contribute sufficiently enough to adversely affect the outputs of e.g. cell calling in the 10× CellRanger pipelines. Alternatively, other methods rely on downstream counts after, for example, the adverse effect on cell calling has already been observed. See Farouni and Najafabadi, Id., and Griffiths et al., 2018, "Detection and removal of barcode swapping in single-cell RNA-seq data," Nature Communications 9, Article number: 2667.

Given the above background, what is needed in the art are improved computational strategies for detecting index hopped sequence reads.

SUMMARY

The present disclosure addresses the deficiencies in the prior art by providing improved systems and methods for detecting index hopping sequence reads prior to their use in down-stream analysis. Moreover, advantageously, the disclosed index hopping detection systems and methods can identify index hopped sequence reads without relying on exact matching. That is, the disclosed systems and methods can identify index hopped sequence reads even in the context of sequencing errors. While algorithms that permit sequence errors, rather than exact matching, often require quadratic-time comparisons and thus can be computationally expensive, in some embodiments of the present disclosure, the disclosed systems and methods provide ways of pre-filtering out sequence reads prior to performing such computationally expensive algorithms. In this way, in such embodiments, the potentially large number of search comparisons that necessarily are made when permitting sequence error are substantially reduced.

One aspect of the present disclosure provides a method of filtering out erroneous sequence reads. The method comprises, at a computer system having one or more processors, and memory storing one or more programs for execution by the one or more processors, obtaining a plurality of sequence reads from a multiplexed sequencing reaction. Each respective sequence read in the plurality of sequence reads comprises a corresponding insert (coding) portion, a corresponding first non-insert portion consisting of N nucleotide positions, and a corresponding second non-insert portion consisting of M nucleotide positions. N and M are positive integers. Each corresponding first non-insert portion represents an identifier of a unique molecule (e.g., a unique molecular identifier). Each corresponding second non-insert portion comprises a sample index. The plurality of sequence reads includes one or more first sequence reads from a first sample that each have a first value for the sample index. The plurality of sequence reads includes one or more second sequence reads from a second sample that each have a second value for the sample index.

A corresponding hash data structure is formed for each respective hash in a plurality of hashes. The corresponding hash data structure includes a representation of each respective sequence read in the plurality of sequence reads. Each such representation comprises a hash value, of length L nucleotide positions, where L is less than N, formed by hashing at least the corresponding first non-insert portion of the respective sequence read in accordance with the respective hash. The hashing of the plurality of sequence reads, for each respective hash in the plurality of hashes, results in the formation of a plurality of hash data structures.

For each respective hash data structure in the plurality of hash data structures, a first procedure is performed. This first procedure comprises identifying one or more unique sequence read pairs, e.g., in quadratic-time, in the respective hash data structure. Each such sequence read pair includes a corresponding first and second sequence read sharing a common hash value but having different second values for the sample index. A corresponding entry is added into a heterogeneous data structure for each respective unique sequence read pair in the one or more unique sequence read pairs identified using the hash data structure. The corresponding entry includes at least the corresponding first and second non-insert portions of the corresponding first sequence read and the corresponding first and second non-insert portions of the corresponding second sequence read of the respective unique sequence read pair.

The heterogeneous data structure is used to identify a set of sequence reads to be flagged for removal. Each sequence read in the set of sequence reads has a corresponding first non-insert portion value that appears more than a threshold number of times in the heterogeneous data structure. This set of sequence reads is removed from the plurality of sequence reads thereby filtering out erroneous sequence reads from the original plurality of sequence reads.

In some embodiments, the plurality of sequence reads is from more than five different biological samples and comprises more than one hundred thousand sequence reads.

In some embodiments, the identifier of the unique molecule has a nucleotide length of between 8 nucleotide positions and 20 nucleotide positions.

In some embodiments, the identifier of the unique molecule encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1\times10^{12}\}$.

In some embodiments, the corresponding first non-insert portion of each respective sequence read in the plurality of sequences reads further comprises a corresponding independent barcode, from a plurality of barcodes, where each barcode in the plurality of barcodes represents a different gel bead-in emulsion in a plurality of gel bead-in emulsions. In some embodiments, each barcode in the plurality of barcodes encodes a unique predetermined value selected from the set {1, ..., 1024}, selected from the set {1, ..., 4096}, selected from the set {1, ..., 16384}, selected from the set {1, ..., 65536}, selected from the set {1, ..., 262144}, selected from the set {1, ..., 1048576}, selected from the set {1, ..., 4194304}, selected from the set {1, ..., 16777216}, selected from the set {1, ..., 67108864}, or selected from the set {1, ..., 1×10$^{12}$}.

In some embodiments, N is between 10 and 100, and M is between 5 and 20. In some embodiments, N is between 36 and 40, and M is 8. In some embodiments, L is between 4 and 99. In some embodiments, L is between 4 and 35.

In some embodiments, the hash value formed by hashing at least the corresponding first non-insert portion of the respective sequence read in accordance with the respective hash comprises forming the hash value from a predetermined subset of nucleotide positions in the corresponding first non-insert portion, where the predetermined subset of nucleotide positions is defined by the respective hash and is unique to the respective hash. In some such embodiments, each respective hash in the plurality of hashes defines a different predetermined subset of nucleotide positions in the first non-insert portion.

In some embodiments, the plurality of hashes consists of between three and one hundred hashes.

In some embodiments, the method further comprises evaluating each respective sequence read in the plurality of sequence reads to determine whether it satisfies the uniqueness test by performing a second procedure that comprises (i) obtaining a table $T_{HH}$ that comprises the corresponding first and second non-insert portions of each sequence read in the plurality of sequence reads, sorted on the first non-insert portion, (ii) identifying each respective first non-insert portion represented in $T_{HH}$ for which a threshold number of unique second non-coding portion pairs can be made from pairs of sequence reads in $T_{HH}$ having the respective first non-insert portion, where each second non-coding portion pair in the threshold number of unique second non-coding portion pairs comprises an independent pair of different second non-coding portion sequences, and (iii) removing each sequence read in the plurality of sequence reads having an identified first non-insert portion. In some such embodiments, the threshold number is a number between 500 and 100,000. In some such embodiments, the threshold number is a number between 5,000 and 25,000.

In some embodiments, the method further comprises reducing a computational expense of the identification of read pairs in the respective hash tables by removing each respective sequence read in the plurality of sequence reads that fails to satisfy a uniqueness test prior to forming the hash tables.

In some embodiments, the corresponding hash data structure is a corresponding first table, each row in the corresponding first table includes the representation of a respective sequence read in the plurality of sequence reads, the representation of each sequence read further comprises the corresponding second non-insert portion of the sequence read, and the corresponding first table is sorted on hash value. In some such embodiments, each sequence read further comprises a file identifier identifying a file name that contains the sequence read and the representation of each sequence read in the corresponding first table further comprises the file identifier.

In some embodiments, the heterogeneous data structure is a second table, each row in the corresponding second table includes a corresponding entry, and the second table is sorted in lexicographic field order using at least the first and second non-insert portions of the corresponding first sequence read and the first and second non-insert portions of the corresponding second sequence read of each corresponding entry in the second table. In some such embodiments, the corresponding entry further includes the file identifier of the corresponding first sequence read and the file identifier of the corresponding second sequence read of the respective unique sequence read pair.

In some embodiments, the plurality of sequence reads includes sequence reads from a plurality of biological samples, where each biological sample in the plurality of biological samples is assigned a different sample index value.

In some embodiments, the plurality of sequence reads is obtained by loading test nucleic acid onto a plurality of gel bead-in emulsions beads.

In some embodiments, the threshold number of times is an integer that greater than 1 and that is less than a number of hashes in the plurality of hashes.

In some embodiments, the threshold number of times is four, five, six, or seven and the number of hashes in the plurality of hashes is eight.

In some embodiments, the multiplexed sequencing reaction is a duplex sequencing reaction.

Another aspect of the present disclosure provides a computing system, comprising one or more processors and memory storing one or more programs to be executed by the one or more processors. The one or more programs comprises instructions for obtaining a plurality of sequence reads from a multiplexed sequencing reaction. Each respective sequence read in the plurality of sequence reads comprises a corresponding insert (coding) portion, a corresponding first non-insert portion consisting of N nucleotide positions, and a corresponding second non-insert portion consisting of M nucleotide positions. N and M are positive integers. Each corresponding first non-insert portion represents an identifier of a unique molecule (e.g., a unique molecular identifier). Each corresponding second non-insert portion comprises a sample index. The plurality of sequence reads includes one or more first sequence reads from a first sample that each have a first value for the sample index. The plurality of sequence reads includes one or more second sequence reads from a second sample that each have a second value for the sample index.

For each respective hash in a plurality of hashes, a corresponding hash data structure is formed, where the corresponding hash data structure includes a representation of each respective sequence read in the plurality of sequence reads that comprises a hash value, of length L nucleotide positions, where L is less than N. Each such representation is formed by hashing at least the corresponding first non-insert portion of the respective sequence read in accordance with the respective hash, thereby forming a plurality of hash data structures. For each respective hash data structure in the plurality of hash data structures, a first procedure is performed.

The first procedure comprises identifying zero or more unique sequence read pairs in a respective hash data structure, e.g., in quadratic-time, where each respective sequence read pair in the one or more unique sequence read pairs includes a corresponding first sequence read and a corresponding second sequence read sharing a common hash value and having different second values for the sample index. A corresponding entry is added into a heterogeneous data structure for each respective unique sequence read pair in the zero or more unique sequence read pairs identified using the respective hash data structure. The corresponding entry includes at least the corresponding first and second non-insert portions of the corresponding first sequence read and the corresponding first and second non-insert portions of the corresponding second sequence read of the respective unique sequence read pair;

The heterogeneous data structure is used to identify a set of sequence reads to be flagged for removal. Each sequence read in the set of sequence reads has a corresponding first non-insert portion value that appears more than a threshold number of times in the heterogeneous data structure. This set of sequence reads is removed from the plurality of sequence reads thereby filtering out erroneous sequence reads.

The present disclosure further provides a non-transitory computer readable storage medium storing one or more programs configured for execution by a computer, the one or more programs comprising instructions for carrying out any of the disclosed methods.

Thus, these methods, computers, systems, and non-transitory computer readable storage medium provide improvements in filtering out erroneous (index hopping) sequence reads in multiplexed sequencing reaction datasets.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings. In the figures that include method flowcharts, boxes that are dashed indicate example embodiments.

FIGS. 1A, 1B, 1C and 1D provides an example block diagram illustrating a computing device in accordance with some implementations.

FIGS. 2A, 2B, 2C, 2D, and 2E illustrate a method of filtering out erroneous sequence reads in accordance with some embodiments of the present disclosure.

FIG. 11 provides the results of an assay measuring the performance of a method of filtering out erroneous sequence reads, in accordance with some embodiments of the present disclosure, using a dual-indexed sequencing library as a ground truth comparison.

FIGS. 14A and 14B illustrate example outputs in comma separated value (CSV) format for the method of filtering out erroneous sequence reads, in accordance with some embodiments of the present disclosure.

FIG. 15 illustrates an example implementation of the method of filtering out erroneous sequence reads, in accordance with some embodiments of the present disclosure.

FIG. 16 illustrates a web summary output, in accordance with some embodiments of the present disclosure.

DETAILED DESCRIPTION

Figure 1A:
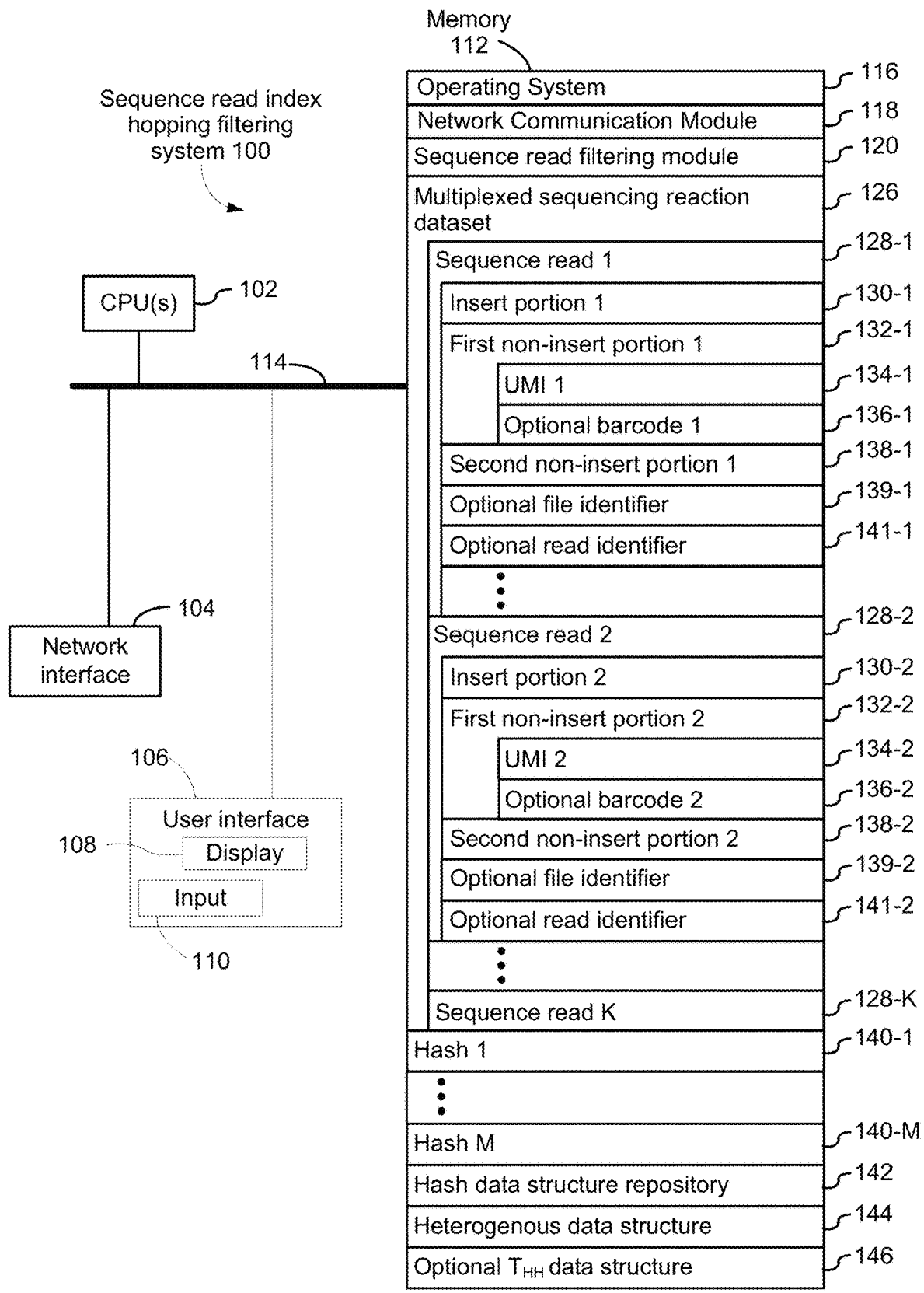

The present disclosure generally provides methods, processes, and particularly computer implemented processes and non-transitory computer program products for use in the analysis of genetic sequence data, and in particular, for filtering out erroneous sequence reads in multiplexed sequence data. Details of implementations are now described in relation to the Figures.

FIGS. 1A through 1D illustrate a block diagram illustrating a sequence read index hopping filtering system 100 in accordance with some implementations. The device 100 in some implementations includes one or more processing units CPU(s) 102 (also referred to as processors), one or more network interfaces 104, a user interface 106, a memory 112, and one or more communication buses 114 for interconnecting these components. The communication buses 114 optionally include circuitry (sometimes called a chipset) that interconnects and controls communications between system components. The memory 112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 112 optionally includes one or more storage devices remotely located from the CPU(s) 102. The memory 112, or alternatively the non-volatile memory device(s) within the memory 112, comprises a non-transitory computer readable storage medium. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the device 100 with other devices, or a communication network;
- a sequence read filtering module 120 for filtering out erroneous sequence reads from multiplexed sequencing data;
- a multiplexed sequencing reaction dataset 126 that comprises a plurality of sequence reads 128, each respective sequence read in the plurality of sequence reads comprising (i) a corresponding insert portion 130, (ii) a corresponding first non-insert portion 132 consisting of N nucleotide positions represents an identifier of a unique molecule (e.g., a UMI 134 and optionally a barcode 136), (iii) a corresponding second non-insert portion 138 consisting of M nucleotide positions, (iv) an optional file identifier 139 for the respective sequence read and (v) an optional read identifier for the respective sequence read;
- a plurality of hashes, each respective hash (mask) 140 in the plurality of hashes providing a unique predetermined hash of the corresponding first non-insert portion of a respective sequence read 128;
- a hash data structure repository 142 comprising a corresponding hash data structure 148 for each hash 140 in the plurality of hashes, the corresponding hash data structure 148 comprising a representation 150 of each respective sequence read 128 in the plurality of sequence reads (the multiplexed sequencing reaction dataset 126) that comprises (i) a hash value 152, of length L nucleotide positions, where L is less than N, formed by hashing at least the corresponding first non-insert portion 132 of the respective sequence read 128 in accordance with the respective hash 140, (ii) the second non-insert portion 138 of the respective sequence read, and (iii) optionally a file identifier 139 of the respective sequence read;
- a heterogeneous data structure 144 comprising a plurality of entries 149, each entry 149 representing a sequence read pair (128-A, 128-B) and comprising at least a corresponding first 132-A and second 138-A non-insert portions of a corresponding first sequence read 128-A and a corresponding first 132-B and second 138-B non-insert portions of a corresponding second sequence read 128-B of a unique sequence read pair; and
- optionally, a $T_{HH}$ data structure 146 that comprises, for each sequence read 128 in the plurality of sequence reads (the multiplexed sequencing reaction dataset 126), the first non-insert portion 132, the second non-insert portion, and the optional file identifier 139 of the respective sequence read.

In some implementations, the user interface 106 includes an input device (e.g., a keyboard, a mouse, a touchpad, a track pad, and/or a touch screen) 100 for a user to interact with the system 100 and a display 108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIGS. 1A through 1D shows a "sequence read index hopping filtering system," the figures are intended more as functional description of the various features that may be present in computer systems, than as a structural schematic of the implementations described herein. In practice, and as recognized by those of ordinary skill in the art, items shown separately could be combined and some items could be separated. In some embodiments, elements in FIGS. 1A through 1D can be implemented in the order shown, or in a different order as will be apparent to one of ordinary skill in the art.

Now that systems for sequence read index hopping filtering in accordance with embodiments of the present disclosure in conjunction with FIGS. 1A through 1D, methods for sequence read index hopping filtering in accordance with the present disclosure will be described in conjunction with FIGS. 2A through 2E.

FIGS. 2A through 2E provide a flow chart illustrating a method of filtering out erroneous sequence reads (block 202). The method is performed at a computer system 100 having one or more processors 102, and memory storing one or more programs for execution by the one or more processors in accordance with some embodiments (204).

Figure 4:
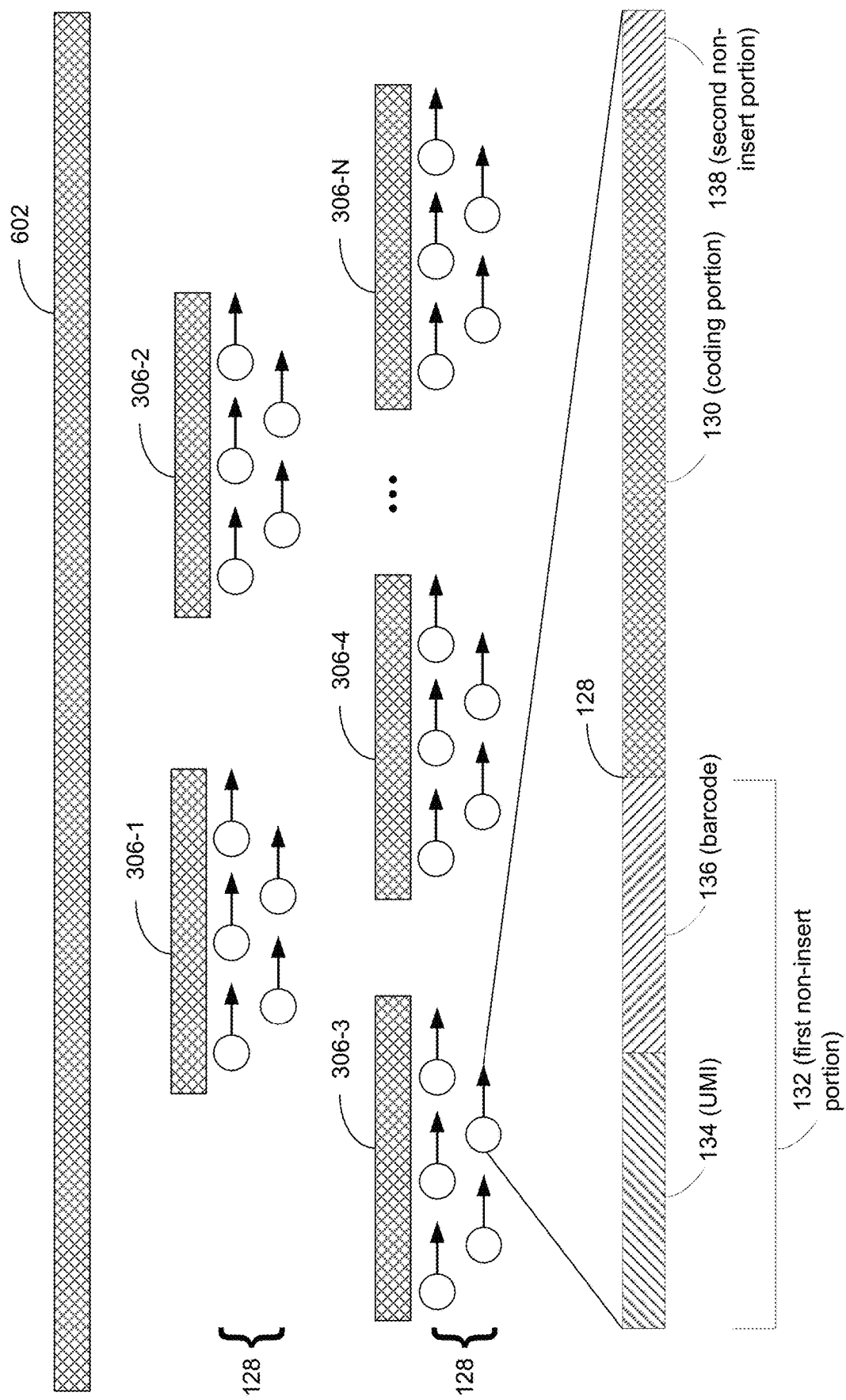
FIG. 4 illustrates the relationship between a test nucleic acid (e.g., chromosomal DNA), the different fragments of a larger test nucleic acid, and sequence reads of fragments in accordance with some embodiments of the present disclosure.

Obtaining a plurality of sequence reads. In accordance with the disclosed systems and methods, a plurality of sequence reads 128 is obtained (205), in electronic form. Such sequence reads form the basis of a multiplexed sequencing reaction dataset 126. Referring to FIG. 4, each respective sequence read 128 in the plurality of sequence reads comprises a corresponding insert (e.g., coding) portion 130, a corresponding first non-insert portion 132 consisting of N nucleotide positions, and a corresponding second non-insert portion 138 consisting of M nucleotide positions. N and M are positive integers. Each corresponding first non-insert portion 132 represents an identifier of a unique molecule (e.g., a unique molecular identifier) 134. Each corresponding second non-insert portion 138 comprises a sample index.

Figure 5A:
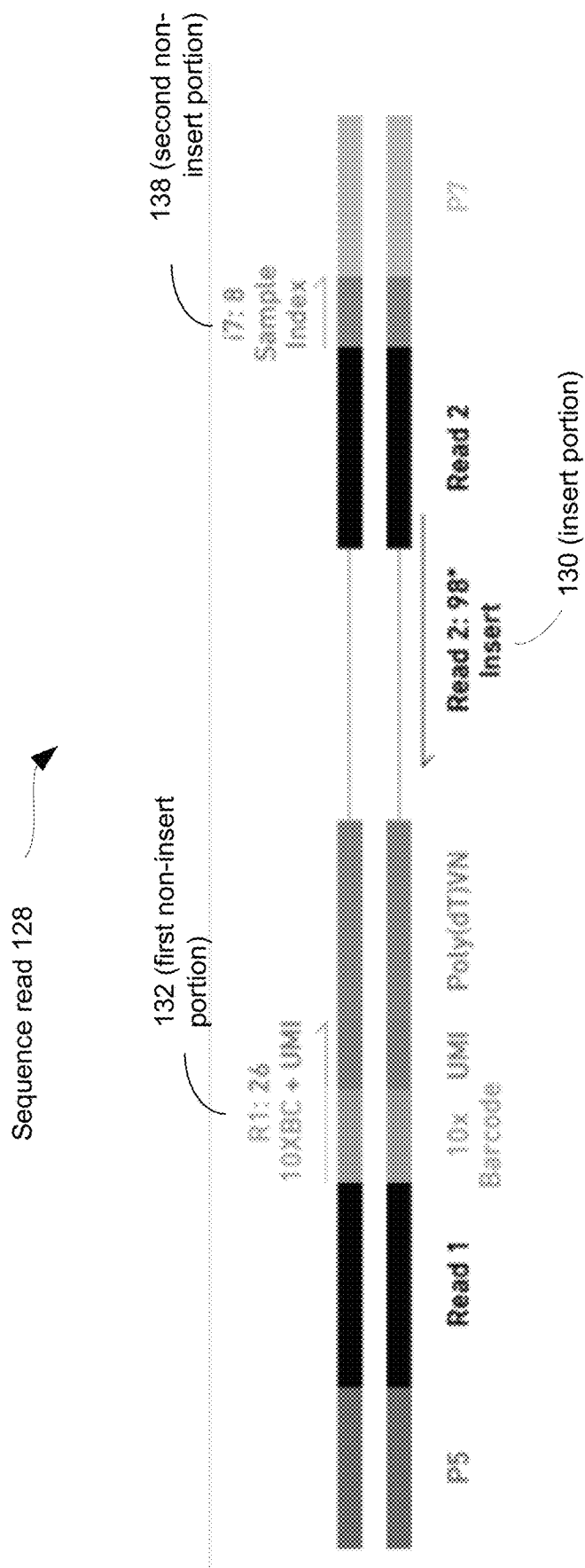
FIG. 5A illustrates the format of a scRNA-seq sequence read in a BAM file in accordance with some embodiments of the present disclosure.

In some embodiments, referring to FIG. 5A, the first 26-28 base-pairs (bp) of the first non-insert portion is all or a portion of the sequence read termed "read 1," or "R1," and it contains a 10× (Pleasanton, California) barcode 136 that is 16 bp in length and a unique UMI 134 that is 10-12 base-pairs (e.g., for 10× Immune Profiling and Gene Expression libraries). In some scRNA-seq embodiments, the first non-insert portion is the first 26-28 base-pairs (bp) of read1, which contain a 10× barcode (16 bp) and a unique molecular identifier (10-12 bp) (e.g., for 10× Immune Profiling and Gene Expression libraries). In such embodiments, the 10× barcode and unique molecular identifier constitute 52-56 bits of molecule-identifying information divorced from any underlying biology. In some embodiments the sequence reads 128 are in a BAM file. Example 2 provides a non-limiting example of the fields of a BAM file in accordance with some embodiments of the present disclosure.

Figure 5B:
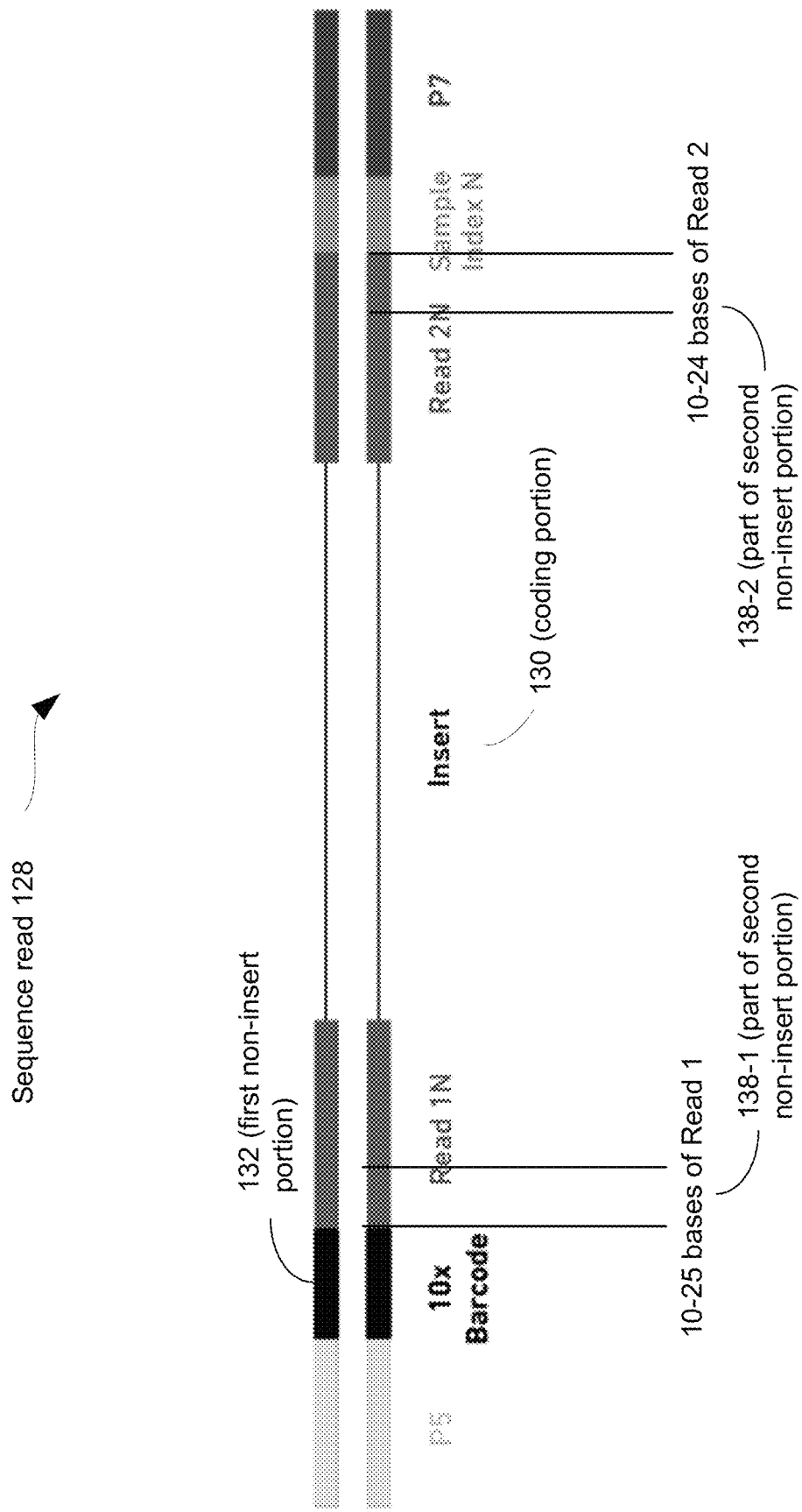
FIG. 5B illustrates the format of a scATAC-seq sequence read in accordance with some embodiments of the present disclosure.

Referring to FIG. 5B, in the context of single cell Assay for Transposase-Accessible Chromatin (scATAC-seq), the sequence reads do not have a unique molecular identifier in some embodiments. ATAC-seq is further described in WO14189957 and WO18218226, the full disclosures of which is hereby incorporated by reference in their entireties. Such sequence reads have a cellular barcode (16 base pairs) (10× Barcode), that is contained in the index2 read of the read-pair. Without a unique molecular identifier within the construct, other means are needed to assign each sequence read to a unique molecule (e.g., nucleic acid present in a sequenced sample). In some embodiments in which the sequence reads do not have a unique molecule identifier, such as some forms of scATAC-seq sequence reads, a proxy for the unique molecule identifier is created from various non-insert sequence information in the scATAC-seq read-pair. For instance, in some embodiments, the first non-insert portion that represents an identifier of a unique molecule is formed from bases 10-25 of read1 and bases 10-24 of read2 of the scATAC-seq read-pair. Use of the 10 bp downstream of the start advantageously avoids bias due to any preferential activity of the Tn5 transposase employed by the ATAC-seq assay. As such, sequence data is taken from both read1 and read2 to build a novel "29-mer" (the first non-insert portion of the sequence read) in such embodiments that is unlikely to be repeated by nature (in the context of the usual organisms for which the assay is often used: humans and mice). In some embodiments, the first non-insert portion that represents an identifier of the unique acid molecule comprises the above-described novel "29-mer" in combination with the 16 base pair barcode on the index2 read, which thus represents 90 bits of molecule-identifying information that is sufficiently divorced from any underlying biology.

In some embodiments, the plurality of sequence reads includes one or more first sequence reads from a first sample that each have a first value for the sample index. In some embodiments, the plurality of sequence reads include one or more second sequence reads from a second sample that each have a second value for the sample index. In practice, the plurality of sequence reads includes sequence reads from a number of (e.g., 2 or more, 5 or more, 10 or more, 20 or more, 50 or more, 100 or more, or 200 or more) different samples.

In some embodiments, the multiplexed sequencing reaction is a duplex sequencing reaction (206). For instance, in some embodiments the sequence reaction is a scRNA-seq (see e.g., Denisenko et al., 2019, "Systematic assessment of tissue dissociation and storage biases in single-cell and single-nucleus RNA-seq workflows," bioRxiv preprint doi: https://doi.org/10.1101/832444; this version posted Dec. 30, 2019) or an scATAC-seq reaction (see e.g., Giansanti, 2020, "Fast analysis of scATAC-seq data using a predefined set of genomic regions," F1000Research 9, 199). In some embodiments, the multiplexed sequencing reaction is a single-strand consequence sequencing reaction. In some embodiments, the multiplexed sequencing reaction includes a paired-end sequencing reaction, a whole-genome next generation sequencing reaction, an exome next generation sequencing reaction, a de novo next generation sequencing reaction, a targeted sequencing reaction, or a transcriptomics sequence reaction (e.g., total RNA, total mRNA, or targeted RNA sequencing). See, for example, the Internet at illumina.com/content/dam/illumina-marketing/documents/products/illumina_sequencing_intr oduction.pdf, last accessed Feb. 1, 2020, "An introduction to Next-Generation Sequencing Technology," which is hereby incorporated by reference.

In some embodiments, the plurality of sequence reads is obtained by loading test nucleic acid onto a plurality of gel bead-in emulsions beads (block 207). In some embodiments, the plurality of gel bead-in emulsion beads comprises ten or more beads, 100 or more beads, 1000 or more beads, 10,000 or more beads, 100,000 or more beads, $1 \times 10^6$ or more beads or $1 \times 10^7$ or more beads. Example 1 provides details of an example way in which such sequence reads are acquired using partitions, such as gel bead-in emulsions beads, in accordance with some embodiments of the present disclosure.

In some embodiments, sequence reads of the present disclosure are obtained using the techniques disclosed in United States Patent Publication No. 20180312873, entitled "Method and Systems for High Throughput Single Cell Genetic Manipulation," filed Oct. 17, 2016, which is hereby incorporated by reference.

In some embodiments, the plurality of sequence reads is from more than five different biological samples and comprises more than one hundred thousand sequence reads (208). That is, in some embodiments, the multiplexed sequencing reaction dataset 126 comprises a first set of sequence reads that each include a first sample index value in their second non-insert portion, a second set of sequence reads that each include a second sample index value in their second non-insert portion, a third set of sequence reads that each include a third sample index value in their second non-insert portion, a fourth set of sequence reads that each include a fourth sample index value in their second non-insert portion, and a fifth set of sequence reads that each include a fifth sample index value in their second non-insert portion, where the first, second, third, fourth and fifth index value are each different. In this example, the first, second, third, fourth, and fifth, sets of sequence reads originated from different biological samples from different subjects.

In some embodiments, the plurality of sequence reads is from more than five, ten, fifteen, twenty, or fifty different biological samples and comprises more than one hundred thousand, one million, ten million, or one hundred million sequence reads. In some embodiments, the plurality of sequence reads collectively includes more than five, ten, fifteen, twenty, or fifty different sample index values and comprises more than one hundred thousand, one million, ten million, or one hundred million sequence reads.

Figure 2A:
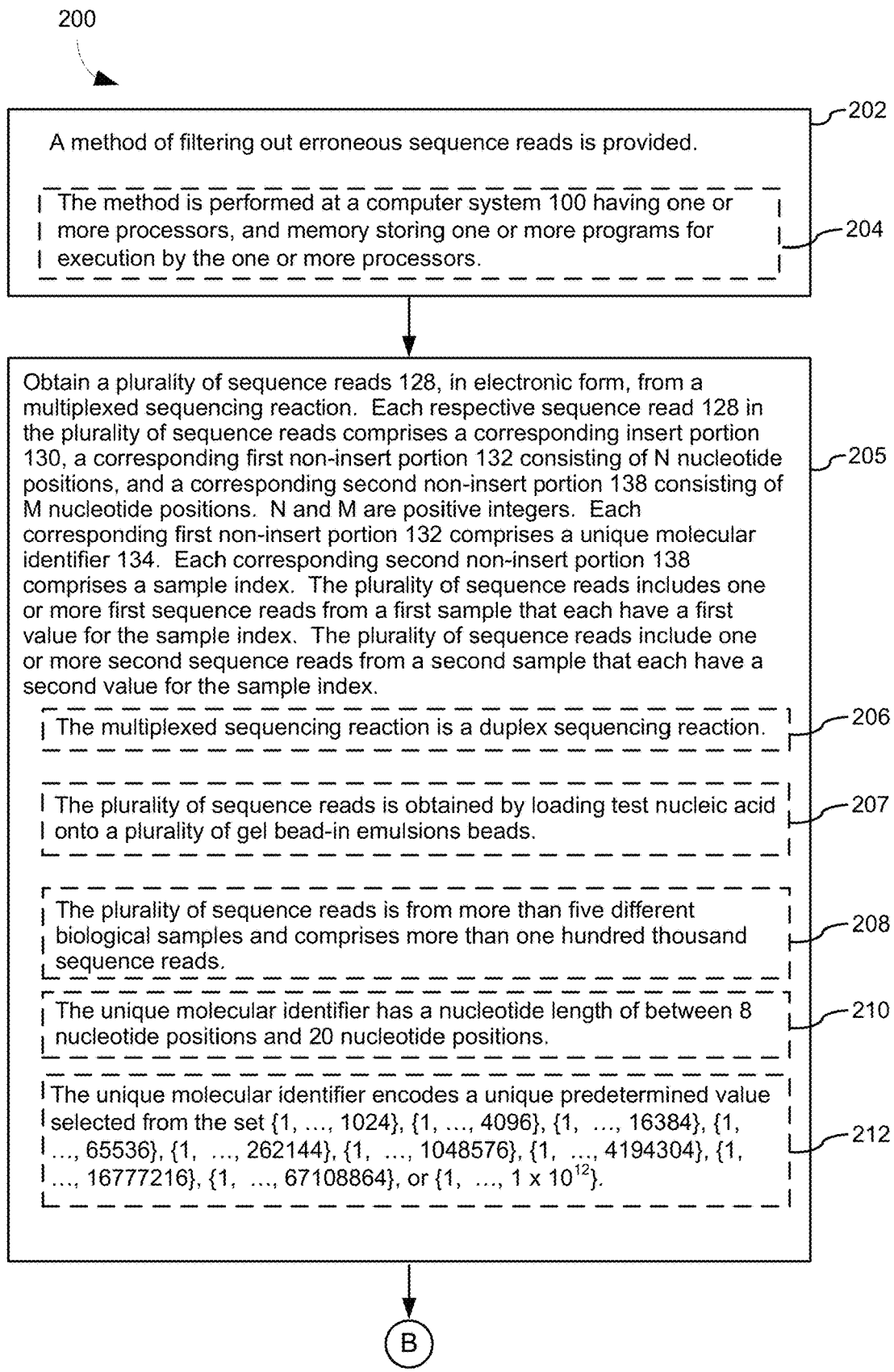

Referring to block 212 of FIG. 2A, in some embodiments, the identifier of the unique molecule (e.g., UMI) of the first non-insert portion 132 of a respective sequence read 128 has a nucleotide length of between 8 nucleotide positions and 14 nucleotide positions. In some embodiments, the UMI in the first non-insert portion 132 of each respective sequence read in the plurality of sequence reads encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$. For instance, consider the case in which the UMI sequence is represented by a set of five nucleotide positions. In this instance, each nucleotide position contributes four possibilities (A, T, C or G), giving rise, when all five positions are considered, to 4×4×4×4×4=1024 possibilities. As such, the five nucleotide positions form the basis of the set $\{1, \ldots, 1024\}$. In other words, when the UMI sequence 134 is a 5-mer, the first non-insert portion 132 of each sequence read 128 encodes a UMI with a unique predetermined value selected from the set $\{1, \ldots, 1024\}$. Likewise, when the UMI sequence 134 is represented by a set of six nucleotide positions, the six nucleotide positions collectively contribute 4×4×4×4×4×4=4096 possibilities. As such, the six nucleotide positions form the basis of the set $\{1, \ldots, 4096\}$. In other words, when the UMI sequence 132 is a 6-mer, the first non-insert portion 132 of each sequence read 128 encodes a UMI with a unique predetermined value selected from the set $\{1, \ldots, 4096\}$.

In some embodiments, the UMI in the first non-insert portion 132 of a sequence read 128 in the plurality of sequence reads is localized to a contiguous set of oligonucleotides within the sequence read. In one such exemplary embodiment, the contiguous set of oligonucleotides is a K-mer, where K is an integer selected from the set $\{8, \ldots, 500\}$, $\{8, \ldots, 400\}$, $\{8, \ldots, 300\}$, $\{8, \ldots, 200\}$, $\{8, \ldots, 100\}$, $\{8, \ldots, 50\}$, $\{8, \ldots, 40\}$, $\{8, \ldots, 30\}$, or $\{8, \ldots, 14\}$. In other words, in some embodiments, the UMI is a contiguous set of nucleotide positions (e.g., 8 contiguous nucleotide positions, 9 contiguous nucleotide positions, 10 contiguous nucleotide positions, 11 contiguous nucleotide positions, 12 contiguous nucleotide positions, 13 contiguous nucleotide positions, or 14 contiguous nucleotide positions) in the first non-insert portion 132 of the sequence read 128.

In some embodiments, the UMI in the first non-insert portion 132 of a sequence read 128 in the plurality of sequence reads is localized to two, three, four, five, six or more different contiguous sets of oligonucleotides within the sequence read. In one such exemplary embodiment, each contiguous set of oligonucleotides contributes to an overall K-mer, where K is an integer selected from the set $\{8, \ldots, 500\}$, $\{8, \ldots, 400\}$, $\{8, \ldots, 300\}$, $\{8, \ldots, 200\}$, $\{8, \ldots, 100\}$, $\{8, \ldots, 50\}$, $\{8, \ldots, 40\}$, $\{8, \ldots, 30\}$, or $\{8, \ldots, 14\}$. In other words, in some embodiments, the UMI is a collection of contiguous sets of nucleotide positions (e.g., where each respective contiguous set in the collection of contiguous sets of nucleotide positions is 8 contiguous nucleotide positions, 9 contiguous nucleotide positions, 10 contiguous nucleotide positions, 11 contiguous nucleotide positions, 12 contiguous nucleotide positions, 13 contiguous nucleotide positions, or 14 contiguous nucleotide positions from a corresponding predetermined portion of the sequence read) in the first non-insert portion 132 of the sequence read 128.

In some embodiments, the UMI in the first non-insert portion 134 of a sequence read in the plurality of sequence reads is localized to a noncontiguous set of oligonucleotides within the sequence read. In one such exemplary embodiment, the predetermined noncontiguous set of nucleotides collectively consists of K nucleotides, where K is an integer in the set $\{8, \ldots, 14\}$, $\{8, \ldots, 15\}$, $\{8, \ldots, 16\}$, $\{8, \ldots, 17\}$, $\{8, \ldots, 18\}$, $\{8, \ldots, 19\}$, $\{8, \ldots, 20\}$, $\{8, \ldots, 21\}$, $\{8, \ldots, 22\}$, $\{8, \ldots, 23\}$, $\{7, \ldots, 24\}$, $\{6, \ldots, 25\}$, or $\{5, \ldots, 26\}$, $\{8, \ldots, 500\}$, $\{8, \ldots, 400\}$, $\{8, \ldots, 300\}$, $\{8, \ldots, 200\}$, $\{8, \ldots, 100\}$, $\{8, \ldots, 50\}$, $\{8, \ldots, 40\}$, or $\{8, \ldots, 30\}$. As an example, in some embodiments, the UMI comprises a first set of contiguous nucleotide positions at a first position in the sequence read and a second set of contiguous nucleotide positions at a second position in the sequence read, that is displaced from the first set of contiguous nucleotide positions by a spacer. In one specific example, the barcode sequence 132 comprises $(X1)_a Y_z (X2)_b$, where X1 is a contiguous nucleotide positions, Y is a constant predetermined set of z contiguous nucleotide positions, and X2 is b contiguous nucleotide positions. In this example, the UMI produced by a schema invoking this exemplary barcode is localized to a noncontiguous set of oligonucleotides, namely $(X1)_a$ and $(X2)_b$. This is just one of many examples of noncontiguous formats for the UMI.

In some embodiments, a respective sequence read in the plurality of sequence reads corresponds to a subset of the test nucleic acid that is 2×36 bp, 2×50 bp, 2×76 bp, 2×98 bp, 2×100 bp, 2×150 bp 2×250 bp, 2×300 bp or 2×350 bp where the terminology 2×Q bp means that the sequence read has two reads of length Q base pairs from a single source nucleic acid (e.g., from a test nucleic acid obtained from a biological sample) that are separated by an unspecified length. In some embodiments this unspecified length is between 200 to 1200 base pairs. In some embodiments, a respective sequence read in the plurality of sequence reads represents at least 25 bp, at least 30 bp, at least 50 bp, between 90 and 100 bp, 98 bp, at least 100 bp, at least 200 bp, at least 250 bp, at least 500 bp, less than 500 bp, less than 400 bp, or less than 300 bp of a single piece of nucleic acid (e.g., from a test nucleic acid obtained from the nucleic acid of a biological sample, such as a cDNA).

The first non-insert portion 132 and the second non-insert portion 138 is independent of the sequencing data of the test nucleic acid being sequenced. In other words, first non-insert portion 132 and the second non-insert portion 138 is not derived from, or a function of the sequencing data of the test nucleic acid being sequenced.

In some embodiments, a first sequence read in the plurality of sequence reads corresponds to a subset of the test nucleic acid that is 2×36 bp, 2×50 bp, 2×76 bp, 2×98 bp, 2×100 bp, 2×150 bp, 2×250 bp, 2×300 bp or 2×350 bp where the terminology 2×N bp means that the sequence read has two reads that encode a length of N base pairs from a single piece of nucleic acid (e.g., from a test nucleic acid obtained from a biological sample) that are separated by an unspecified length. In some embodiments this unspecified length is between 200 to 1200 base pairs, or between 100 and 2500 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a test nucleic acid obtained from a biological sample).

In some embodiments, as illustrated in FIG. 4, to obtain the plurality of sequence reads 128, a larger contiguous nucleic acid 602 (the test nucleic acid, e.g., chromosomal DNA, mRNA, etc.) is fragmented to form fragments 306 and these fragments are compartmentalized, or partitioned into discrete compartments or partitions (referred to interchangeably herein as partitions). In some embodiments, the sequence reads 128 are obtained from mRNA or total RNA that is not fragmented. In such embodiments there is no larger contiguous nucleic acid 602 that is sequenced and each fragment 306 represents a discrete RNA molecule found in a cell sample that is sequenced. In some embodiments, the test nucleic acid 602 is the genome of a multi-chromosomal organism such as a human. In some embodiments, more than 10, more than 100, more than 1000, more than 10,000, more than 100,000, more than $1 \times 10^6$, or more than $5 \times 10^6$ sets of sequence reads are obtained, corresponding to more than 10, more than 100, more than 1000, more than 10,000, more than 100,000, more than $1 \times 10^6$, or more than $5 \times 10^6$ partitions. FIG. 4 thus illustrates the relationship between the larger contiguous nucleic acid 602, the different fragments 306 of the larger contiguous nucleic acid, and sequence reads 128 of fragments in some embodiments. Typically, between 1 and 250 fragments 306, between 5 and 500 fragments 306 or between 10 and 1000 fragments 306 are each partitioned into a separate partition. In any event, sufficiently few of the fragments 306 are partitioned into the same partition such that the chance that the fragments 306 in a single partition have any appreciable overlapping sequences is unlikely. Sequence reads 128 of each fragment 306 are made. In typical embodiments, sequence reads 128 are short in length (e.g., less than 1000 bases) so that they can be sequenced in automated sequencers. In some embodiments, each sequence read 128 in a partition includes a common barcode that is independent of the sequence of the larger contiguous nucleic 602 acid nucleic acid and that identifies the partition, in a plurality of partitions, in which the respective sequence read was formed.

In some embodiments, a test nucleic acid (the nucleic acid that is being sequenced) is all or a portion of the genome of a multi-chromosomal organism such as a human. In some embodiments, a test nucleic acid (the nucleic acid that is being sequenced) is all or a portion of a chromosome, or a plurality of chromosomes of a multi-chromosomal organism such as a human. In some embodiments, the biological sample is from a multi-chromosomal species and the test nucleic acid comprises a plurality of nucleic acids collectively representing at least 10 percent, at least 20 percent, at least 30 percent, at least 40 percent, at least 50 percent, at least 60 percent or at least 70 percent of a plurality of chromosomes (e.g., two or more, three or more, four or more, five or more, six or more, seven or more, eight or more, nine or more, or 10 or more chromosomes) from the multi-chromosomal species.

Figure 2B:
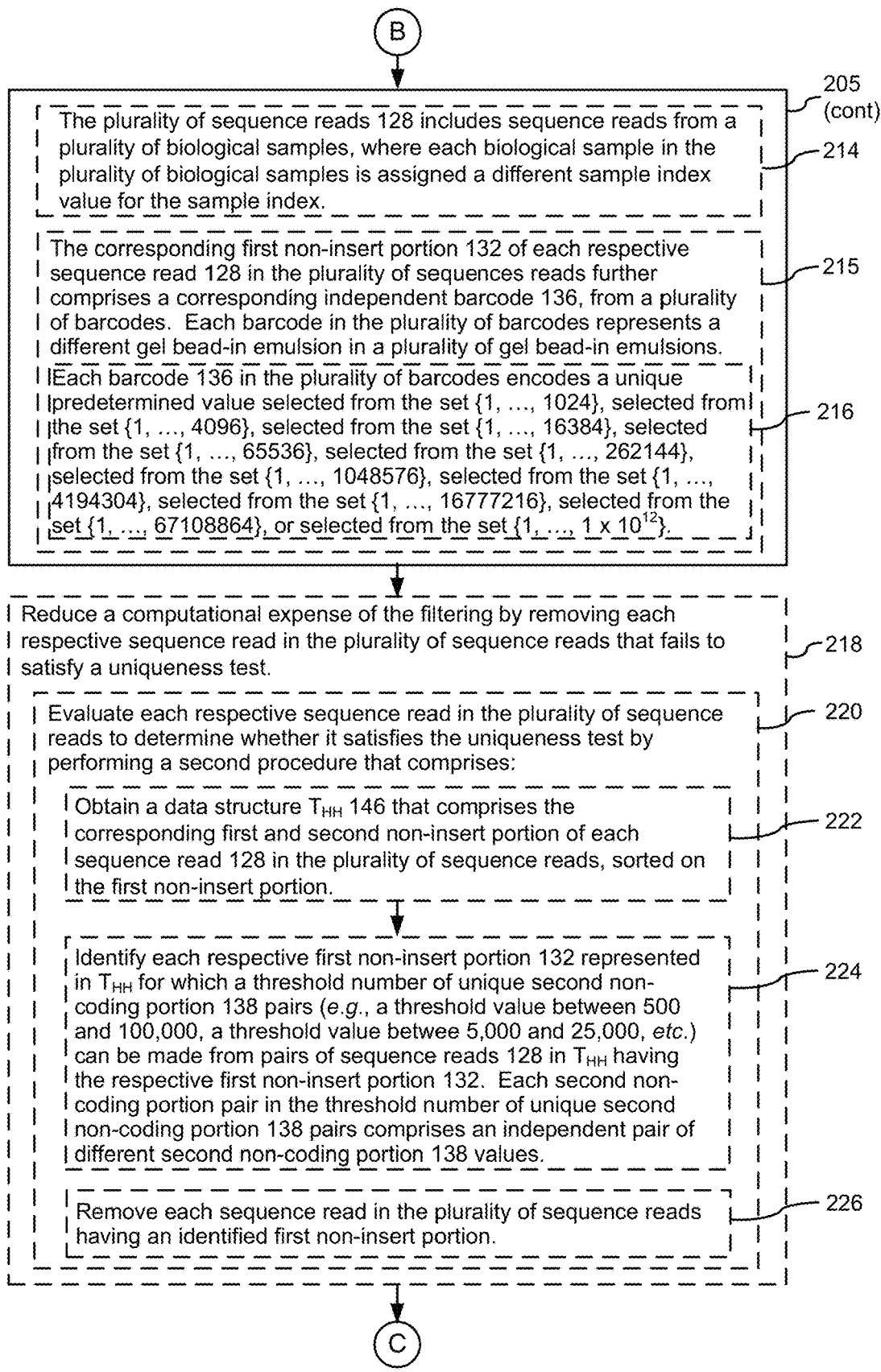

Referring to block 214 of FIG. 2B, in some embodiments, the plurality of sequence reads 128 includes sequence reads from a plurality of biological samples, where each biological sample in the plurality of biological samples is assigned a different sample index value for the sample index. In some such embodiments, each of the biological samples is from a different subject. In some such embodiments, each of the biological samples is from a different subject and the plurality of biological samples comprises 2, 3, 4, 5, 6, 7, 8, 9, 10, 11, 12, 13, 14, 15, 16, 17, 18, 19, 20, 21, 22, 23, 24, 25, 30, 35, 40, 50, 55, 60, 65, 70, 75, 80, 85, 90, 95, 100, 200, 300, 400, or 500 or more biological samples, each from a different subject. In some embodiments, 2, 3, 4, 5, 6, 7, or 8 of the biological samples are from the same subject.

Referring to block 215 of FIG. 2B, in some embodiments, the corresponding first non-insert portion 132 of each respective sequence read 128 in the plurality of sequence reads further comprises a corresponding independent barcode 136, from a plurality of barcodes. Each barcode in the plurality of barcodes represents a different gel bead-in emulsion in a plurality of gel bead-in emulsions.

Referring to block 216 of FIG. 2B, in some embodiments, each barcode 136 in the plurality of barcodes encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1 \times 10^{12}\}$.

In some embodiments, the corresponding first non-insert portion 132 of each respective sequence read 128 in the plurality of sequence reads represents an identifier of a unique molecule (e.g., UMI) 134 and a corresponding independent barcode 136, where the UMI is positioned before the barcode. In some alternative embodiments, the corresponding first non-insert portion 132 of each respective sequence read 128 in the plurality of sequence reads comprises a unique molecular identifier (UMI) 134 and a corresponding independent barcode 136, where the UMI is positioned after the barcode.

In some embodiments, the corresponding first non-insert portion 132 of each respective sequence read 128 in the plurality of sequence reads comprises (i) between 1-100 predetermined non-insert positions of the sequence read that serves as a proxy (substitute) to an identifier of a unique molecule (e.g., UMI) 134 and (ii) a corresponding independent barcode 136.

Referring to block 218 of FIG. 2B, in some embodiments, a computational expense of the disclosed filtering processes is reduced. In some such embodiments, this is accomplished by removing some sequence reads from the multiplexed sequencing reaction dataset 126 that have a high likelihood of being index swapped. For instance, in some embodiments a uniqueness test is applied to each sequence read, and those sequence reads that fail to satisfy the uniqueness test are removed from the multiplexed sequencing reaction dataset 126. Much computational expense is saved by removing some sequence reads from the sequencing reaction dataset 126. This is because the identification of sequence read pairs that have the same hash value but different second non-insert portions in various hash tables as described below in conjunction with block 246, requires comparisons of the sequence reads that potentially run in quadratic-time as a function of the number of sequence reads to be evaluated. This computational expense is described in further detail below in conjunction with block 246 of FIG. 2D.

Blocks 220 through 226 of FIG. 2B outline one nonlimiting example of a uniqueness test. Referring to block 220 of FIG. 2B, in some such embodiments, each respective sequence read in the plurality of sequence reads is evaluated to determine whether it satisfies the uniqueness test by performing the procedure of blocks 222 through 226 on the respective sequence read. Referring to block 222 of FIG. 2B, a table $T_{HH}$ 146 that comprises the corresponding first and second non-insert portion of each sequence read 128 in the plurality of sequence reads, sorted on the first non-insert portion, is obtained.

Figure 1C:
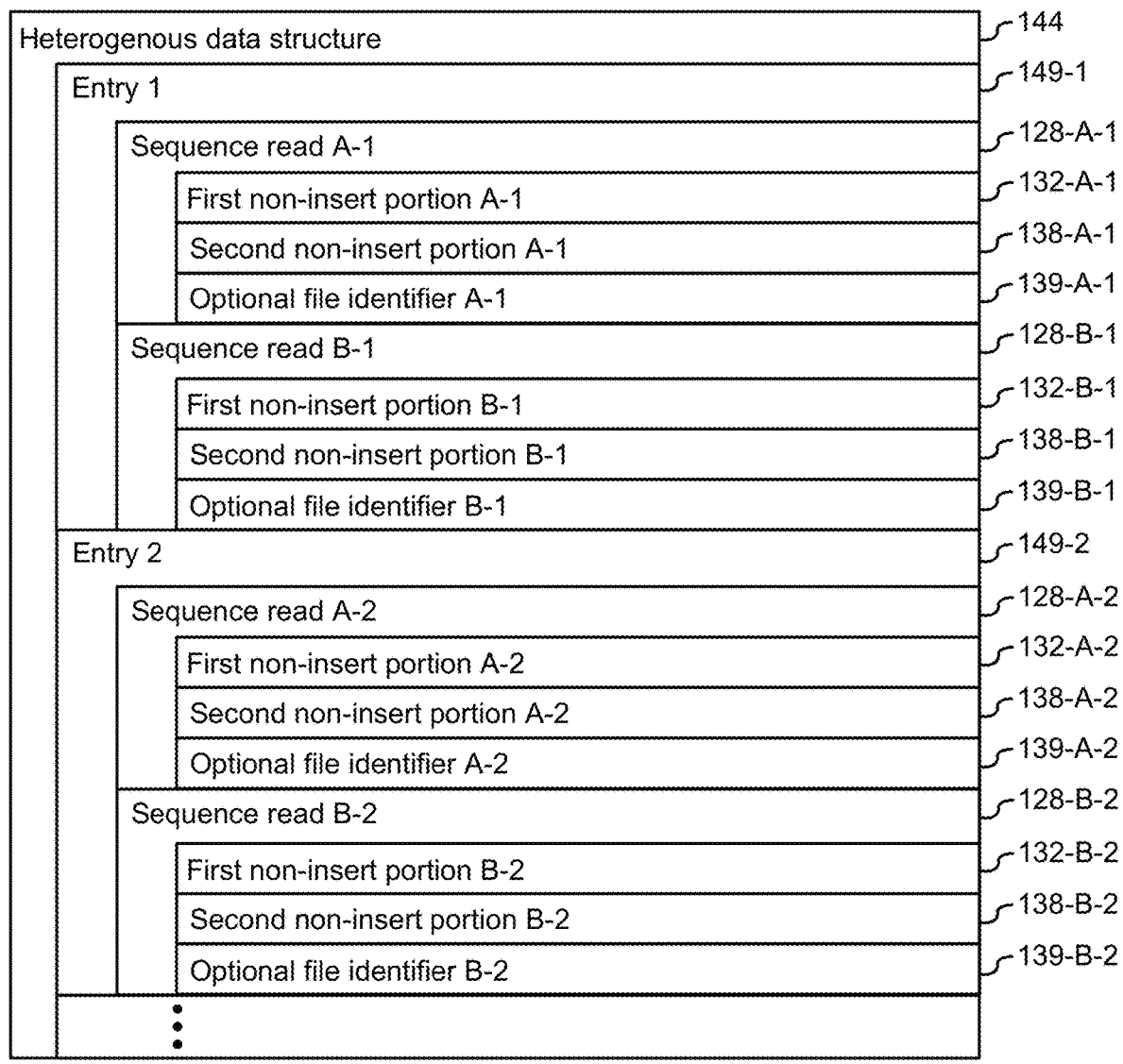
Figure 1D:
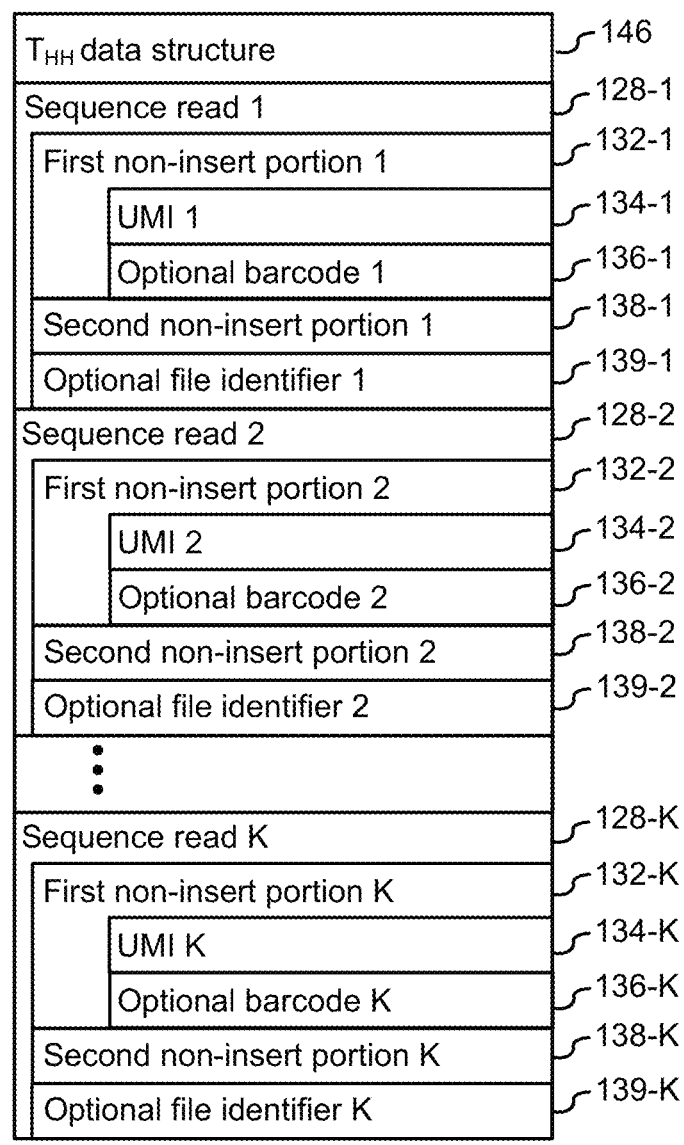

A $T_{HH}$ data structure 146 is illustrated in FIG. 1D. The $T_{HH}$ data structure includes, for each sequence read 128 in the multiplexed sequencing reaction dataset 126, specific elements of the sequence read: the first non-insert portion 132 (e.g., the barcode and UMI or proxy for the UMI in instances where the sequence reads do not have a UMI), the seconding non-insert portion 138 (e.g., the sample index), and optionally the file identifier 139 of the respective sequence read 128. As such, the $T_{HH}$ data structure contains just specific elements of the sequence read data, as opposed to the full set of data that is associated with each sequence read in the multiplexed sequencing reaction dataset 126. As noted in Example 2 below, the information in the full set of data that is associated with each sequence read in some embodiments includes numerous other fields that are not contained in the $T_{HH}$ data structure. Moreover, the information for the sequence reads in the $T_{HH}$ data structure are specifically lexicographically sorted on the first non-insert portions 132.

Referring to block 224, each respective first non-insert portion 132 represented in $T_{HH}$ is identified for which a threshold number of unique second non-coding portion 138 pairs (e.g., a threshold value between 500 and 100,000, a threshold value between 5,000 and 25,000, etc.) can be made from pairs of sequence reads 128 in $T_{HH}$ having the respective first non-insert portion 132. Each second non-coding portion pair in the threshold number of unique second non-coding portion 138 pairs comprises an independent pair of different second non-coding portion 138 values. For instance, consider the case where a first sequence read represented in $T_{HH}$ has a first non-insert portion 132 "A", where "A" represents a specific 26 base pair long sequence. The question is then asked, how many different sequence reads that each have the same first non-insert portion 132 "A" but a different second non-insert portion 138 represented in $T_{HH}$ may this first sequence read be paired with. If there are more than the threshold number of such pairs in $T_{HH}$, then the first sequence read is flagged for removal from the multiplexed sequencing reaction dataset 126.

Note that it is, of course, not necessary to create the $T_{HH}$ data structure in order to perform the evaluation of block 224. Moreover, it is not necessary to sort sequence reads in the $T_{HH}$ data structure to perform the evaluation of block 224 either. However, it will be appreciated that typical multiplexed sequencing reaction datasets 126 include hundreds of thousands, millions, or even billions of sequence reads. Thus, using the multiplexed sequencing reaction dataset 126 on such large data sets, or even a $T_{HH}$ data structure that has not been lexicographically sorted on the first non-insert portion 132 to identify the number of pairings for each sequence read, in accordance with block 224, would require much more computational expense. Thus, although the $T_{HH}$ data structure is not strictly required, it is used in preferred embodiments of the disclosed implementation of the procedure set forth in blocks 220 through 226 given the large number of sequence reads that are typically in the multiplexed sequencing reaction dataset 126.

Referring to block 226 of FIG. 2B, each sequence read in the plurality of sequence reads having an identified first non-insert portion is removed. In other words, each sequence read that has a first non-insert portion that included in the $T_{HH}$ data structure more than the threshold number of unique combinations of the second non-insert portion, as identified in block 226, are removed from the multiplexed sequencing reaction dataset 126.

In some embodiments, the threshold is used, and for each respective first non-insert portion 132 that appears in more than one sequence read $T_{HH}$ (and thus indicates at least two different second non-insert portions 138 and thus at least two different sample identifiers for the same first non-insert portion) but whose corresponding sequence reads have not been removed by operation of blocks 222 through 226, an attempt is made to keep the sequence reads having the most prevalent second non-insert portion (sample identifier). Those sequence reads that do not have the most prevalent second non-insert portion are removed from $T_{HH}$ and thus removed from the multiplexed sequencing reaction dataset 126. A statistical test is run to determine whether there is enough confidence to keep the sequence reads with the most prevalent second non-insert portion value. If this statistical test fails to establish sufficient confidence in the sequence reads with the most prevalent second non-insert portion, these sequence reads are also removed from $T_{HH}$ and thus removed from the multiplexed sequencing reaction dataset 126.

For example, consider the case where there are five sequence reads that all have the first non-insert portion 132 of value "A," where A is a particular 27 base pair string, and that three of the sequence reads have a value of "B" for the second non-insert portion while two have the value "C" for the second non-insert portion. Here, B and C are two different sequences for the second non-insert portion. As such, they are not removed from the multiplexed sequencing reaction dataset 126 by operation of blocks 218 through 226, because they are unable to form a threshold number of pairs in accordance with block 224. So, here, a check is performed to see if there enough statistical confidence in the three sequence reads having the value "B" to keep them in $T_{HH}$ and thus in the multiplexed sequencing reaction dataset 126. The two sequence reads with the value "C" will be removed $T_{HH}$ and thus in the multiplexed sequencing reaction dataset 126 regardless of the outcome of the statistical test. In some embodiments, the check is done by performing a statistical test between the greatest and second greatest counts of the second non-insert portion among the sequence reads that have the same first non-insert portion.

In some embodiments, this statistical test is a determination as to whether the cumulative distribution function at 10% of Beta($\alpha$ is the second greatest count+2.4, $\beta$ is the greatest count+2.4) is greater than 0.01. If it is, the sequence reads with the most prevalent second non-insert portion are retained and all other sequence reads for a given first non-insert portion are removed. In other words, a determination of whether betacdf($x$, $\alpha$, $\beta$) is greater than 0.01, where x is 0.10, a is the count of sequence reads that have the second most common second non-insert portion value for the subject first non-insert portion plus 2.4, $\beta$ is the count of sequence reads that have the most common second non-insert portion for the subject first non-insert portion plus 2.4, and betacdf is the beta cumulative distribution function of 0.10, $\alpha$, $\beta$. In the example above, where there are five sequence reads that all have the first non-insert portion 132 of value "A," where A is a particular 27 base pair string, and that three of the sequence reads have a value of "B" for the second non-insert portion while two have the value "C" for the second non-insert portion the computation is:

$$\text{betacdf}(x, \alpha, \beta) = \text{betacdf}(0.10, (2+2.4), (3+2.4)) = 0.003.$$

Because the betacdf value is not greater than 0.01, all five sequence reads are removed from $T_{HH}$ and thus from the multiplexed sequencing reaction dataset 126. The value 2.4 Was chosen so that counts (1, 1), with betacdf(0.10, (1+2.4), (1+2.4))=0.0054 which is less than 0.01, and (2, 1), with betacdf(0.10, (1+2.4), (2+2.4))=0.00997 which is less than 0.01, would cause rejection of all the sequence reads, but count (3, 1), betacdf(0.10, (1+2.4), (3+2.4))=0.016 which is greater than 0.01, would allow the sequence reads having the most common second non-insert portion to be retained.

In some embodiments, the statistical test is a determination as to whether the cumulative distribution function at 10% of Beta($\alpha$ is the second greatest count+2.4, $\beta$ is the greatest count+2.4) is greater than 0.001, greater than 0.02, 0.05, or greater than 0.10.

In some embodiments, the statistical test is a determination as to whether the cumulative distribution function at 10% of Beta($\alpha$ is the second greatest count+delta, $\beta$ is the greatest count+delta) is greater than 0.001, greater than 0.02, greater than 0.01, 0.05, or greater than 0.10, where delta is a predetermined value between zero and 5 e.g., 2.4).

In some embodiments, the statistical test is a determination as to whether the cumulative distribution function at a predetermined percentage of Beta($\alpha$ is the second greatest count+delta, $\beta$ is the greatest count+delta) is greater than 0.001, greater than 0.02, greater than 0.01, 0.05, or greater than 0.10, where delta is a predetermined value between zero and 5, e.g., 2.4), and where the predetermined percentage is between two percent and twenty-five percent (e.g., 2 percent, five percent, ten percent, 15 percent, 20 percent, or 25 percent).

In some embodiments, the statistical test is a kernel density estimate, a cumulative distribution function, a probability mass function, or a histogram. See, for example, 2020, Grami, *Probability, Random Variables, Statistics, and Random Processes: Fundamentals & Applications* 1st Edition, John Wiley & Sons Inc., which is hereby incorporated by reference.

Figure 2D:
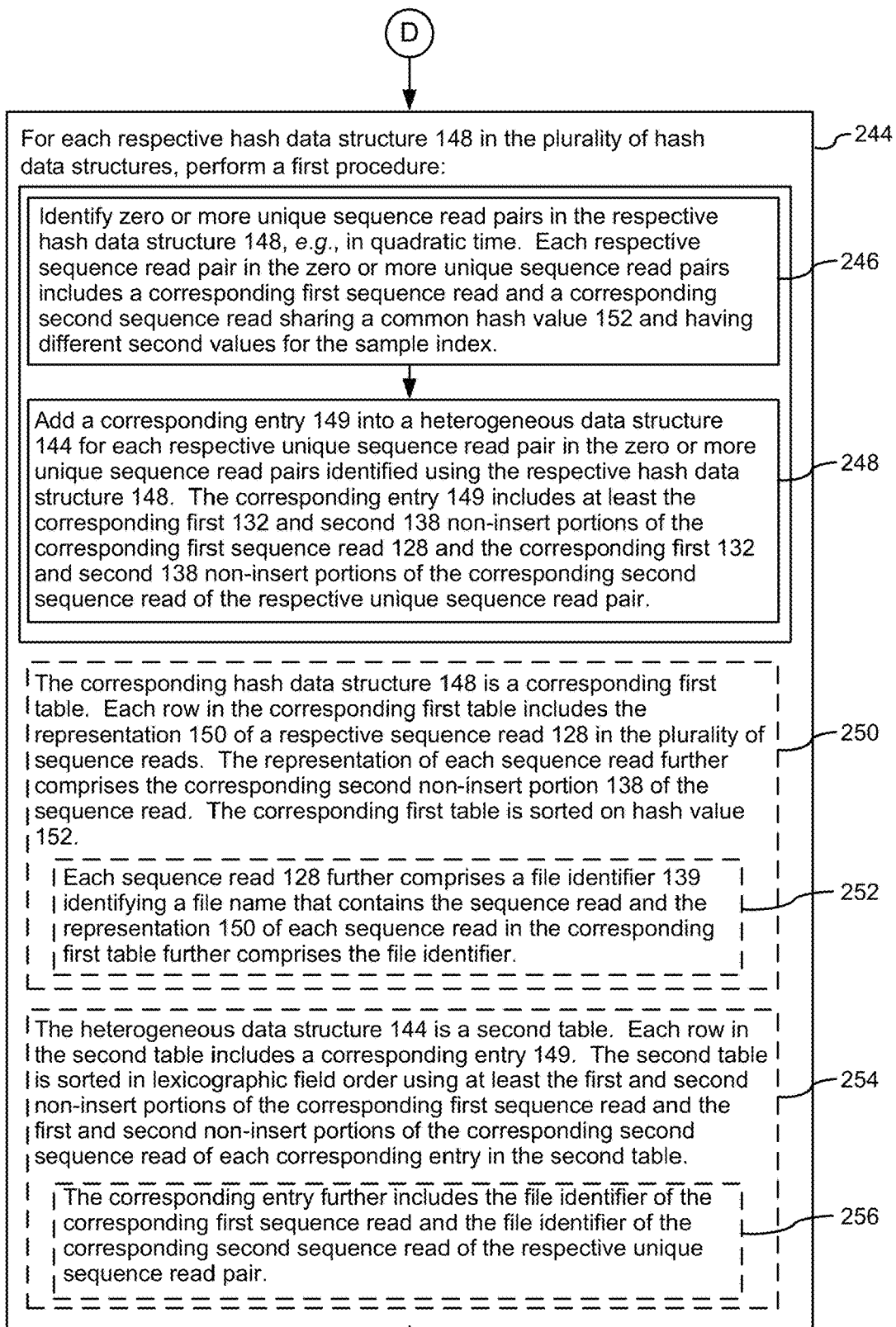
Figure 2E:
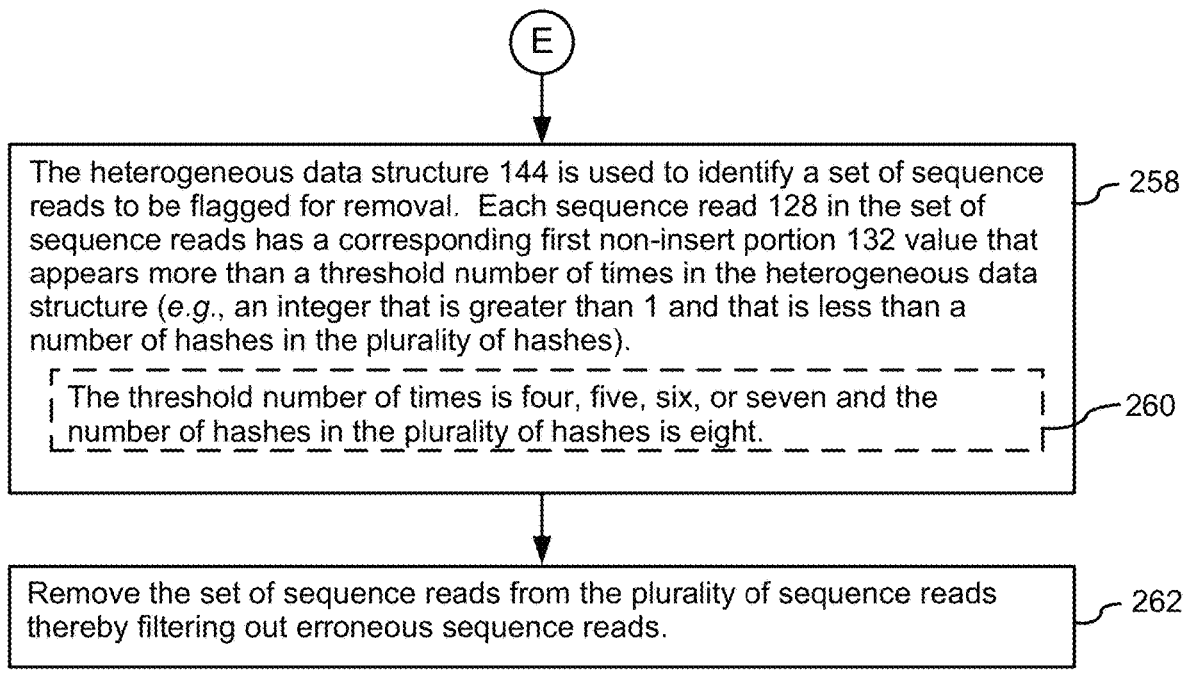

In some embodiments, a procedure such as that outlined in blocks 218 through 226 is performed prior to performing the remainder of the disclosed methods in conjunction with FIGS. 2C, 2D, and 2E in order to reduce the computational expense. However, in some embodiments, for instance where the multiplexed sequencing reaction dataset 126 is small enough, a procedure such as that outlined in blocks 218 through 226 is not performed.

Referring to block 228 of FIG. 2C, for each respective hash 140 in a plurality of hashes, a corresponding hash data structure is formed 148.

As used herein, a hash 140 is a set over possible positions within the first non-insert portion 132, with some number of positions omitted. A hash 140 as used herein can also be represented as a bitset over all positions, with some number of positions being false/zero. As such, the hashes 140 of the present disclosure are a form of "locality sensitive hashing." In some embodiments of the present disclosure, nucleotide positions that are set to false/zero do not contribute to the length of a hash value. To illustrate hashes, consider the case where the non-insert portion 132 is 28 base pairs long (N=28). A hash will produce a hash value that is L base pairs long. Necessarily, L will need to be less then N because the definition of a hash requires that it omit at least some positions. The omission of such regions in a hash, as will be explained in more detail below, advantageously allows for sequence errors at the omitted positions. In the case where the non-insert portion 132 is 28 base pairs long, one example of a hash is:

QQQXQQQQQQQQQQXQXQQQXQQQQQQQ (hash 1)

where each character represents a position (base pair) in the hash 140 and Q accepts the underlying nucleotide value of the non-insert portion 132 and X omits the underlying base pair value of the non-insert portion 132 to arrive at the hash value. So, for example, if the non-insert portion 132 has the sequence:

(SEQ ID. No.: 3)
ATGCATGAATGCCATAGACAGGCATCGA hash 1 will produce the hash value 152:

(SEQ ID. No.: 4)
ATG_ATGAATGCCA_A_ACA_GCATCGA where underscores represent false/zero positions in accordance with the hash. This hash value 152 (SEQ ID. No. 4) can be equivalently written as:

(SEQ ID. No.: 5).
ATGATGAATGCCAAACAGCATCGA

In the above case, N (the length of the first non-insert portion 132) is 28 and L, the length of the hash value, is 28−4=24. Another example hash in accordance with the present disclosure is:

QQQXQQQQQQQQQQXQXQQQXQQQQXXX (hash 2)

where each character in the hash again represents a position (base pair) in the hash 140 and Q accepts the underlying nucleotide value of the non-insert portion 132 and X omits the underlying base pair value of the non-insert portion 132. So, for example, if the non-insert portion 132 has the sequence:

(SEQ ID NO: 3)
ATGCATGAATGCCATAGACAGGCATCGA hash 2 will produce the hash value 152:

(SEQ ID NO: 6)
ATG_ATGAATGCCA_A_ACA_GCAT where underscores in the hash value 152 (SEQ ID. No. 6) represent false/zero positions in accordance with the hash. This hash value 152 (SEQ ID. No. 6) can be equivalently written as:

(SEQ ID NO: 7)
ATGATGAATGCCAAACAGCAT.

The corresponding hash data structure for each hash includes a representation 150 of each respective sequence read 128, in the plurality of sequence reads, and comprises a hash value 152 (e.g., SEQ ID NO: 5, SEQ ID NO: 7 in the examples of above), of length L nucleotide positions, where L is less than N, formed by hashing at least the corresponding first non-insert portion 132 of the respective sequence read 128 in accordance with the respective hash 140, thereby forming a plurality of hash data structures 148. This is illustrated in FIG. 1B. In FIG. 1B, there is a hash data structure 148 for each hash 140. Hash 1 and Hash 2 in the examples above represent two possible hashes 140 in the case where the first non-insert portion has a length of 28 base pairs. For each hash data structure 148, there is a representation 150 for each sequence read in the plurality of sequence reads in the multiplexed sequencing reaction dataset 126. In other words, each representation 150 in a hash data structure 148 uniquely corresponds to a sequence read 128 in the multiplexed sequencing reaction dataset 126. As illustrated in FIG. 1B, each representation 150 includes the hash value 152. For example, hash value 152-1-1 is formed by hashing the first non-insert portion 132 of the sequence read 128 that uniquely corresponds to representation 150-1-1 using the hash 140 that uniquely corresponds to the hash data structure 148-1.

Referring to block 230 of FIG. 2C, in some embodiments, N is between 10 and 100, and M is between 5 and 20. In other words, in some embodiments, the length of the first non-insert portion 132 is between 5 base pairs and 100 base pairs long and the length of the second non-insert portion 138 (which provides the sample identifier) is between five base pairs long and 20 base pairs long. In typical embodiments, each sequence read 128 has the same N and the same M. In other words, in typical embodiments, each sequence read 128 has a first non-insert portion 132 that is of the same first length (e.g., 28 base pairs) and a second non-insert portion of the same second length (e.g., 10 base pairs). In some embodiments, N is between 5 and 200 and M is between 4 and 50.

Referring to block 232 of FIG. 2C, in some embodiments, subject to the restriction that L must be less then N, L is between 4 and 99 (block 236). In other words, subject to the restriction that L must be less then N, in some embodiments the length of each hash value 152 produced by a hash 140 is between 4 base pairs and 99 base pairs in length. In typical embodiments, each hash value 152 in the hash data repository 142 (FIG. 1B) is the same length (e.g., length L).

Referring to block 234 of FIG. 2C, in some embodiments N is between 36 and 40, and M is 8. In other words, in some embodiments, the length of each first non-insert portion 132 (or at least the portion of the first non-insert portion 132 that is hashed by a hash 140) is between 36 and 40 base pairs and the length of the second non-insert portion is 8 base pairs.

Referring to block 238 of FIG. 2C, in some embodiments the hash value 152 formed by hashing at least the corresponding first non-insert portion 132 of the respective sequence read 128 in accordance with the respective hash 140 comprises forming the hash value 152 from a predetermined subset of nucleotide positions in the corresponding first non-insert portion 132. The predetermined subset of nucleotide positions is defined by the respective hash 140 and is unique to the respective hash 140.

Referring to block 240 of FIG. 2C, in some embodiments each respective hash 140 in the plurality of hashes defines a different predetermined subset of nucleotide positions in the first non-insert portion 132. As such, each respective hash can be considered a mask.

Referring to block 242 of FIG. 2C, in some embodiments the plurality of hashes, that is the number of different hashes 140 used in the present disclosure and thus the number of hash data structure 148 created, consists of between three and one hundred hashes 140. In some embodiments the plurality of hashes, that is the number of different hashes 140 used in the present disclosure and thus the number of hash data structure 148 created, consists of between 5 and 10 hashes 140, between 8 and 15 hashes 140, between 5 and 30 hashes 140, or between 5 and 50 hashes 140. Referring to FIG. 1B, the hash data structure repository is shown as having a discrete hash data structure 148 for each hash. This is disclosed in this way for ease of illustration. The plurality of hash data structures 148 can be in any form of data structure, table or otherwise, that is capable of tracking the individual hash values for individual hashes of individual sequence reads. Thus, in fact, the plurality of hash data structures 148 may themselves be elements of some other data structure that does not require the relisting of the second non-insert portions 138 and optional file identifiers 139 across each hash data structure 148 as is shown in FIG. 1B.

In some embodiments, the hashes 140 are generated on a randomized basis. That is, in some embodiments, the hashes 140 are a randomized set of hashes with maximally uniform coverage of bases in the first non-insert portion 132 across the set of all hashes. In some embodiments this is accomplished by considering each hash 140 to be a bit-set of read positions within the first non-insert portion 132. Then, for each respective position in the first non-insert portion 132, the number of hashes that have set the respective position across the set of hash is summed. In this way, a sum is calculated for each position in the first non-insert portion 132. A mean of these sums (if integer) or the floor or ceiling of the mean (if rational) is then computed. With this in mind, Q hashes 140 are generated, where Q is a positive integer of 2 or greater (e.g., 8). For 1, . . . , Q, a vector of length N (the length of the first non-insert portion 132) {0, 1, . . . , N–1} is generated and the first L elements is taken. For example, consider the case where N is 10, L is 7, and Q is 5. Before randomized shuffling, the vector will have the values:

{1, 2, 3, 4, 5, 6, 7, 8, 9, 10}

This vector is randomly shuffled thereby producing the vector:

{3, 4, 1, 2, 6, 5, 10, 9, 8, 7} and the first L elements is taken to produce the hash:

{3, 4, 1, 2, 6, 5, 10}

This hash sets positions 3, 4, 1, 2, 6, 5, 10 in the first non-insert portion 132 as true and ignores (sets as false) the other positions to arrive at a hash value 152. To generate the next hash, the vector:

{1, 2, 3, 4, 5, 6, 7, 8, 9, 10} is again randomly shuffled. Alternatively, the equivalent vector:

{3, 4, 1, 2, 6, 5, 10, 9, 8, 7} is randomly shuffled thereby producing the vector:

{4, 8, 10, 2, 7, 9, 1, 5, 3, 6} and the first L elements is taken to produce the hash:

{4, 8, 10, 2, 7, 9, 1}.

This hash sets positions 4, 8, 10, 2, 7, 9, and 1 (or equivalently 1, 2, 4, 7, 8, 9, and 10) in the first non-insert portion 132 as true and ignores (sets as false) the other positions to arrive at a hash value 152. This process continues until the Q hashes have been created. With the Q hashes, the coverage at each position in the first non-insert portion is determined. For example, how many of the Q hashes set position "1" in the first non-insert portion true, how many of the Q hashes set position "2" in the first non-insert portion true, and so forth. Then, a position i of lessor coverage and a position j of greater coverage (both relative to the mean coverage) and a hash in the set of Q hashes that contains position j (sets position j as true) but does not contain position i (sets position i as false) is swapped for this position (replace j with i). So for example, in the hashes described above:

{4, 8, 10, 2, 7, 9, 1}

{3, 4, 1, 2, 6, 5, 10} suppose that position 3 is greater than the mean coverage and position 9 is below the mean coverage. In this instance, the hash:

{3, 4, 1, 2, 6, 5, 10} is replaced with the hash:

{9, 4, 1, 2, 6, 5, 10}

This hash sets positions 1, 2, 4, 5, 6, 9 and 10 as true and the rest as false. This type of swapping is repeated until all positions are the mean (if integer) or floor or ceiling of the mean (if rational).

The above is just one nonlimiting example of methods for generating hashes 140 and other schemes that may produce suitable hashes that are collectively as uncorrelated as possible or where the union of each e.g. pair of hashes omits the positions in the first non-insert portion 132 as uniformly and uncorrelated as possible. Once the hashes are chosen, they are fixed through the remainder of the disclosed processes.

Referring to block 244 of FIG. 2D, the disclosed systems and methods continue by performing a procedure outlined in blocks 246 and 248 for each respective hash data structure 148 in the plurality of hash data structures.

Figure 6:
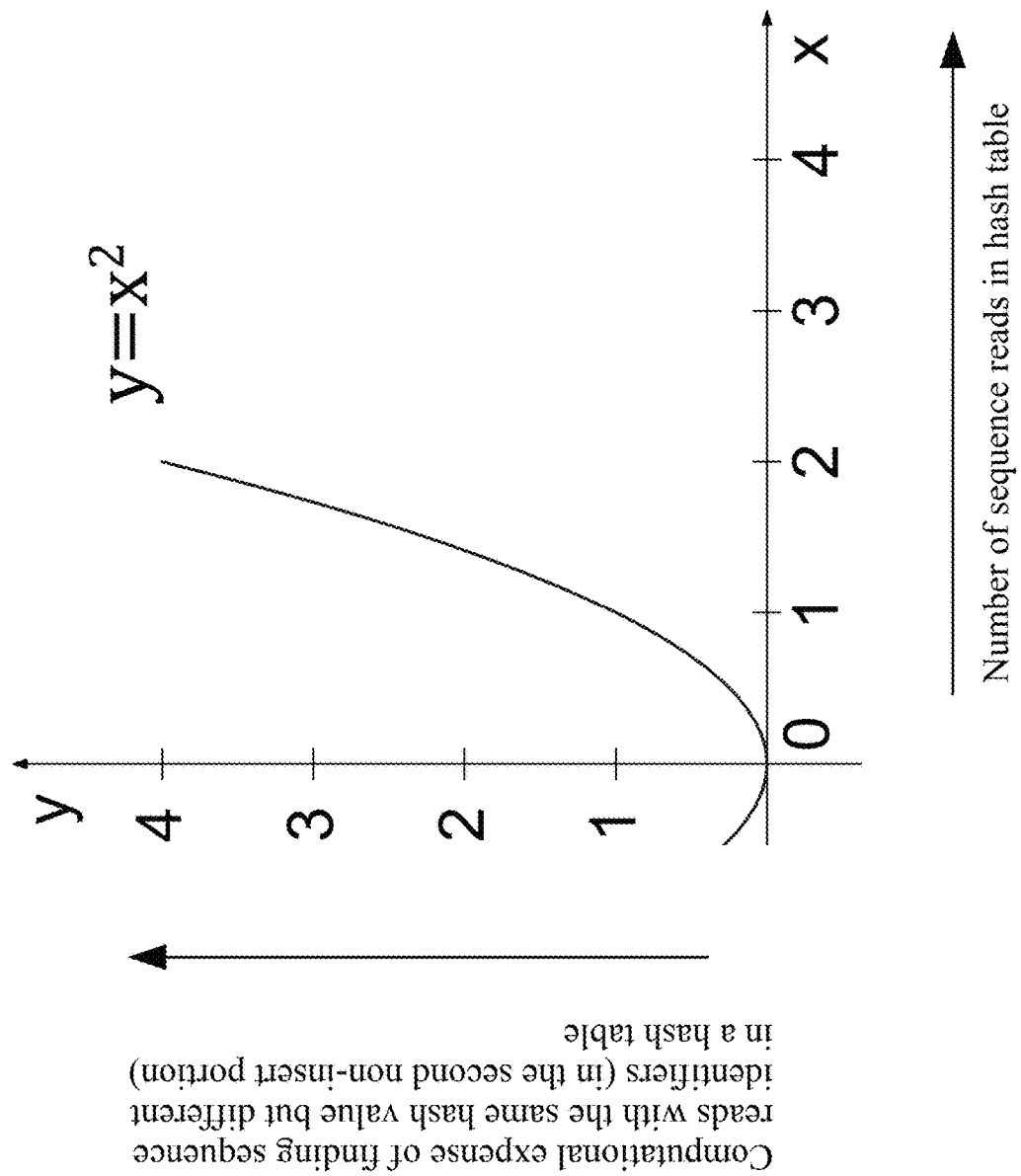
FIG. 6 illustrates the computational complexity of sequence read comparisons performed, as a function of the number of sequence reads compared, in accordance with some embodiments of the present disclosure.

Referring to block 246 of FIG. 2D, zero or more unique sequence read pairs are identified in each respective hash data structure 148. Each respective sequence read pair in the zero or more unique sequence read pairs includes a corresponding first sequence read and a corresponding second sequence read sharing a common hash value 152 and having different second values for the sample index of the second non-insert portion. Thus, referring to FIG. 1D, in hash data structure 1, if sequence reads 128-1 and sequence read 128-2 have the same hash value 152 and different sample indexes in their respective second non-insert portions, they are identified. There is no requirement that such a sequence read pair be found in each hash data structure. Some hash data structures may have no such pairs. Further, the number of sequence read pairs found in each hash data structure can be different. Further still, there is no requirement that the same sequence read pair be found in each hash data structure. The optional embodiments for filtering out sequence reads from the multiplexed sequencing reaction 126 prior to forming the hash data structures 144 described above in conjunction with blocks 218 through 226 of FIG. 2C serve to improve the computational efficiency of the sequence reads comparisons that are performed in block 246. If the number of sequence reads in the hash tables is very large, then the iteration over pairs of sequence reads in each hash table potentially becomes a very large quadratic processing step in some embodiments. Thus, for example, the amount of computation that may be required to perform the searches for pairs in just one of the multiple hash tables could increase, in some embodiments, approximately by a factor of four when the number of sequence reads represented in the hash table is doubled. Moreover, the amount of computation that may be required to perform the searches for pairs in just one of the multiple hash tables increases, in some embodiments, approximately by a factor of 100 when the number of the sequence reads in the hash table is increased by a factor of ten. In general, as the number of sequence reads represented in a hash table is increased by a certain amount, the running time (computation) to perform the sequence comparisons for that hash table in accordance with block 246, in some embodiments, could increase by the square of that amount. FIG. 6 plots the approximate running time (computational expenses) (Y-axis) against the number of sequence reads (X-axis) represented in a hash table in some embodiments. As FIG. 6 shows, this function can be described as a parabolic, or quadratic function, because as one moves along the x-axis of the parabola, any increase in the x-coordinate corresponds to a squared increase in the y-coordinate. Algorithms such as those used in some embodiments of block 246 are thus called quadratic-time algorithms. The reason that the search of block 246 runs in quadratic time in some embodiments is that the identification of two sequence reads that have the same hash value but different identifiers in their second non-insert portions is a check for the distinctness of elements in a list. Each sequence read needs to be compared to every other sequence read in the list. Consider how many comparisons need to be made in the scenario, for a list of length N. One compares the first sequence read against (N−1) sequence reads, the second sequence reads against (N−2) sequence reads, the third sequence read against (N−3) sequence reads, and so on, until the last sequence read is compared. In total, (N−1)+(N−2)+(N−3)+ . . . +2+1 comparisons are performed, which, according to Gauss, is [N*(N−1)]/2 total comparisons, or $(N^2-N)/2$ total comparisons. For large values of N, the $N^2$ term begins to eclipse the value of N. In some embodiments, block 246 is designed so that the computational complexity is other than quadratic. However, in some such embodiments, the complexity of block 246 is still greater than linear time and thus the sequence read reduction of blocks 218 and 226 greatly increases the speed at which block 246 is performed in such embodiments.

Referring to block 248 of FIG. 2D, a corresponding entry 149 is added into a heterogeneous data structure 144 for each respective unique sequence read pair in the zero or more unique sequence read pairs identified using each respective hash data structure 148. The corresponding entry 149 includes at least the corresponding first 132 and second 138 non-insert portions of the corresponding first sequence read 128 and the corresponding first 132 and second 138 non-insert portions of the corresponding second sequence read of the respective unique sequence read pair.

Referring to block 250 of FIG. 2D, in some embodiments the corresponding hash data structure 148 is a corresponding first table. Each row in the corresponding first table includes the representation 150 of a respective sequence read 128 in the plurality of sequence reads. The representation of each sequence read further comprises the corresponding second non-insert portion 138 of the sequence read. The corresponding first table is sorted on hash value 152. Referring to block 252 of FIG. 2D, in some such embodiments, each sequence read 128 further comprises a file identifier 139 identifying a file name that contains the sequence read and the representation 150 of each sequence read in the corresponding first table further comprises the file identifier.

Referring to block 254 of FIG. 2D, in some embodiments the heterogeneous data structure 144 is a second table. Each row in the second table includes a corresponding entry 149. The second table is sorted in lexicographic field order using at least the first and second non-insert portions of the corresponding first sequence read and the first and second non-insert portions of the corresponding second sequence read of each corresponding entry in the second table.

Referring to block 256 of FIG. 2D, and as illustrated in FIG. 1C, in some embodiments the corresponding entry 149 in the heterogeneous data structure 144 further includes the file identifier 139-A of the corresponding first sequence read 129-A and the file identifier 139-B of the corresponding second sequence read 129-B of the respective unique sequence read pair.

Exact matching algorithms will remove any pair of sequence reads that have the same first non-insert portion but different second non-insert portions.

In the disclosed approach, any pair of sequence reads that have the same first non-insert portion but different second non-insert portions will be removed because such pairs of sequence reads will necessarily be represented by more than a threshold number of entries in the heterogeneous data structure.

However, the disclosed methods are more sensitive than exact matching algorithms because they can also remove some pairs of sequence reads that have different first non-insert portions 132 AND different second non-insert portions 138, provided that the number of entries for such pairs of sequence reads in the heterogeneous data structure are also greater than the threshold number of entries.

From the above, it will be appreciated that it is possible that two sequence reads that have different first non-insert portions 132 AND different second non-insert portions 138 will nevertheless be represented in an entry 149 of the heterogeneous data structure, when a hash value of the first non-insert portion of the first sequence read is found to match the hash value of a second sequence read in the multiplexed sequencing reaction dataset. The disclosed systems and methods remove such a pair of sequence reads from the multiplexed sequencing reaction dataset provided that the first and second sequence reads have matching hash values for greater than a threshold number of the hashes. So, consider the case where there are eight different hash functions, and the threshold number is four, and that a first and second sequence read have matching hash values for six of the eight hashes. The two sequence reads will be flagged for removal. Here, the less than one hundred percent match across the plurality of hashes (six out eight) indicates that the first non-insert portions 132 AND different non-insert portions 138 of the sequence read do not match. Nevertheless, rather than keeping the two sequence reads, they are still discarded because the greater than threshold number of matches suggests that the reason that the first non-insert portions 132 do not match is because of a sequencing error, rather than truly being different first non-insert portions 132. On the other hand, if the pair of sequence reads has less than four or more matching hash values, this would mean that the first non-insert portions 132 are quite different from each other (e.g., likely differ in more than just one base position) such that the chances that the first portions truly do not match each other are high. In this situation, the first and second sequence reads will be retained in the multiplexed sequencing reaction dataset 126.

Referring to block 258 of FIG. 2E, in some embodiments, the disclosed systems and methods use the heterogeneous data structure 144 to identify such sequence reads that have likely index hopped but have sequencing errors. These sequence reads that likely index hopped form a set of sequence reads. Each sequence read 128 in this set of sequence reads has a corresponding first non-insert portion 132 value that appears more than a threshold number of times in the heterogeneous data structure (e.g., an integer that is greater than 1 and that is less than a number of hashes in the plurality of hashes). Referring to block 260 of FIG. 2E, in some embodiments the threshold number of times is four, five, six, or seven and the number of hashes in the plurality of hashes is eight. In some embodiments the threshold number of times is a predetermined (fixed) number that is between thirty and ninety percent of the number of hashes in the plurality of hashes. In some such embodiments, the plurality of hashes is between five and 50. In some such embodiments, the plurality of hashes is between five and 50 and the threshold number of times is between thirty and ninety percent of the number of hashes in the plurality of hashes. For instance, in the case where the plurality of hashes is 50, the threshold number of times is between 15 (thirty percent) and 45 (ninety percent). Referring to block 262 of FIG. 2E, in some embodiments the set of sequence reads is removed from the plurality of sequence reads thereby filtering out erroneous sequence reads.

Example 1. Sequencing Using Partitions

In some embodiments, sequence reads are acquired using partitions such as gel bead-in emulsions beads. Each partition maintains separation of its own contents from the contents of other partitions. As used herein, the partitions refer to containers or vessels that may include a variety of different forms, e.g., wells, tubes, micro or nanowells, through holes, or the like. In some embodiments, however, the partitions are flowable within fluid streams. In some embodiments, these vessels are comprised of, e.g., microcapsules or micro-vesicles that have an outer barrier surrounding an inner fluid center or core, or have a porous matrix that is capable of entraining and/or retaining materials within its matrix. In a preferred aspect, however, these partitions comprise droplets of aqueous fluid within a non-aqueous continuous phase, e.g., an oil phase. A variety of different suitable vessels are described in, for example, U.S. Patent Publication No. 20140155295, entitled "Capsule Array Devices and Methods of Used," filed Aug. 13, 2013, which is hereby incorporated by reference herein in its entirety. Likewise, emulsion systems for creating stable droplets in non-aqueous or oil continuous phases are described in detail in, e.g., U.S. Pat. No. 9,012,390, entitled "Fluorocarbon Emulsion Stabilizing Surfactants," which is hereby incorporated by reference herein in its entirety.

In certain embodiments, microfluidic channel networks are particularly suited for generating partitions. Examples of such microfluidic devices include those described in detail in U.S. Pat. Nos. 10,610,865, 9,694,361 and 10,150,117, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of test nucleic acid fragments (the nucleic acids that are to be sequenced thereby forming sequence reads) into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides.

The relative amount of sample materials within any particular partition may be adjusted by controlling a variety of different parameters of the system, including, for example, the concentration of test nucleic acid fragments in the aqueous stream, the flow rate of the aqueous stream and/or the non-aqueous stream, and the like. The partitions described herein are often characterized by having overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% of the above described volumes. In some cases, the use of low reaction volume partitions is particularly advantageous in performing reactions with small amounts of starting reagents, e.g., input test nucleic acid fragments. Methods and systems for analyzing samples with low input nucleic acids are presented in U.S. PCT Publication WO2014/210353, as well as WO2015/200871, entitled "Methods and Compositions for Sample Analysis, the full disclosures of which are hereby incorporated by reference in their entirety.

Once the test nucleic acid fragments are introduced into their respective partitions, the test nucleic acid fragments within partitions are generally provided with unique barcodes such that, upon characterization of those test nucleic acid fragments, they may be attributed as having been derived from their respective partitions. In some embodiments, such unique barcodes are previously, subsequently or concurrently delivered to the partitions that hold the compartmentalized or partitioned test nucleic acid fragments, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

Accordingly, the fragments are typically co-partitioned with the unique barcodes (e.g., barcode sequences). In particularly preferred aspects, the unique barcodes are provided in the form of oligonucleotides that comprise nucleic acid barcode sequences that is attached to test nucleic acid fragments in the partitions. The oligonucleotides are partitioned such that as between oligonucleotides in a given partition, the nucleic acid barcode sequences contained therein are the same, but as between different partitions, the oligonucleotides can, and preferably have differing barcode sequences. In preferred embodiments, only one nucleic acid barcode sequence is associated with a given partition, although in some embodiments, two or more different barcode sequences are present in a given partition.

The nucleic acid barcode sequences will typically include from 6 to about 20 or more nucleotides within the sequence of the oligonucleotides. In some embodiments, these nucleotides are completely contiguous, e.g., in a single stretch of adjacent nucleotides. In alternative embodiments, they are separated into two or more separate subsequences that are separated by one or more nucleotides. Typically, separated subsequences are separated by about 4 to about 16 intervening nucleotides.

The test nucleic acid is typically partitioned such that the nucleic acids are present in the partitions in relatively long fragments or stretches of contiguous nucleic acid molecules of the original test nucleic acid. As illustrated in FIG. 4, these fragments 306 typically represent a number of overlapping fragments of the overall test nucleic acid to be analyzed, e.g., an entire chromosome, exome, or other large genomic fragment. In some embodiments, the test nucleic acid 602 includes whole genomes, individual chromosomes, exomes, amplicons, or any of a variety of different nucleic acids of interest. Typically, the fragments 306 of the test nucleic acid 602 that are partitioned are longer than 1 kbp, longer than 5 kbp, longer than 10 kbp, longer than 15 kbp, longer than 20 kbp, longer than 30 kbp, longer than 40 kbp, longer than 50 kbp, longer than 60 kbp, longer than 70 kbp, longer than 80 kbp, longer than 90 kbp or even longer than 100 kbp.

The test nucleic acid 602 is also typically partitioned at a level whereby a given partition has a very low probability of including two overlapping fragments 306 of the starting test nucleic acid 602. This is typically accomplished by providing the test nucleic acid 602 at a low input amount and/or concentration during the partitioning process. As a result, in preferred cases, a given partition includes a number of long, but non-overlapping fragments 306 of the starting test nucleic acid 602. The nucleic acid fragments 306 in the different partitions are then associated with unique barcodes where, for any given partition, nucleic acids contained therein possess the same unique barcode, but where different partitions include different unique barcodes. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In some embodiments, in excess of 10,000, 100,000, 500,000, etc. diverse barcode types are used to achieve genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome. Here, each such genome is an example of a test nucleic acid.

Often the above-described partitioning is performed by combining the sample containing the test nucleic acid with a set of oligonucleotide tags (containing the barcodes) that are releasably-attached to beads prior to the partitioning step. The oligonucleotides may comprise at least a primer region and a barcode region. See, for example, the disclosure on co-partitioning of oligonucleotides and associated barcodes and other functional sequences, along with sample materials as described in, for example, PCT Publication WO2019/157529, PCT Publication WO2018/119447, PCT Publication WO2014/210353 entitled "Compositions and Methods for Sample Processing," and U.S. Patent Publication No. US201403878345, U.S. Pat. Nos. 10,550,429 and 10,815,525, as well as U.S. Pat. No. 10,150,964 entitled "Partitioning and Processing of Analytes and Other Species," the full disclosures of which is hereby incorporated by reference in their entireties.

In one exemplary process, beads are provided, where each such bead includes large numbers of the above described oligonucleotides releasably attached to the beads. In such embodiments, all of the oligonucleotides attached to a particular bead include the same nucleic acid barcode sequence, but a large number of diverse barcode sequences are represented across the population of beads used. Typically, the population of beads provides a diverse barcode sequence library that includes at least 1000 different barcode sequences, at least 10,000 different barcode sequences, at least 100,000 different barcode sequences, or in some cases, at least 1,000,000 different barcode sequences. Additionally, each bead typically is provided with large numbers of oligonucleotide molecules attached. In particular, the number of molecules of oligonucleotides including the barcode sequence on an individual bead may be at least about 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

In some embodiments, the oligonucleotides are releasable from the beads upon the application of a particular stimulus to the beads. In some cases, the stimulus is a photo-stimulus, e.g., through cleavage of a photo-labile linkage that may release the oligonucleotides. In some cases, a thermal stimulus is used, where elevation of the temperature of the beads environment results in cleavage of a linkage or other release of the oligonucleotides form the beads. In some cases, a chemical stimulus is used that cleaves a linkage of the oligonucleotides to the beads, or otherwise results in release of the oligonucleotides from the beads.

In some embodiments, the beads including the attached oligonucleotide tags are co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, in some embodiments, the flow rate is controlled to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 3:
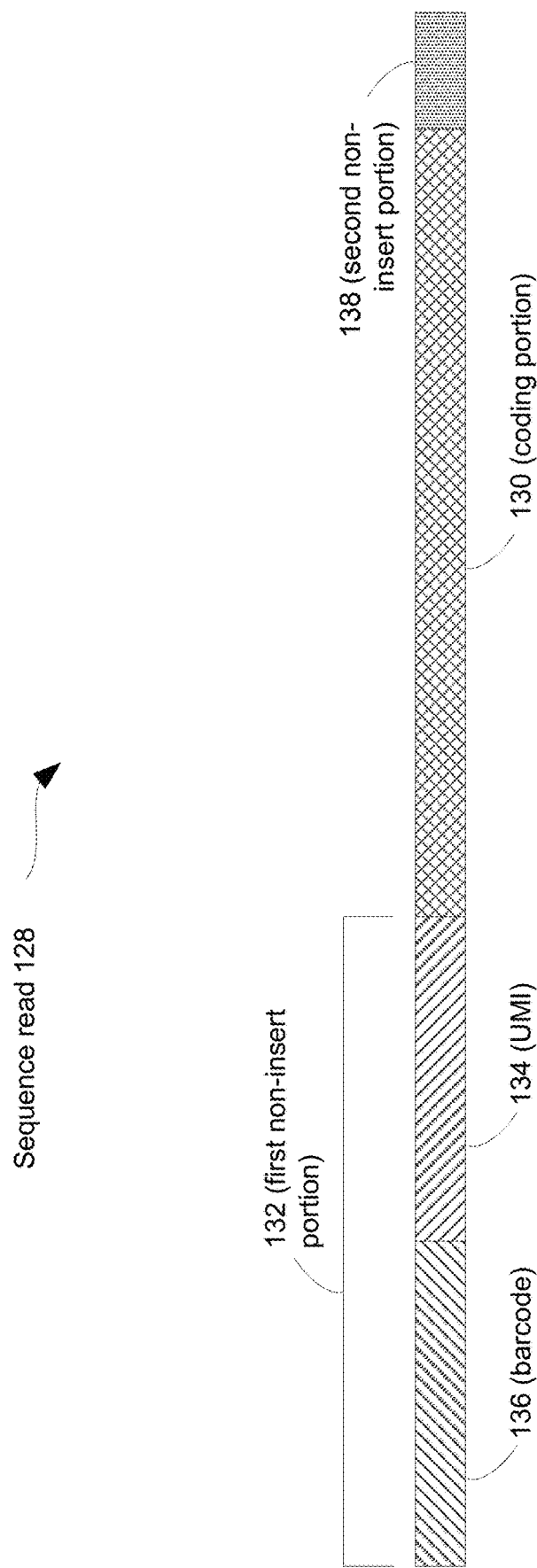
FIG. 3 illustrates an exemplary constructs in accordance with some embodiments of the present disclosure.

FIG. 3 of United States Patent Application Publication No. US20150376700, filed Jun. 26, 2015, entitled "Analysis of Nucleic Acid Sequences," which is hereby incorporated by reference and the portions of the specification describing FIG. 3 provide a detailed example of one method for barcoding and subsequently sequencing a test nucleic acid (referred to in the reference as a "sample nucleic acid") in accordance with one embodiment of the present disclosure. As noted above, while single bead occupancy may be the most desired state, it will be appreciated that multiply occupied partitions, or unoccupied partitions may often be present. FIG. 4 of United States Patent Application Publication No. US20150376700, filed Jun. 26, 2015, entitled "Analysis of Nucleic Acid Sequences," which is hereby incorporated by reference and the portions of the specification describing FIG. 4 provide a detailed example of a microfluidic channel structure for co-partitioning samples and beads comprising barcode oligonucleotides in accordance with one embodiment of the present disclosure.

Once co-partitioned, the oligonucleotide tags disposed upon the bead are used to barcode and amplify the partitioned samples. One process for use of these barcode oligonucleotides in amplifying and barcoding samples is described in detail in PCT Publication WO2019/157529, PCT Publication WO2018/119447, PCT Publication WO2014/210353 entitled "Compositions and Methods for Sample Processing," U.S. Patent Publication No. US20140387345, U.S. Pat. Nos. 10,550,429 and 10,815,525, as well as U.S. Pat. No. 10,150,964 entitled "Compositions and Methods for Sample Processing," the full disclosures of which are hereby incorporated by reference in their entireties. Briefly, in one aspect, the oligonucleotides present on the beads that are co-partitioned with the samples are released from their beads into the partition with the samples. The oligonucleotides typically include, along with the barcode sequence, a primer sequence at its 5' end. In some embodiments, this primer sequence is a random oligonucleotide sequence intended to randomly prime numerous different regions of the samples. In some embodiments the primer sequence is a specific primer sequence targeted to prime upstream of a specific targeted region of the sample.

Once released, the primer portion of the oligonucleotide anneals to a complementary region of test nucleic acid fragments 306 in the partition. Extension reaction reagents, e.g., DNA polymerase, nucleoside triphosphates, co-factors (e.g., $Mg^{2+}$ or $Mn^{2+}$ etc.), that are also co-partitioned with the fragments 306 and beads 304, extend the primer sequence using the fragments as a template, to produce a complementary sequence to the strand of the test nucleic fragment to which the primer annealed, and this complementary sequence includes the oligonucleotide and its associated barcode sequence. Annealing and extension of multiple primers to different portions of the fragments in the partition may result in a large pool of overlapping complementary portions of the test nucleic acid fragments, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure that reduces the ability of the molecule to be the basis for producing further iterative copies.

Oligonucleotides that include a barcode sequence are co-partitioned in, e.g., a droplet in an emulsion, along with a sample test nucleic acid fragment. In some embodiments, the oligonucleotides are provided on a bead that is co-partitioned with the test nucleic acid fragment. The oligonucleotides are preferably releasable from the bead. The oligonucleotides includes a barcode sequence, in addition to one or more functional sequences. For example, an oligonucleotide 302 may further comprises an attachment sequence that may function as an attachment or immobilization sequence for a given sequencing system, e.g., a P5 sequence used for attachment in flow cells of an ILLUMINA, HISEQ or MISEQ system. In other words, the attachment sequence is used to reversibly attach oligonucleotide to a bead in some embodiments. In some embodiments, the oligonucleotide also includes a primer sequence, which may include a random or targeted N-mer (discussed above) for priming replication of portions of the sample test nucleic acid fragment. Also included within an exemplary oligonucleotide, is a sequence that may provide a sequencing priming region, such as a "read1" or R1 priming region, that is used to prime polymerase mediated, template directed sequencing by synthesis reactions in sequencing systems. In many cases, the barcode sequence, immobilization sequence and exemplary R1 sequence may be common to all of the oligonucleotides attached to a given bead. The primer sequence may vary for random N-mer primers, or may be common to the oligonucleotides on a given bead for certain targeted applications.

The barcoded nucleic acid fragments may then be subjected to characterization, e.g., through sequence analysis, or they may be further amplified in the process.

All of the sequence reads from multiple different partitions may then be pooled for sequencing on high throughput sequencers as described herein. Because each sequence read 128 is coded as to its partition of origin, the sequence of that sequence read may be attributed back to its origin based upon the presence of the barcode.

This is schematically illustrated in FIG. 4. As shown in one example, a test nucleic acid fragment 306-1 and a test nucleic acid fragment 306-2 are each partitioned along with their own sets of barcode oligonucleotides as described above. Within each partition, each fragment (306-1 and 306-2) is then processed to separately provide overlapping sequence reads 128 of the fragments 306-1 and 306-2 to form respective sets of sequence reads. This processing provides sequence reads 128 with a barcode sequence 132 that is the same for each of the sequence reads derived from a particular fragment 306. A diverse library of barcodes may be used to differentially barcode large numbers of different sets of fragment reads. However, it is not necessary for every sequence read in a given partition to be barcoded with different barcode sequence. In fact, in many cases, multiple different first fragments may be processed concurrently to include the same barcode sequence. Diverse barcode libraries are described in detail elsewhere herein.

Notably, in FIGS. 3 and 4, the barcode can be positioned either before or after the unique molecular identifier.

The sequence reads may then be pooled for sequencing using, for example, sequence by synthesis technologies available from Illumina or Ion Torrent division of Thermo Fisher, Inc. Once sequenced, the sequence reads 128 can be attributed to their respective fragment set, e.g., as shown in aggregated reads, at least in part based upon the included barcodes, and optionally, and preferably, in part based upon the sequence of the fragment itself. The attributed sequence reads for each fragment set are then assembled to provide the assembled sequence for each sample fragment which in turn, may be further attributed back to their respective original fragments (306-1 and 302-2). Methods and systems for assembling genomic sequences are described in, for example, U.S. Provisional Patent Application No. 62/017,589, filed Jun. 26, 2014, and U.S. Patent Application Publication No. US20150376700, filed Jun. 26, 2015, the full disclosure of each of which is hereby incorporated by reference in its entirety.

In some embodiments, the biological sample is from a multi-chromosomal species and the test nucleic acid 602 comprises a plurality of nucleic acids collectively representing a plurality of chromosomes from the multi-chromosomal species (208).

Example 2—Example BAM File Containing Sequence Reads

In some embodiments the sequence reads of the present disclosure are in a format that is in accordance with the Chromium Single Cell 3' Solution, which is a commercial platform developed by 10× Genomics for preparing single cell cDNA libraries for performing single cell RNA-seq and the 10× Genomics software suite, called Cell Ranger, that processes the raw BCL files produced by an Illumina sequencer and outputs a final gene-barcode expression matrix.

TABLE 1

Example BAM file tags

| Line | Tag | Description |
| --- | --- | --- |
| 1 | NA | Query name |
| 2 | NA | Flag |
| 3 | NA | Reference name |
| 4 | NA | Position |
| 5 | NA | Mapping quality |
| 6 | NA | Cigar string |
| 7 | NA | Reference name of mate |
| 8 | NA | Position of mate |
| 9 | NA | Template length |
| 10 | NA | Sequence |
| 11 | NA | Sequence quality |
| 12 | NH | Number of reported alignments for query |
| 13 | HI | Query hit index |
| 14 | AS | Alignment score |
| 15 | nM | Number of mismatches per pair |
| 16 | RE | Region type (E = exonic, N = intronic, I = intergenic) |
| 17 | BC | Sample index read |
| 18 | QT | Sample index read quality |
| 19 | CR | Cell barcode |
| 20 | CY | Cell barcode read quality |
| 21 | CB | Cell barcode that is error-corrected and confirmed against a list of known-good barcode sequences |
| 22 | UR | Unique Molecular Identifier (UMI) |
| 23 | UY | UMI read quality |
| 24 | UB | UMI that is error-corrected among other molecular barcodes with the same cellular barcode and gene alignment |
| 25 | RG | Read group |

FIG. 5A illustrates the format of a sequence read in a BAM file in accordance with some embodiments of the present disclosure. The cell barcode (136) (10XBC) is used to associate cDNAs to a specific cell and the UMIs (134) are used to label specific cDNA molecules. After sequencing, Cell Ranger (using bcl2fastq) converts the BCL files into a set of FASTQ files. In each set are three files: R1, I1, and R2, which contains the sequence of the cell barcode+UMI, the sample index, and the cDNA sequence, respectively. Notably, in FIG. 5A, the cell barcode can be positioned either before or after the UMI.

The first read (R1) contains the cell barcode (136) sequence, which is 16 bp long in this example and a UMI sequence (134) that is 10 bp long in this example. In one example, the cell barcode (136) is TTAACTCGTAGAAGGA (Seq ID No.: 1), and the UMI (134) is GTCCGGCGAC (Seq ID. No.: 2). This information is incorporated into the BAM file as the CR and UR tags, respectively, of Table 1. The base calling quality of these bases, AAFFFJJJJJJJJJJ and JJJJJJJJJJ are stored as the CY and UY tags, respectively.

In addition to the CR and UR tags, there are the CB and UB tags, which contain the error-corrected cell barcode and UMI sequences. Errors in the cell barcode and UMI sequence can occur during the PCR amplification and sequencing steps, so the CB and UB tags contain the corrected sequences.

Many of Illumina's sequencers support multiplexing, e.g. indexing, which is what the 8 bp i7 sample index of FIG. 5A is used for (termed the second non-insert portion 138 in the present disclosure). The sample index sequence (the second non-insert portion 138) and its base calling qualities are stored in the BC and QT tags, respectively.

Finally, the second read (termed the insert portion 130 in the present disclosure) contains a partial sequence of the cDNA (98 bp long) of the sequence read 128. Since the sequencing of read2 goes from the 3' to 5' end in the disclosed embodiment, there is an enrichment of sequences from the 3' end, hence the protocol is called Chromium Single Cell 3' Solution. The sequence and base calling quality are stored in the $10^{th}$ and $11^{th}$ fields, respectively, of the BAM file described in Table 1.

Example 3—Example Workflows for Obtaining and Filtering Sequence Reads

Figure 13A:
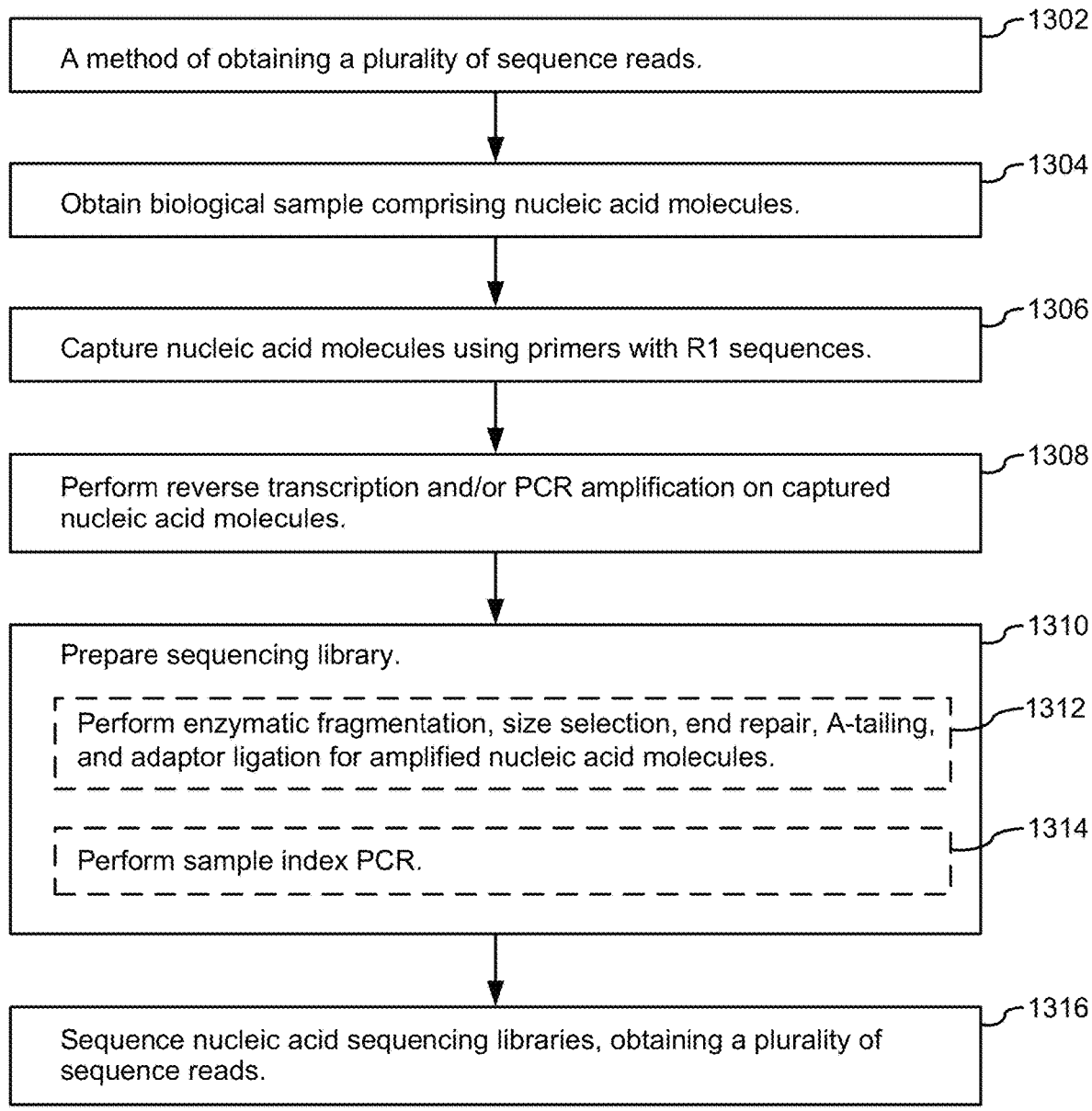
FIGS. 13A and 13B illustrate example workflows of a method for obtaining a plurality of sequence reads and filtering out erroneous sequence reads in accordance with some preferred embodiments of the present disclosure.
Figure 13B:
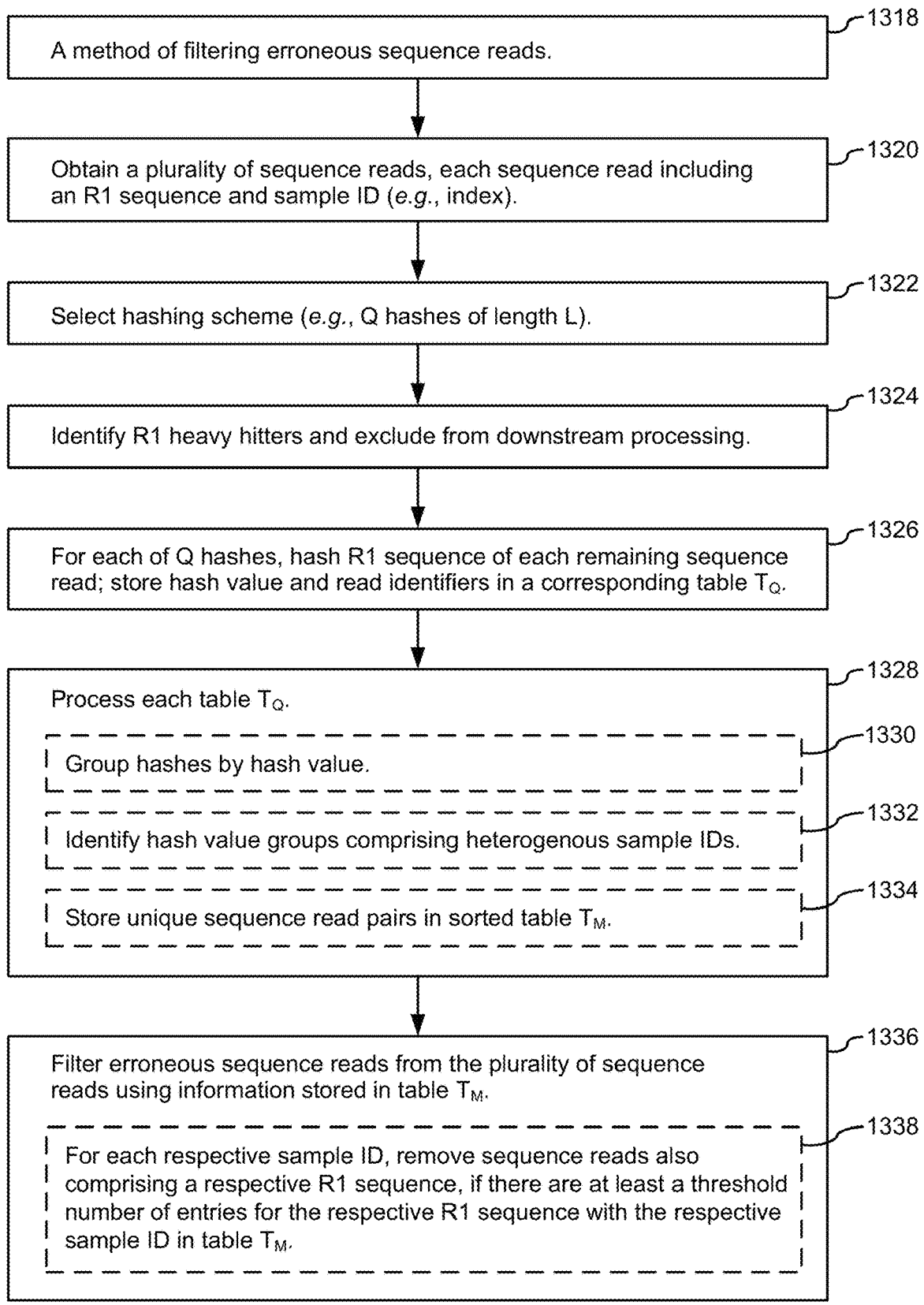

FIGS. 13A and 13B illustrate example workflows of a method for obtaining a plurality of sequence reads and filtering out erroneous sequence reads, in accordance with some preferred embodiments of the present disclosure. Although FIGS. 13A and B provide examples of some preferred embodiments, the methods can comprise any of the embodiments disclosed herein, or any combinations, omissions, separations, and/or substitutions thereof as will be apparent to one skilled in the art.

FIG. 13A describes an example workflow 1302 of a method for obtaining a plurality of sequence reads, in accordance with some preferred embodiments of the present disclosure. Referring to block 1304, the method comprises obtaining one or more biological samples comprising nucleic acid molecules (e.g., mRNA, RNA, and/or DNA). Referring to block 1306, the nucleic acid molecules are captured using primers comprising R1 sequences, where the R1 sequences comprise a barcode sequence and a unique molecular identifier (UMI). The nucleic acid molecules can be captured using any of the methods and/or embodiments described above in Example 1: Sequencing using partitions. For example, in some embodiments, the nucleic acid molecules are captured using gel bead-in emulsions (GEM) beads, where each bead includes a plurality of oligonucleotides and each oligonucleotide comprises an R1 sequence including a barcode sequence and a UMI. The R1 sequence can be 26-28 base pairs (bp) long (e.g., a 16 bp barcode sequence and a 10-12 bp UMI). In some embodiments, the oligonucleotide further comprises a "Read 1" sequence (e.g., an Illumina TruSeq Read 1), used for sequencing the R1 sequence of the nucleic acid molecule. See, FIGS. 3, 4, 5 and 7A for illustrations of the "Read 1" sequence and the R1 sequence (e.g., the first non-insert portion 132, containing the barcode sequence 136 and the UMI 134).

As described in Example 2: Example BAM file containing sequence reads, in some embodiments, a respective bead in a plurality of beads comprises a respective plurality of oligonucleotides, where each oligonucleotide on the bead comprises the same barcode sequence but a unique UMI. In some such embodiments, preparation of biological samples in emulsion droplets using GEM beads results in the partitioning of a single cell with a single bead within an emulsion droplet, such that each respective barcode corresponds to a respective cell (e.g., cell barcodes). Thus, the R1 sequence provides identifying information for sequence reads, where the UMI denotes the identity of a specific nucleic acid molecule, and the cell barcode denotes the identity of the specific cell from which the respective nucleic acid molecule originated.

Referring to block 1308, the method further comprises performing reverse transcription and/or PCR amplification on captured nucleic acid molecules. Generally, this step provides for the inclusion of the "Read 1" sequence and the R1 sequence 132 into the nucleic acid molecule. For example, as described above in Example 1: Sequencing using partitions, in some embodiments the oligonucleotides may comprise a primer region that can be used to prime the nucleic acid molecule for an extension and/or an amplification reaction. An mRNA molecule thus captured for reverse transcription will result in a resulting cDNA molecule comprising the "Read 1" sequence and the R1 sequence 132 comprising identifying information (see, e.g., FIGS. 3, 4, 5 and 7A).

Referring to block 1310, the method further comprises preparing a sequencing library. In some embodiments, the preparation of the sequence library is performed after release of the reverse transcribed and/or amplified nucleic acid molecules (e.g., cDNA) from one or more partitions (e.g., a GEM bead and/or emulsion droplet). Referring to block 1312, the preparation of the sequencing library comprises performing enzymatic fragmentation, size selection, end repair, A-tailing and/or adaptor ligation for amplified nucleic acid molecules (e.g., cDNA). Generally, processing of the nucleic acid fragments comprises the addition of the "Read 2" sequence (e.g., Illumina TruSeq Read 2), used for sequencing the "Read 2" insert of the nucleic acid fragment. Depending on the size of the nucleic acid fragments after enzymatic fragmentation and size selection, the length of the Read 2 insert (e.g., the insert portion 130) can be approximately 91-98 bp. See, FIGS. 3, 4, 5 and 7A for illustrations of the "Read 2" sequence and the Read 2 insert.

Referring to block 1314, the preparation of the sequencing library further comprises performing sample index PCR. In some embodiments, the sample index PCR comprises a first primer including a P5 sequence and a partial Read 1 sequence, and a second primer including a P7 sequence, a sample index sequence, and a partial Read 2 sequence. As described in Example 1, the P5 and P7 sequences can function as attachment or immobilization sequences for a given sequencing system (e.g., attachment to Illumina flow cells). The partial Read 1 and partial Read 2 sequences can serve as a priming sequence for PCR amplification. The sample index i7 (e.g., the second non-insert portion 138 in FIGS. 3, 4, and 5) is a nucleotide sequence that provides identifying information as to the sample of origin of the respective nucleic acid fragment. For example, referring to FIG. 9, in some embodiments, the sample index PCR results in the inclusion of the P5, P7, and sample index sequences into the nucleic acid fragments in the sequencing library. The positioning of the P5, P7, and i7 sequences in the amplified nucleic acid fragments is further illustrated in FIGS. 5 and 7A.

Referring again to FIG. 9, in some embodiments, the sample index PCR comprises single-indexing, where only one sample index sequence is added to the nucleic acid fragment at one end of the fragment (e.g., included in the P7 primer). In some alternative embodiments, the sample index PCR comprises dual-indexing, where two sample index sequences are added to the nucleic acid fragment at each of both ends of the fragment (e.g., included in both the P5 and the P7 primers).

One or more nucleic acid molecules from a respective one or more individual cells from a biological sample can be pooled prior to preparation of the sequencing library. For example, in the case where a plurality of cells for a given biological sample were individually partitioned using a respective plurality of GEM beads in a respective plurality of emulsion droplets, the plurality of captured nucleic acid molecules (e.g., that are reverse transcribed and/or amplified) originating from the plurality of individual cells can be pooled together prior to fragmentation, processing and sample index PCR. Thus, the sample origin of all of the nucleic acid fragments originating from a plurality of cells from a single biological sample can be determined using the respective sample index sequence, in addition to the barcode denoting the cell origin and the UMI denoting the identity of the nucleic acid molecule. In some embodiments, the one or more biological samples is a plurality of biological samples, and the plurality of nucleic acid molecules corresponding to each respective biological sample in the plurality of biological samples is pooled prior to library preparation. Thus, in some such embodiments, each biological sample in the plurality of biological samples has a corresponding sequencing library in a plurality of corresponding sequencing libraries, where each sequencing library comprises nucleic acid fragments originating from the respective corresponding biological sample and having a respective sample index denoting the biological sample of origin. Generally, due to the high number of possible R1 sequences that can be constructed, a plurality of sequencing libraries can be designed such that there is virtually no overlap of R1 sequences between biological samples, thus ensuring that sequence reads can be uniquely assigned to specific sample indices.

Referring to block 1316, the method further comprises sequencing the nucleic acid sequence libraries, thereby obtaining a plurality of sequence reads. Sequencing can be performed using any of the methods and/or embodiments described in Example 1: Sequencing using partitions, and/or by any conventional methods for nucleic acid sequencing that will be apparent to one skilled in the art. In some embodiments, the sequencing is performed to generate gene expression datasets, CrG datasets, and/or CNV datasets. In some embodiments, the one or more biological samples is a plurality of biological samples, each biological sample has a corresponding sequencing library in a plurality of corresponding sequencing libraries, and the plurality of sequencing libraries is pooled prior to sequencing (e.g., multiplexing). In some such embodiments, after sequencing, the sample indices can be used to separate pooled sequence reads from a plurality of biological samples into their respective samples of origin (e.g., demultiplexing).

See also, 10× Genomics, 2019, "Chromium Next GEM Single Cell 3' Reagent Kits v3.1 User Guide", Document Number CG000204, Rev D, which is hereby incorporated herein by reference in its entirety, for further details on methods for obtaining a plurality of sequence reads.

FIG. 13B describes an example workflow 1318 of a method for filtering erroneous sequence reads, in accordance with some preferred embodiments of the present disclosure. Referring to block 1320, the method comprises obtaining a plurality of sequence reads, each sequence read including an R1 sequence (e.g., a first non-insert portion 132 comprising a barcode sequence 136 and a UMI 134) and a sample ID (e.g., a second non-insert portion 138 comprising a sample index sequence). The sequence reads can optionally be obtained using the method described in FIG. 13A, above.

The method can be performed using a filter (e.g., Index Hopping Filter). Generally, the sample ID of a sequence read denotes the sample from which the sequence read originated. However, in some embodiments, the plurality of sequence reads comprises one or more sequence reads with erroneous sample IDs (e.g., index hopping), thus resulting in erroneous sequence reads. For example, in Illumina sequencing devices (e.g., patterned flow cell technology), this phenomenon manifests as a percentage of reads from each sample comprising a sample index sequence from another sample on the same flow cell, in place of the original sample index sequence. This can occur where a plurality of sequencing libraries corresponding to a plurality of biological samples is pooled prior to sequencing, as described above in block 1316 of FIG. 13A. In some cases, index hopping can result in misassignment of sample origin during demultiplexing, the erroneous appearance of cell populations from a first sample in a second sample (e.g., appearance of infected cells in a healthy sample), and/or the observation of gene expression or immune profiles in cells where such expression did not actually occur. The filtering method mitigates such index-hopping phenomena by removing those reads that are presumed affected.

Referring again to FIG. 13B, the obtained sequence reads are preferably obtained in an electronic format, such as a demultiplexed FASTQ file from a sequencing flow cell. In such format, each sequence read in the plurality of sequence reads includes a corresponding sequence read identifier (e.g., a 26-28 bp R1 sequence comprising a 16 bp barcode and a 10-12 bp UMI) and a sample ID (e.g., an 8 bp sample index sequence). In some embodiments, each sequence read further includes a corresponding file ID indicating the FASTQ file from which it was obtained. The filtering method performs a locality sensitive hashing of the R1 sequence to derive equivalence between reads belonging to the same molecule prior to determining the respective identities of the R1 sequence and the sample ID to identify index-hopped sequence reads. The use of hashing, rather than exact matching, allows the filtering method to accommodate intermittent sequencing errors, thus providing an improvement in sensitivity over exact matching methods.

Figures 7A, 7B:
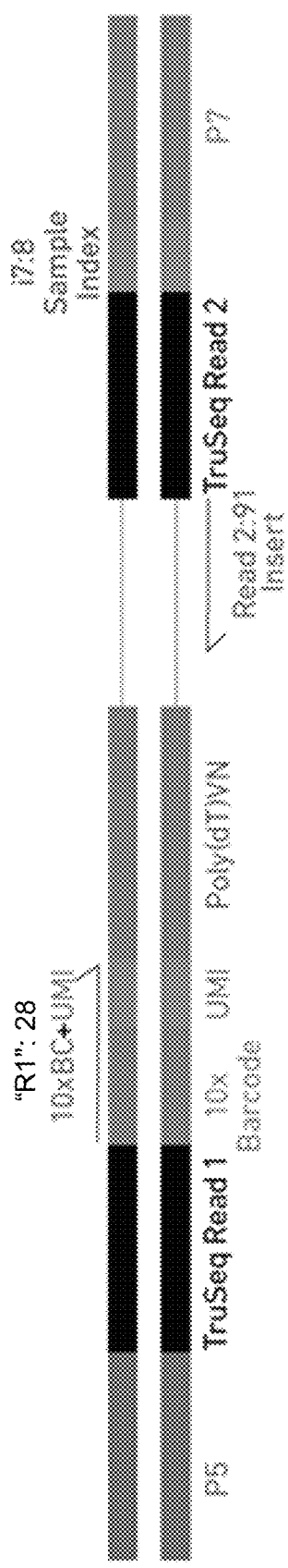
FIGS. 7A and 7B collectively illustrate one example of a hash that can be used to hash a first non-insert portion of a sequence read, in accordance with some embodiments of the present disclosure.

Referring to block 1322, the method further comprises selecting a number Q (e.g., 8) of hashes of a length L (e.g., 18-21 bp), using a chosen hashing scheme. As illustrated in FIG. 7B and described above in detail in the present disclosure, a hash, in the context of a sequence of nucleotide base pairs, is a set of nucleotides where some positions are omitted. Thus, in FIG. 7B, an 18 bp hash for a 28 bp R1 sequence is the 28 bp R1 sequence with positions 5, 8, 11, 13, 15, 16, 19, 25, 26, and 28 omitted.

An example of a hash selection scheme is described above in detail in the present disclosure. Briefly, a randomized set of hashes can be generated by, for each hash between 1 and Q, randomly shuffling a vector of the length of R1 (e.g., 26-28) $\{0, 1, \ldots Q-1\}$ and selecting the first L items, where the values of N and L are predetermined (e.g., randomly generated and/or selected by the user). The coverage of each position in R1 as represented in the set of Q hashes is determined. A position i of lesser coverage and a position j of greater coverage, relative to the mean, are selected and, for each hash that contains position j but not position i, i and j are swapped. Position swapping is repeated until the coverage of all positions equal the mean (if integer) or the floor or ceiling of the mean (if rational). The final selected hashes are fixed for the remainder of the method.

Referring to block 1324, the method further comprises identifying R1 "heavy hitters" to be excluded from downstream processing. As described in blocks 218-226 of FIG. 2B, the step of block 1324 reduces the computational expense of the filtering method by removing one or more sequence reads that fail to satisfy a uniqueness test (e.g., R1 sequences that appear many times in a plurality of samples). Briefly, in some preferred embodiments, the R1 heavy hitters are excluded from downstream processing as follows: first, each R1 sequence in the plurality of R1 sequences corresponding to each respective sequence read in the plurality of sequence reads, for a plurality of biological samples, is stored in a sorted table $T_{HH}$ with a corresponding sample ID and a corresponding file ID. Table $T_{HH}$ is grouped according to R1 sequences, using exact matching, and the table is iteratively searched to determine a count, for each R1 sequence, of sequence read matches between pairs of sample IDs. If, for any R1 sequence, there are more than 10,000 matches between any pair of sample IDs, the respective R1 sequence is designated as a "heavy hitter" and is excluded from downstream processing. All remaining sequence reads are retained for further processing and filtering.

Figure 8:
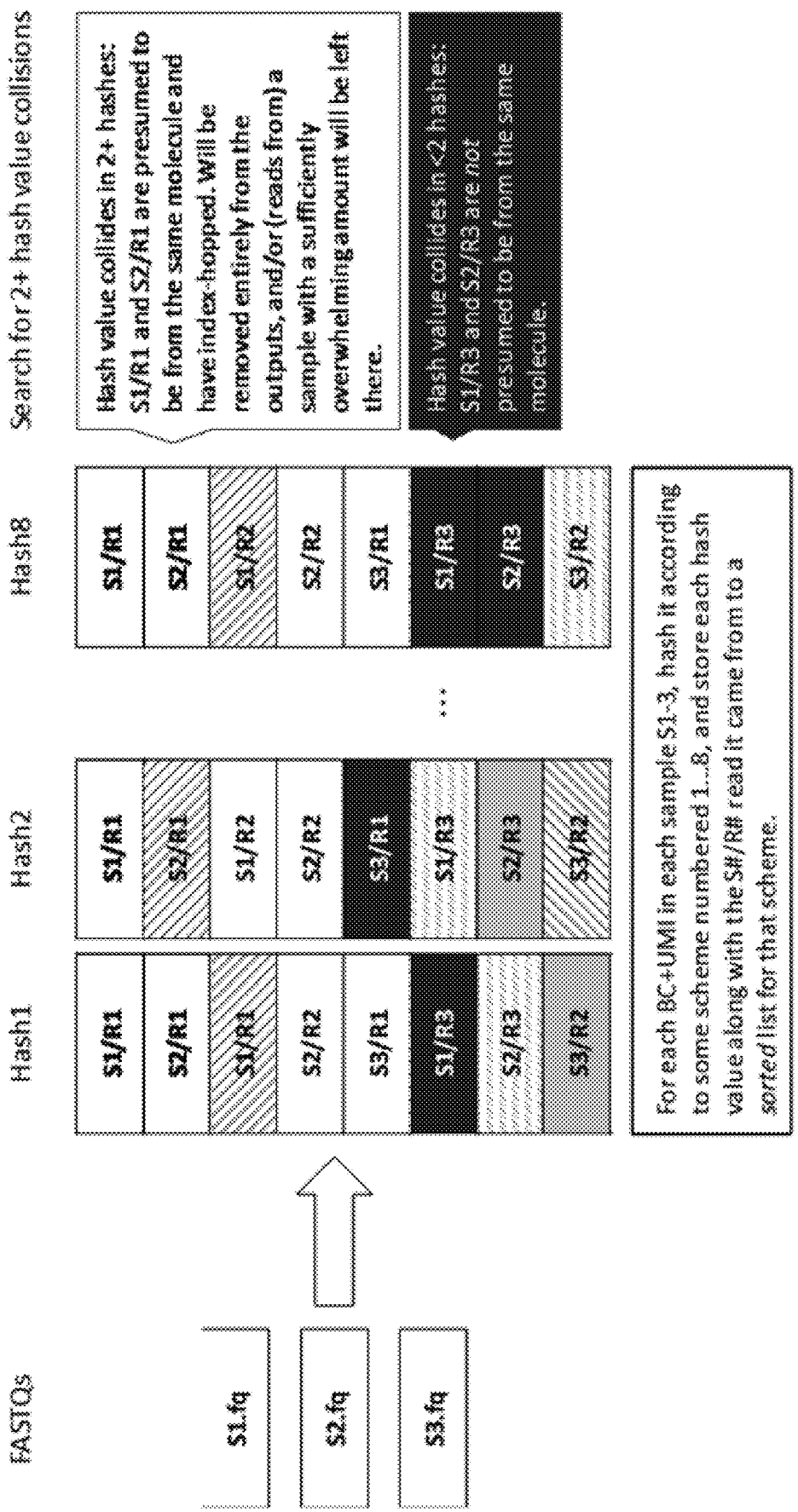
FIG. 8 illustrates an example of a plurality of hash data structures that can be used to identify zero or more unique sequence read pairs, in accordance with some embodiments of the present disclosure.

Referring to block 1326, the method further comprises, for each of Q hashes, hashing the R1 sequence of each remaining sequence read. The hashed R1 sequence (e.g., the hash value) and the corresponding read identifiers (e.g., a representation of the respective sequence read including sample ID, file ID, and/or sequence read ID) are stored in a corresponding hash data structure (e.g., table $T_Q$). Thus, each hash in the plurality of Q hashes corresponds to a respective hash data structure (e.g., a table $T_Q$) in a plurality of Q hash data structures. FIG. 8 illustrates an example of a plurality of hash data structures (e.g., Hash1, Hash2, ... Hash8), where each hash data structure includes a plurality of stored hashes comprising a hash value and a corresponding read identifier (e.g., R1, R2, R3, S1, S2, S3). As illustrated in FIG. 8, hash data structures are generated using input files in FASTQ format, where each respective input file corresponds to a respective biological sample S1, S2, and S3. Each entry (e.g., colored block) in the hash data structure represents a hashed R1 sequence. Hash values are denoted by the shading and/or pattern of the block (e.g., all blocks colored light gray represent entries having the same first hash value, all blocks colored medium gray represent entries having the same second hash value that is different from the first hash value, all blocks colored black represent entries having the same third hash value that is different from either the first or the second hash value, etc.). S1, S2, and S3 denote the sample ID and/or the file ID, while R1, R2, and R3 denote the sequence read ID. Note that the terms "R1", "R2", and "R3" are used in FIG. 8 to specify a first sequence read, a second sequence read, and a third sequence read, and should not be confused with the generic term "R1" used to denote the R1 sequence comprising the barcode and UMI.

Referring to block 1328, the method further comprises processing each table $T_Q$, where the processing comprises grouping hashes by hash value (block 1330), identifying hash value groups comprising heterogeneous sample IDs (block 1332), and storing unique sequence read pairs in a heterogeneous data structure (e.g., a sorted table $T_M$) (block 1334). In some preferred embodiments, each unique sequence read pair is a pair of entries in the hash data structure To comprising a unique combination of sample ID, file ID, and/or sequence read ID (e.g., a unique 6-tuple). For example, FIG. 8 provides examples of hash data structures where the hashes are grouped by hash value. In particular, the hash data structure for Hash 1 illustrates a first hash value group (e.g., medium gray blocks), and the hash data structure for Hash8 illustrates a first and a second hash value group (e.g., medium gray and black blocks). Both Hash1 and Hash8 comprise hash value groups comprising heterogeneous mixtures of sample IDs (e.g., R1 corresponding to both S1 and S2). Then, using the hash data structures illustrated in FIG. 8, unique sequence read pairs can be identified and stored in a heterogeneous data structure $T_M$, which would comprise 3 entries: S1/R1-S2/R1 (from Hash1); S1/R1-S2/R1 (from Hash8); and S1/R3-S2/R3 (from Hash8).

Referring to block 1336, the method further comprises filtering erroneous sequence reads from the plurality of sequence reads (e.g., in an input FASTQ file) using information stored in heterogeneous data structure $T_M$. Referring to block 1338, the filtering is performed by removing, from each respective plurality of sequence reads corresponding to each respective sample ID, the subset of sequence reads comprising a respective R1 sequence if there are at least a threshold number of entries for the respective R1 sequence with the respective sample ID in heterogeneous data structure $T_M$. In some preferred embodiments, the threshold number of entries in heterogeneous data structure $T_M$ is represented by a value P that must be no greater than the number of hashes Q. If the number of entries for the respective R1 sequence with the respective sample ID in heterogeneous data structure $T_M$ is less than P, then the subset of sequence reads comprising the respective R1 sequence is retained in an output file (e.g., an output FASTQ file).

For example, referring again to FIG. 8, the threshold number of entries P is 2. Iterating concurrently through input file S1.fq and heterogeneous data structure $T_M$ for the first sequence read "R1" reveals two entries in heterogeneous data structure $T_M$ comprising the first sequence read ID "R1" for sample 1 (e.g., S1/R1-S2/R1 from Hash1 and S1/R1-S2/R1 from Hash8). Because P=2, the first sequence read "R1" satisfies the requirements for filtering. S1/R1 and S2/R1 are thus presumed to be from the same molecule and have index-hopped, and will be filtered out from the output file.

Conversely, iterating concurrently through input file S1.fq and heterogeneous data structure $T_M$ for the third sequence read "R3" reveals one entry in heterogeneous data structure $T_M$ comprising the third sequence read ID "R3" for sample 1 (e.g., S1/R3-S2/R3 from Hash8). Because P=2, the third sequence read "R3" fails to satisfy the requirements for filtering. Thus, S1/R3 and S2/R3 are not presumed to be from the same molecule, and will be retained in the output file.

In some alternative embodiments, the subset of sequence reads that satisfy the requirements for filtering are not removed from each respective plurality of sequence reads corresponding to each respective sample ID, if the sample from which the subset of sequence reads originated can be presumed by statistical testing. In some such embodiments, the subset of sequence reads are retained in the plurality of sequence reads corresponding to the respective sample ID from which they originated, but are removed from each plurality of sequence reads corresponding to each respective sample ID other than the sample ID of origin.

Example 4. Performance Measures for Index Hopping Filters

Performance of a method of filtering out erroneous sequence reads was measured, in accordance with some embodiments of the present disclosure.

Experiment: Comparison of sequence read filtration using index hopping filters versus dual-indexed sequence reads.

Figure 9:
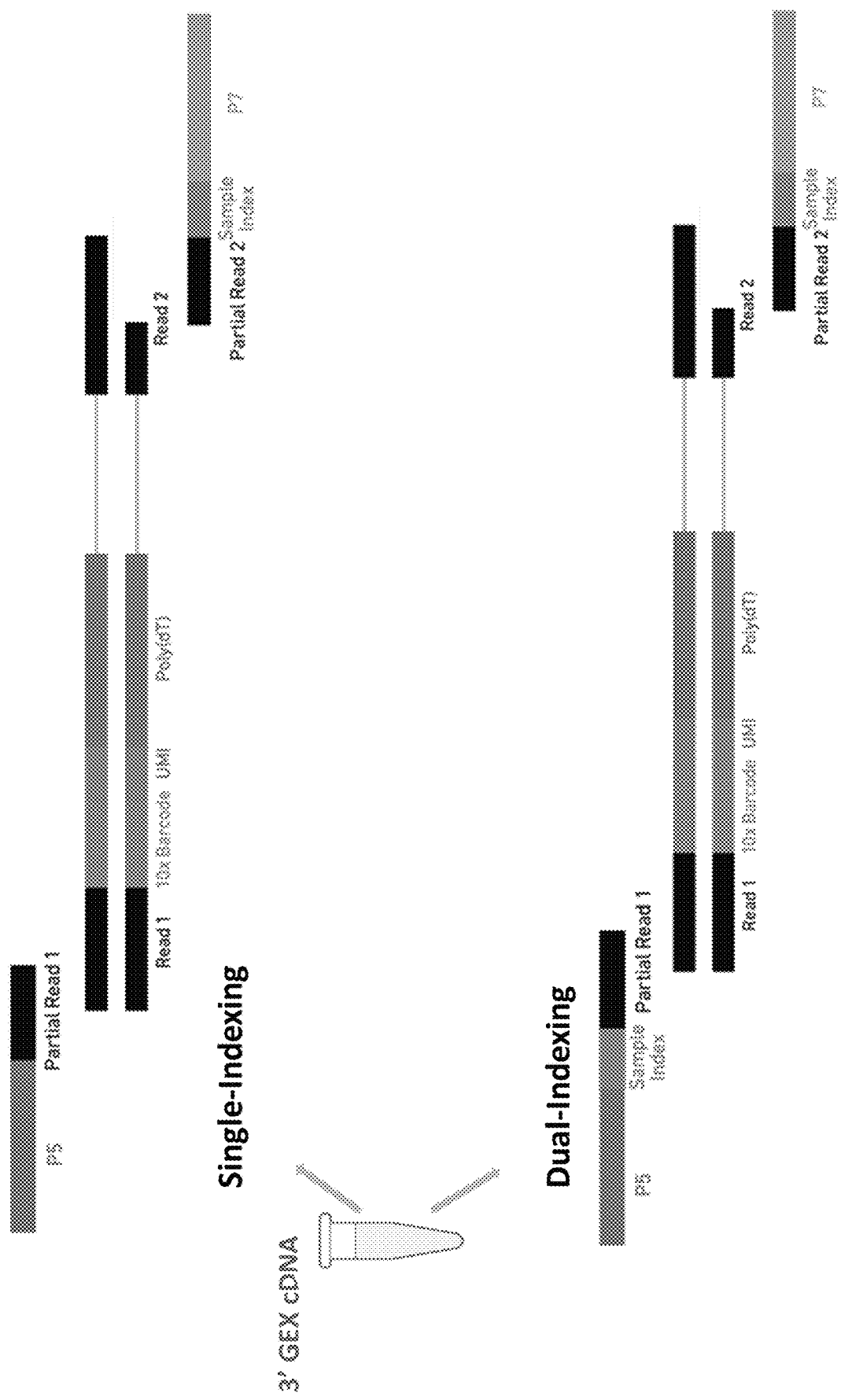
FIG. 9 illustrates an example of single versus dual-indexing of nucleic acid molecules to obtain a plurality of sequence reads, in accordance with some embodiments of the present disclosure.

A first experiment was designed using sequence reads obtained from a sequencing flow cell, and the performance of a method for sequence read filtration was compared with a method using dual-indexed sequence reads as a control (e.g., ground truth). Two experimental designs were used for the performance measure. First, 7 replicates each comprising approximately 1,000 peripheral blood mononuclear cell (PBMC) cDNA samples were separated into two groups and used for 3' gene expression (GEX) library construction. During sample index PCR, an annealing temperature gradient was performed to examine the impact of this temperature on library quality and sequencing performance. Sequencing libraries were constructed using either single-indexing or dual-indexing, as illustrated in FIG. 9.

Figure 10:
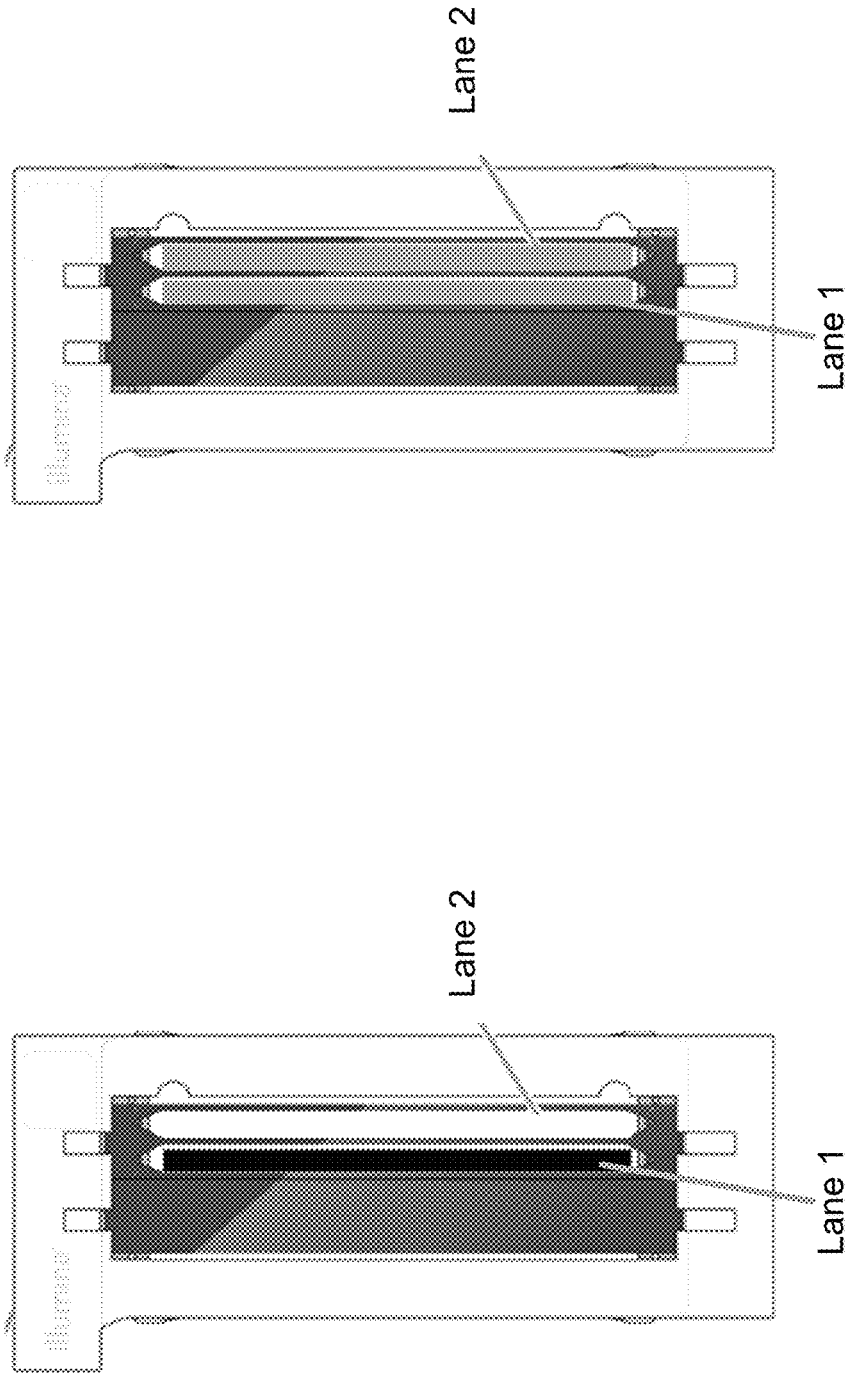
FIG. 10 illustrates two examples of a sequencing flow cell used to obtain a plurality of sequence reads, in accordance with some embodiments of the present disclosure.

As illustrated in FIG. 10, in a first experimental design, two lanes of an Illumina NovaSeq S1 sequencing flow cell (Flowcell ID HG7LTDRXX) were loaded with single-indexed GEX libraries (e.g., Lane 1; black) and dual-indexed GEX libraries (e.g., Lane 2; white). In a second experimental design, the single- and dual-indexed GEX libraries were pooled, and both lanes of an Illumina sequencing flow cells (Flowcell ID HGFGTDRXX) were loaded with the pooled single- and dual-indexed GEX libraries (e.g., Lanes 1 and 2; gray). GEX libraries were subsequently sequenced and analyzed for success. For Flowcell ID HG7LTDRXX, sequencing analyses were considered successful when indexed to the full 10 bp for dual-indexed samples (IDs: 148229-148235) and single-indexed samples (IDs: 150386-150392). Sequencing analysis were considered unsuccessful for single-indexed samples comprising misspecified 8 bp sample indices (IDs: 148222-148228). For Flowcell ID HGFGTDRXX, sequencing analyses were considered successful when indexed to the full 10 bp for dual-indexed samples (IDs: 148264-148270), and unsuccessful for single-indexed samples comprising misspecified 8 bp sample indices (IDs: 148257-148263).

The results of the sequencing analysis are presented in FIG. 11. "Dual Index Loss" indicates the fraction of sequence reads removed from the plurality of sequence reads by dual-indexing analysis. Because dual-indexing results in sequence reads comprising two unique sample indices flanking the read insert, this method establishes a ground truth by identifying sequence reads where one of the pair of observed (e.g., sequenced) sample indices differs from the expected (e.g., original) sample index. "Filtered Loss" indicates the fraction of sequence reads removed from the plurality of sequence reads by index hopping filtration (IHF). The top panel of FIG. 11 illustrates that dual-indexing analysis and IHF both removed similar fractions of sequence reads from dual-indexed GEX libraries sequenced alone (e.g., the first experimental design).

Next, an analysis was performed to determine whether the subset of sequence reads removed by dual-indexing analysis and the subset of sequence reads removed by IHF overlap (e.g., whether IHF removes the same or different sequence reads removed by dual-indexing analysis). For this analysis, the subset of sequence reads removed by dual-indexing (DI) (e.g., "All Reads") were divided into two categories: "Cell Barcode Reads" and "Non-Cell Barcode Reads." As used herein, the term "Cell Barcode Reads" refers to two or more barcode reads that are interpolated into a single sequence read during sequencing, resulting in barcode overlap (e.g., homogenization). As used herein, the term "Non-Cell Barcode Reads" refers to one or more barcodes originating from a first cell context that are erroneously observed in a second cell context (e.g., invasion). Interestingly, only ~2% of index-hopped reads removed by dual-indexing analysis were also removed by IHF. However, the degree of barcode overlap (e.g., homogenization) was observed to be extremely low in the experimental samples (approximately 0.002% of all sequence reads). Therefore, the removal of Non-Cell Barcode Reads, rather than the removal of Cell Barcode Reads, by IHF was deemed to be of greater importance to the performance measure. Consequently, the top panel of FIG. 11 illustrates that IHF removed greater than 95% of the index-hopped non-cell barcode reads that were previously observed to be removed by dual-indexing analysis. Of the sequence reads removed by dual-indexing but not identified by IHF, greater than 99% comprised a unique barcode and UMI sequence. Thus, these data indicate a high concordance between the performances of IHF compared to the ground truth dual-indexing method.

The bottom panel of FIG. 11 illustrates that similar performance was also observed for sequencing assays from the second experimental design, in which single- and dual-indexed GEX libraries were pooled together prior to sequencing. In this comparison, the presence of single-indexed GEX libraries in the pooled samples resulted in a higher fraction of sequence reads removed by IHF compared to dual-indexing analysis. Specifically, the single-indexed GEX libraries could be filtered by IHF but were by nature incompatible with dual-indexing analysis, such that approximately twice as many sequence reads were removed by IHF compared to dual-indexing. Nevertheless, a high percentage of both All Reads (greater than 93%) and Non-Cell Barcode Reads (greater than 98%) removed by dual-indexing analysis were also removed by IHF, further supporting the accuracy of the filtration method.

Figure 12:
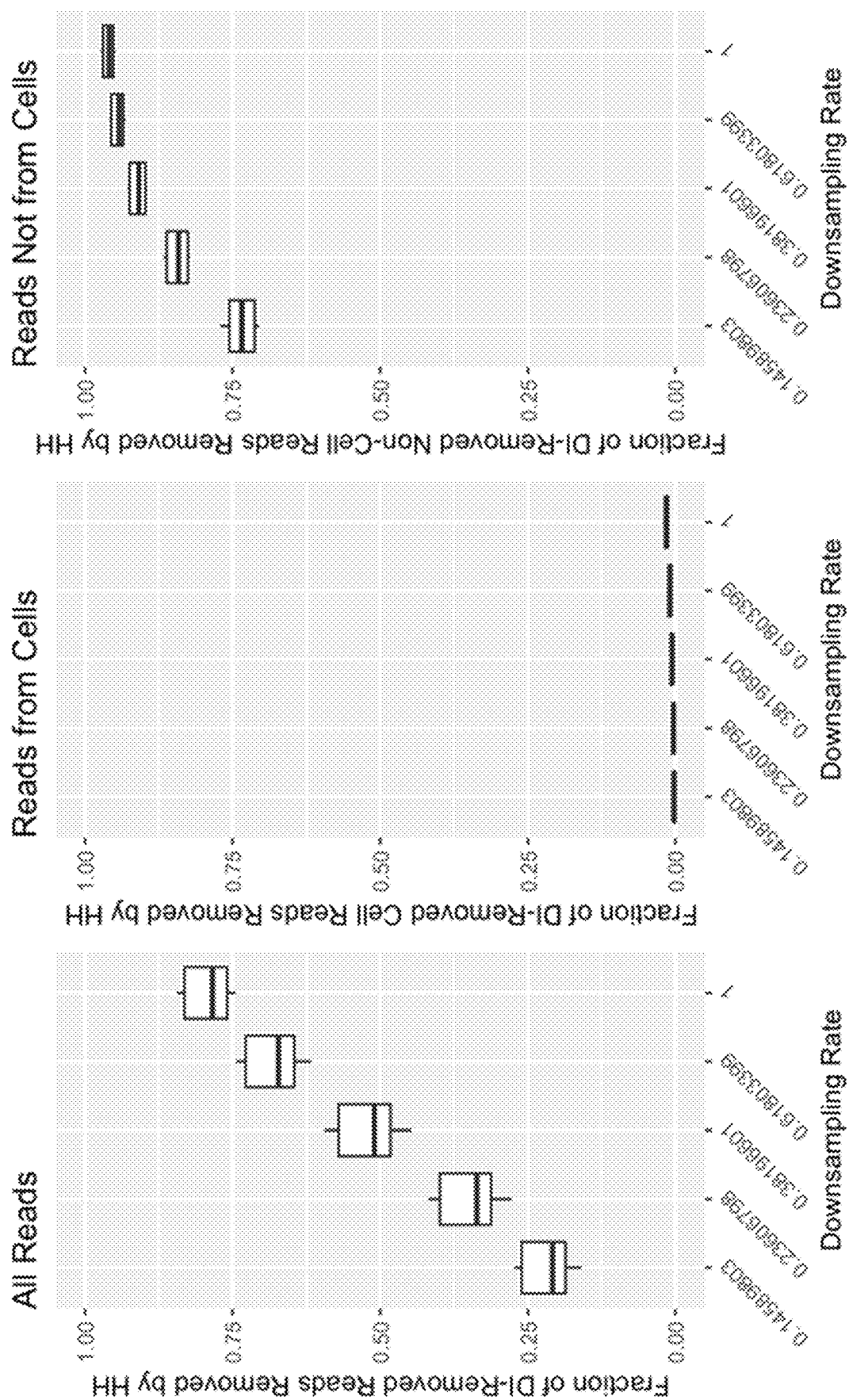
FIG. 12 illustrates the performance of a method of filtering out erroneous sequence reads as a function of read depth, in accordance with some embodiments of the present disclosure.

FIG. 12 illustrates the performance of the IHF method as a function of read depth, in accordance with some embodiments of the present disclosure. A dual-indexing and IHF filtration was performed using dual-indexed sequence reads at a sequencing depth of 116516 mean reads per cell. The data was then downsampled to measure the dependence of the filtration method on sequencing depth, for All Reads (e.g., left panel), Cell Barcode Reads (e.g., "Reads from Cells"; middle panel), and Non-Cell Barcode Reads (e.g., "Reads Not from Cells"; right panel). The x-axis denotes the downsampling rate at 0.14589803, 0.23606798, 0.38196601, 0.61803399, and 1, corresponding to sequencing depths of 17454, 28010, 44898, 72306, and 116516 mean reads per cell, respectively. The y-axis denotes the fraction of sequence reads removed by dual-indexing (DI) also removed by IHF (HH; e.g., Hash Hopper). The figure shows that performance of the filtration method is depth-dependent and degrades with lower depth, for all categories of DI-removed sequence reads. In particular, for Non-Cell Barcode Reads (right panel), the method is ~92% effective at the recommended sequencing depth of ~50,000 mean reads per cell, and 75% effective at the minimum recommended sequencing depth of ~20,000 mean reads per cell. In some cases, downsampling the sequence reads to below the minimum recommended sequencing depth (e.g., removing 90% or more of the sequence reads) may drop the cells below the threshold for recognition by cell calling algorithms, effectively removing them from the outputs.

Example 5. Example Computer Implementation of a Method for Index Hopping Filtration A method for index hopping filtration (e.g., HashHopper) can be implemented using a computer program and/or a command line scheme. For example, in some embodiments, a typical workflow can comprise downloading a program (e.g., a compiled statically linked single binary) from a cloud-based server. The workflow further comprises determining the applicable inputs (e.g., input FASTQ files) and outputs (e.g., output FASTQ and/or csv files), and running the index hopping filtration method. The method can optionally comprise additional programs, tools, and/or outputs following the performance of the filtration method (e.g., Cell Ranger, web summary outputs, etc.).

Example command-line schema include a "filter" command (e.g., hashhopper filter) and a "make csv" command (e.g., hashhopper mkcsv). The filter command filters index-hopped reads from FASTQ files, using, as input, a "mkfastq" or "bcl2fastq" output directory or a csv file describing the inputs, and optionally a thread-number parameter that defines the maximum number of threads used (e.g., "max-threads", where the default is the number of cores used in the processor of the computing system). Outputs for the filter command include an output path for filtered FASTQ files.

The make csv command generates a comma separated values (csv) configuration from a "mkfastq" or "bcl2fastq" output directory, using, as input, a "mkfastq" or "bcl2fastq" output directory or a csv file describing the inputs. Outputs for the make csv command include a configuration csv file outputted to STDOUT. In some embodiments, STDOUT can be directed to a file of the user's choosing. For example, in some embodiments, the input logic processes "mkfastq" output structure and will work anywhere along the path from the mkfastq <pipestance> to the flowcell folder inside <pipestance>outs/fastq_path.

FIG. 14A illustrates an example csv configuration where the output is composed in tabular format and indicates the file ID and the corresponding sample ID of each sequence read in the plurality of sequence reads. FIG. 14B illustrates an example csv configuration file of inputs, with paths canonicalized. In some embodiments, the generation of the csv configuration ensures that multiple derivative samples prepared by simultaneous sequencing (e.g., using gene expression libraries) can be analyzed and filtered without overzealously removing sequence reads that have not undergone index hopping. In some alternative embodiments, csv configurations are not required, and the output is produced by printing from the directory structure of configured and demultiplexed BCL or FASTQ files.

FIG. 15 illustrates an example of a command line run, with corresponding outputs, of a "hashhopper filter" command. A common output for the filter tool is a web summary that reports general run information as well as a summary of results. For example, in some embodiments, the web summary will report, e.g., the version of the tool, the inputs provided, the number of sequence reads, the percentage of filtered sequence reads, confusion matrices, and/or sequence reads removed as heavy hitters. FIG. 16 illustrates an example of a web summary output detailing the sample IDs, starting number of reads, and number of reads removed for sequence reads filtered by sample, as well as run details including input path and HashHopper version. In some embodiments, the web summary is produced by a bioinformatics pipeline as a high-level web summary object.

An example implementation comprises a sequencing reaction performed on a NovaSeq S1 or S2 flow cell and a filtration method performed on a computing environment including a multi-core processor (e.g., 8 or 16 cores) and network file system (NFS) storage. Other implementations are possible, as will be apparent to one skilled in the art.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first object could be termed a second object, and, similarly, a second object could be termed a first object, without changing the meaning of the description, so long as all occurrences of the "first object" are renamed consistently and all occurrences of the "second object" are renamed consistently. The first object and the second object are both objects, but they are not the same object.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of filtering out erroneous sequence reads, the method comprising:

at a computer system having one or more processors, and memory storing one or more programs for execution by the one or more processors:

(A) obtaining a plurality of sequence reads, in electronic form, from a multiplexed sequencing reaction, wherein the plurality of sequence reads comprises 10,000 sequence reads;

each respective sequence read in the plurality of sequence reads comprises a corresponding insert portion, a corresponding first non-insert portion consisting of N nucleotide positions, and a corresponding second non-insert portion consisting of M nucleotide positions, N and M are positive integers, each corresponding first non-insert portion represents an identifier of a unique molecule, each corresponding second non-insert portion comprises a sample index, the plurality of sequence reads includes one or more first sequence reads from a first sample that each have a first value for the sample index, the plurality of sequence reads includes one or more second sequence reads from a second sample that each have a second value for the sample index;

(B) performing a uniqueness test by:

(i) obtaining a table $T_{HH}$ that comprises the corresponding first and second non-insert portions of each sequence read in the plurality of sequence reads, lexicographically sorted on the first non-insert portion, (ii) identifying each respective first non-insert portion represented in $T_{HH}$ for which a predetermined second threshold number of unique second non-coding portion pairs can be made from pairs of sequence reads in Tim having the respective first non-insert portion, wherein each second non-coding portion pair in the threshold number of unique second non-coding portion pairs comprises an independent pair of different second non-coding portion values, and (iii) removing from the plurality of sequence reads each sequence read in the plurality of sequence reads having an identified first non-insert portion;

(C) for each respective hash in a plurality of hashes, forming a corresponding hash data structure, wherein the corresponding hash data structure includes a representation of each respective sequence read, in the plurality of sequence reads, and comprises a hash value, of length L nucleotide positions, wherein L is less than N, formed by hashing at least the corresponding first non-insert portion of the respective sequence read in accordance with the respective hash, thereby forming a plurality of hash data structures;

(D) creating a heterogenous data structure comprising a plurality of entries by identifying a plurality of unique sequence read pairs in the plurality of hash data structures in greater than linear time, wherein each respective sequence read pair in the plurality of unique sequence read pairs includes a corresponding first sequence read and a corresponding second sequence read sharing a common hash value and having different second values for the sample index, and each corresponding entry in the heterogeneous data structure comprises a respective unique sequence read pair in the plurality of unique sequence read pairs, wherein the corresponding entry includes at least the corresponding first and second non-insert portions of the corresponding first sequence read and the corresponding first and second non-insert portions of the corresponding second sequence read of the respective unique sequence read pair;

(E) identifying a set of sequence reads using the heterogeneous data structure, wherein each sequence read in the set of sequence reads has a corresponding first non-insert portion value that appears more than a predetermined first threshold number of times in the heterogeneous data structure; and (F) removing the set of sequence reads from the plurality of sequence reads thereby filtering out erroneous sequence reads.

2. The method of claim 1, wherein the plurality of sequence reads is from more than five different biological samples and comprises more than one hundred thousand sequence reads.

3. The method of claim 1, wherein the unique molecular identifier has a nucleotide length of between 8 nucleotide positions and 20 nucleotide positions.

4. The method of claim 1, wherein the unique molecular identifier encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1 \times 10^{12}\}$.

5. The method of claim 1, wherein the corresponding first non-insert portion of each respective sequence read in the plurality of sequences reads comprises a corresponding independent barcode, from a plurality of barcodes, wherein each barcode in the plurality of barcodes represents a different gel bead-in emulsion in a plurality of gel bead-in emulsions.

6. The method of claim 5, wherein each barcode in the plurality of barcodes encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1 \times 10^{12}\}$.

7. The method of claim 1, wherein
N is between 10 and 100, and
M is between 5 and 20.

8. The method of claim 7, wherein L is between 4 and 99.

9. The method of claim 1, wherein
N is between 36 and 40, and
M is 8.

10. The method of claim 1, wherein the hash value formed by hashing at least the corresponding first non-insert portion of the respective sequence read in accordance with the respective hash comprises forming the hash value from a predetermined subset of nucleotide positions in the corresponding first non-insert portion, wherein the predetermined subset of nucleotide positions is defined by the respective hash and is unique to the respective hash.

11. The method of claim 10, wherein each respective hash in the plurality of hashes defines a different predetermined subset of nucleotide positions in the first non-insert portion.

12. The method of claim 1, wherein the plurality of hashes consists of between three and one hundred hashes.

13. The method of claim 1, wherein the predetermined second threshold number is a number between 500 and 100,000.

14. The method of claim 1, wherein
the corresponding hash data structure is a corresponding first table,
each row in the corresponding first table includes the representation of a respective sequence read in the plurality of sequence reads,
the representation of each sequence read further comprises the corresponding second portion of the sequence read, and
the corresponding first table is sorted on hash value.

15. The method of claim 14, wherein each sequence read further comprises a file identifier identifying a file name that contains the sequence read and the representation of each sequence read in the corresponding first table further comprises the file identifier.

16. The method of claim 1, wherein
the heterogeneous data structure is a second table,
each row in the second table includes a corresponding entry, and
the second table is sorted in lexicographic field order using at least the first and second non-insert portions of the corresponding first sequence read and the first and second non-insert portions of the corresponding second sequence read of each corresponding entry in the second table.

17. The method of claim 16, wherein the corresponding entry further includes a file identifier of the corresponding first sequence read and the file identifier of the corresponding second sequence read of the respective unique sequence read pair.

18. The method of claim 1, wherein the plurality of sequence reads includes sequence reads from a plurality of biological samples, wherein each biological sample in the plurality of biological samples is assigned a different sample index value for the sample index.

19. The method of claim 1, wherein the plurality of sequence reads is obtained by loading test nucleic acids onto a plurality of gel bead-in emulsions beads.

20. The method of claim 1, wherein the first predetermined threshold number of times is an integer that is greater than 1 and that is less than a number of hashes in the plurality of hashes.

21. The method of claim 1, wherein the first predetermined threshold number of times is four, five, six, or seven and the number of hashes in the plurality of hashes is eight.

22. The method of claim 1, wherein the multiplexed sequencing is a single-strand consequence sequencing or a duplex consensus sequencing.

23. The method of claim 1, wherein the first non-insert portion comprises two or more predetermined non-contiguous portions of each respective sequence read in the plurality of sequence reads.

24. The method of claim 1, wherein the plurality of sequence reads is scRNA-seq sequence reads or scATAC-seq sequence reads.

25. The method of claim 1, wherein the plurality of sequences reads collectively map to one megabase of a reference genome with a coverage of at least 1.

26. A computing system, comprising:
one or more processors;
memory storing one or more programs to be executed by the one or more processors;
the one or more programs comprising instructions for:
(A) obtaining a plurality of sequence reads, in electronic form, from a multiplexed sequencing reaction, wherein
the plurality of sequence reads comprises 10,000 sequence reads;
each respective sequence read in the plurality of sequence reads comprises a corresponding insert portion, a corresponding first non-insert portion consisting of N nucleotide positions, and a corresponding second non-insert portion consisting of M nucleotide positions,
N and M are positive integers,
each corresponding first non-insert portion represents an identifier of a unique nucleic acid molecule,
each corresponding second non-insert portion comprises a sample index,
the plurality of sequence reads includes one or more first sequence reads from a first sample that each have a first value for the sample index,
the plurality of sequence reads includes one or more second sequence reads from a second sample that each have a second value for the sample index;
(B) performing a uniqueness test by:
(i) obtaining a table $T_{HH}$ that comprises the corresponding first and second non-insert portions of each sequence read in the plurality of sequence reads, lexicographically sorted on the first non-insert portion,
(ii) identifying each respective first non-insert portion represented in $T_{HH}$ for which a predetermined second threshold number of unique second non-coding portion pairs can be made from pairs of sequence reads in $T_{HH}$ having the respective first non-insert portion, wherein each second non-coding portion pair in the threshold number of unique second non-coding portion pairs comprises an independent pair of different second non-coding portion values, and
(iii) removing from the plurality of sequence reads each sequence read in the plurality of sequence reads having an identified first non-insert portion;
(C) for each respective hash in a plurality of hashes, forming a corresponding hash data structure, wherein the corresponding hash data structure includes a representation of each respective sequence read in the plurality of sequence reads that comprises a hash value, of length L nucleotide positions, wherein L is less than N, formed by hashing at least the corresponding first non-insert portion of the respective sequence read in accordance with the respective hash, thereby forming a plurality of hash data structures;
(D) creating a heterogenous data structure comprising a plurality of entries by identifying a plurality of unique sequence read pairs in plurality of hash data structures in greater than linear time, wherein
each respective sequence read pair in the plurality of unique sequence read pairs includes a corresponding first sequence read and a corresponding second sequence read sharing a common hash value and having different second values for the sample index, and
each corresponding entry in the heterogeneous data structure comprises a respective unique sequence read pair in the plurality of unique sequence read pairs, wherein the corresponding entry includes at least the corresponding first and second non-insert portions of the corresponding first sequence read and the corresponding first and second non-insert portions of the corresponding second sequence read of the respective unique sequence read pair;
(E) identifying a set of sequence reads using the heterogeneous data structure, wherein each sequence read in the set of sequence reads has a corresponding first non-insert portion value that appears more than a predetermined first threshold number of times in the heterogeneous data structure; and
(F) removing the set of sequence reads from the plurality of sequence reads thereby filtering out erroneous sequence reads.

27. A non-transitory computer readable storage medium storing one or more programs configured for execution by a computer, the one or more programs comprising instructions for:
(A) obtaining a plurality of sequence reads, in electronic form, from a multiplexed sequencing reaction, wherein
the plurality of sequence reads comprises 10,000 sequence reads;
each respective sequence read in the plurality of sequence reads comprises a corresponding insert portion, a corresponding first non-insert portion consisting of N nucleotide positions, and a corresponding second non-insert portion consisting of M nucleotide positions,
N and M are positive integers,
each corresponding first non-insert portion represents an identifier of a unique molecule,
each corresponding second non-insert portion comprises a sample index,
the plurality of sequence reads includes one or more first sequence reads from a first sample that each have a first value for the sample index,
the plurality of sequence reads includes one or more second sequence reads from a second sample that each have a second value for the sample index;

(B) performing a uniqueness test by:
(i) obtaining a table $T_{HH}$ that comprises the corresponding first and second non-insert portions of each sequence read in the plurality of sequence reads, lexicographically sorted on the first non-insert portion,
(ii) identifying each respective first non-insert portion represented in $T_{HH}$ for which a predetermined second threshold number of unique second non-coding portion pairs can be made from pairs of sequence reads in $T_{HH}$ having the respective first non-insert portion, wherein each second non-coding portion pair in the threshold number of unique second non-coding portion pairs comprises an independent pair of different second non-coding portion values, and
(iii) removing from the plurality of sequence reads each sequence read in the plurality of sequence reads having an identified first non-insert portion;
(C) for each respective hash in a plurality of hashes, forming a corresponding hash data structure, wherein the corresponding hash data structure includes a representation of each respective sequence read in the plurality of sequence reads that comprises a hash value, of length L nucleotide positions, wherein L is less than N, formed by hashing at least the corresponding first non-insert portion of the respective sequence read in accordance with the respective hash, thereby forming a plurality of hash data structures;
(D) creating a heterogenous data structure comprising a plurality of entries by identifying a plurality of unique sequence read pairs in the plurality of hash data structures in greater than linear time, wherein
each respective sequence read pair in the plurality of unique sequence read pairs includes a corresponding first sequence read and a corresponding second sequence read sharing a common hash value and having different second values for the sample index, and
each corresponding entry in the heterogeneous data structure comprises a respective unique sequence read pair in the plurality of unique sequence read pairs, wherein the corresponding entry includes at least the corresponding first and second non-insert portions of the corresponding first sequence read and the corresponding first and second non-insert portions of the corresponding second sequence read of the respective unique sequence read pair;
(E) identifying a set of sequence reads using the heterogeneous data structure, wherein each sequence read in the set of sequence reads has a corresponding first non-insert portion value that appears more than a threshold number of times in the heterogeneous data structure; and
(F) removing the set of sequence reads from the plurality of sequence reads thereby filtering out erroneous sequence reads.

\* \* \* \* \*

SEQUENCE LISTING

<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Hypothetical Sequence

<400> SEQUENCE: 1
ttaactcgta gaagga                                                    16

<210> SEQ ID NO 2
<211> LENGTH: 10
<212> TYPE: DNA
<213> ORGANISM: Artificial Sequence
<220> FEATURE:
<223> OTHER INFORMATION: Hypothetical Sequence

<400> SEQUENCE: 2
gtccggcgac                                                           10

```
<210> SEQ ID NO 3
<211> LENGTH: 28
<212> TYPE: DNA
<213> ORGANISM: Artificial Sequence
<220> FEATURE:
<223> OTHER INFORMATION: Hypothetical Sequence

<400> SEQUENCE: 3
atgcatgaat gccatagaca ggcatcga                                       28

<210> SEQ ID NO 4
<211> LENGTH: 24
<212> TYPE: DNA
<213> ORGANISM: Artificial Sequence
<220> FEATURE:
<223> OTHER INFORMATION: Hypothetical Sequence

<400> SEQUENCE: 4
atgatgaatg ccaaacagca tcga                                           24

<210> SEQ ID NO 5
<211> LENGTH: 24
<212> TYPE: DNA
<213> ORGANISM: Artificial Sequence
<220> FEATURE:
<223> OTHER INFORMATION: Hypothetical Sequence

<400> SEQUENCE: 5
atgatgaatg ccaaacagca tcga                                           24

<210> SEQ ID NO 6
<211> LENGTH: 21
<212> TYPE: DNA
<213> ORGANISM: Artificial Sequence
<220> FEATURE:
<223> OTHER INFORMATION: Hypothetical Sequence

<400> SEQUENCE: 6
atgatgaatg ccaaacagca t                                              21

<210> SEQ ID NO 7
<211> LENGTH: 21
<212> TYPE: DNA
<213> ORGANISM: Artificial Sequence
<220> FEATURE:
<223> OTHER INFORMATION: Hypothetical Sequence

<400> SEQUENCE: 7
atgatgaatg ccaaacagca t                                              21
```